US008114586B2

(12) United States Patent
Foung et al.

(10) Patent No.: US 8,114,586 B2
(45) Date of Patent: *Feb. 14, 2012

(54) PREVENTION AND TREATMENT OF HCV INFECTION EMPLOYING ANTIBODIES DIRECTED AGAINST CONFORMATIONAL AND LINEAR EPITOPES

(75) Inventors: Steven K. H. Foung, Stanford, CA (US); Kenneth G. Hadlock, San Francisco, CA (US); Zhen-yong Keck, Redwood City, CA (US)

(73) Assignee: Board of Trustees of Leland Stanford Junior University, Palo Alto, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 12/332,832

(22) Filed: Dec. 11, 2008

(65) Prior Publication Data

US 2009/0202482 A1 Aug. 13, 2009

Related U.S. Application Data

(63) Continuation of application No. 10/958,624, filed on Oct. 5, 2004, now abandoned, which is a continuation-in-part of application No. 10/188,608, filed on Jul. 2, 2002, now abandoned, which is a continuation-in-part of application No. 09/728,720, filed on Dec. 1, 2000, now Pat. No. 7,091,324, which is a continuation-in-part of application No. 09/430,489, filed on Oct. 29, 1999, now Pat. No. 6,692,908, which is a continuation of application No. 09/187,057, filed on Nov. 5, 1998, now abandoned.

(51) Int. Cl.
*A61K 38/00* (2006.01)
*A61K 39/00* (2006.01)
*C07K 14/18* (2006.01)
*C07K 16/08* (2006.01)
*C07K 16/10* (2006.01)

(52) U.S. Cl. .................... 435/5; 435/339; 530/388.3

(58) Field of Classification Search ................ None
See application file for complete search history.

(56) References Cited

U.S. PATENT DOCUMENTS 5,849,987 A 12/1998 Reisner et al.

OTHER PUBLICATIONS

Rehemann B et al. "Immunology of hepatitis B virus and hepatitis C virus infection". Nat Rev Immunol. Mar. 2005;5(3):215-29. Review.*
Bartenschlager R. et al. "replication of hepatitis C virus" J. Gen virology, vol. 81, pp. 1631-1648. 2000.*
Charlton M "Management of recurrence of hepatitis C infection following liver transplantation". Minerva Chir. Oct. 2003;58(5):717-24.*
Davis GL et al. "Hepatitis C virus infection-pathobiology and implication for new therapeutic options" Dig Dis Sci. vol. 52, p. 857-875, (2007).*
Keller MA et al. "Passive immunity in prevention and treatment of infectious diseases". Clin Microbiol Rev. Oct. 2000;13(4):602-14.*
Akatsuka, et al., "B-cell Epitopes on the Hepatitis C Virus Nucleocapsid Protein Determined by Human Monospecific Antibodies" *Hepatology.* 18:503-510, 1993.
Al-Hemsi, et al., "Liver transplantation for hepatitis B cirrhosis: clinical sequela of passive immunization" *Clin. Transplant.* 10: 668-675, 1996.
Allison, et al., "The Mode of Action of Immunological Adjuvants" *Biol. Stand.* 92: 3-11, 1998.
Andrus, et al., "Passive Immunization with a Human Immunodeficiency Virus type 1-Neutralizing monoclonal Antibody in Hu-PBL-SCID Mice: Isolation of a Neutralization Escape Variant" *J. Infect. Dis.* 177: 889-97, 1998.
Arp, et al., "A Source of Glycosylated Human T-Cell Lymphotropic Virus Type 1 Envelope Protein: Expression of gp46 by the Vaccinia Virus/T7 Polymerase System" *J. Virology,* 70: 7349-7359, 1996.
Bartosch, et al., "Infectious Hepatitis C Virus Pseudo-particles Containing Functional E1-E2 Envelope Protein Complexes" *J. exp. Med.* 197: 633-642, 2003.
Bassett, et al., "Analysis of Hepatitis C Virus-Inoculated Chimpanzees Reveals Unexpected Clinical Profiles" *J. Virology.* 72: 2589-2599.
Chanh, et al., "Monoclonal Anti-Idiotypic Antibody mimics the CD4 Receptor and Binds Human Immunodeficiency Virus" *Proc. Natl. Acad. Sci. USA,* 184: 3891-3895, 1987.
Chien, et al., "Use of a Novel Hepatitis C Virus (HCV) Major-Epitope Chimeric Polypeptide for Diagnosis of HCV Infection" *J. Clin. Microbiol.* 37: 1393-1397, 1999.
Cocquerel, et al., "The Transmembrane Domain of Hepatitis C Virus Glycoprotein E1 Is a Signal for Static Retention in the Endoplasmic Reticulum" *J. Virol.* 73: 2641-2649, 1999.
Da Silva Cardoso, et al., "Anti-HCV envelope prevalence in blood donors from Baden-Wurttemberg" *Ann.Hematol.* 74: 135-7, 1997.
Da Silva Cardoso, et al., "Isolation and Characterization of Human Monoclonal Antibodies Against Hepatitis C Virus Envelope Glycoproteins" *J. Med. Virol.* 55: 28-34, 1998.
de Lalla, et al., "Properties of a human monoclonal antibody specific for the NS4 region of hepatitis C virus" *J. Hepatol.* 18: 163-167, 1993.

(Continued)

*Primary Examiner* — Bo Peng
(74) *Attorney, Agent, or Firm* — Choate, Hall & Stewart LLP

(57) ABSTRACT

Conformational epitopes of the envelope proteins E1 and E2 of the Hepatitis C virus (HCV) have been identified and characterized using a panel of monoclonal antibodies derived from patients infected with HCV. These conserved conformational and linear epitopes of the HCV protein E1 or E2 have been determined to be important in the immune response of humans to HCV and may be particularly important in neutralizing the virus. Based on the identification of these conformational epitopes, vaccines containing peptides and mimotopes with these conformational epitopes intact may be prepared and administered to patients to prevent and/or treat HCV infection. The identification of four distinct groups of monoclonal antibodies with each directed to a particular epitope of E1 or E2 may be used to stratify patients based on their response to HCV and may be used to determine a proper treatment regimen. Pharmaceutical compositions for prevention and treatment of HCV, comprising one or more the monoclonal antibodies, are provided.

12 Claims, 55 Drawing Sheets

OTHER PUBLICATIONS

Deleersnyder, et al., "Formation of Native Hepatitis C Virus Glycoprotein Complexes" *J. of Virology*. 71: 697-704, 1997.
Dickson, et al., "Management of Posttransplantation Viral Hepatitis—Hepatitis B" *Liver Transpl. Surg*. 4(5 SupplI): S73-S78, 1998.
Dubuisson, et al., "Formation and Intracellular Localization of Hepatitis C Virus Envelope Glycoprotein Complexes Expressed by Recombinant Vaccinia and Sindbis Viruses" *J. Virol*. 68: 6174-6160, 1994.
Duvet, et al., "Hepatitis C Virus Glycoprotein Complex Localization in the Endoplasmic Reticulum Involves a Determinant for Retention and Not Retrieval" *J. Biol. Chem*. 273: 32088-32095, 1998.
Farci, et al., "Prevention of Hepatitis C Virus Infection in Chimpanzees After Antibody-Mediated in vitro Neutralization" *Proc. Natl. Acad. Sci. USA*, 91: 7792-7796, 1994.
Farci, et al., "Prevention of Hepatitis C Virus Infection in Chimpanzees by Hyperimmune Serum against the Hypervariable region 1 of the Envelope 2 Protein" *Proc. Natl. Acad. Sci. USA*, 93: 15394-15399, 1996.
Farci, et al., "Lack of Protective Immunity Against Reinfection with Hepatitis C Virus" *Science*. 258: 135-140, 1992.
Flint, et al., "Characterization of Hepatitis C Virus E2 Glycoprotein Interaction with a Putative Cellular Receptor, CD81" *J. Virology*. 73: 6235-6244, 1999.
Flint, et al., "Functional Analysis of Cell Surface-Expressed Hepatitis C Virus E2 Glycoprotein" *J. Virology*. 73: 6782-6790, 1999.
Foung, et al. "Development of microfusion techniques to generate human hybridomas", *J Immunol. Methods*. 134: 35-42, 1984.
Foung, et al., "Rescue of Human Monoclonal Antibody Production from an EBV-Transformed B Cell Line by Fusion to a Human-Mouse Hybridoma" *J. Immunol. Methods*. 70: 830-90, 1990.
Fournillier-Jacob, et al., "Processing of the E1 glycoprotein of hepatitis C virus expressed in mammalian cells" *J. Gen. Virol*. 77: 1055-1064, 1996.
Gane, et al., "Antibodies to Hepatitis C Virus Envelope Proeteins Correlate With Hepatitis C Viraemia After Liver Transplantation" *Transplantation*. 67: 78-84, 1999.
Harada, et al., "Establishment of a cell line constitutively expressing E2 glycoprotein of hepatitis C virus and humoral response of hepatitis C patients to the expressed protein" *Gen. Virol*. 76: 1223-1231, 1994.
Hijikata, et al., "Equilibrium Centrifugation Studies of Hepatitis C Virus: Evidence for Circulating Immune Complexes" *J. Virology*. 67: 1953-1958. 1993.
Houghton, et al., "Hepatitis C viruses", *In Fields, Knipe, Howley (eds) Virology*. Lippincott-Raven, Philadelphia, 1035-1058. 1996.
Ishii, et al., "High Titers of Antibodies Inhibiting the Binding of Envelope to Human Cells Correlate With Natural Resolution of Chronic Hepatitis C" *Hepatology*. 28: 1117-1120, 1998.
Kato, et al., "Humoral Immune Response to Hypervariable Region 1 of the Putative Envelope Glycoprotein (gp70) of Hepatitis C Virus" *J. Virol*. 67: 3923-3930, 1993.
Kimura, et al., "Attachment of Hepatitis C Virus to Cultured Cells: A Novel Predictive Factor for Successful Interferon Therapy" *J. Med. Virology*. 56: 25-32, 1998.
Kopecky, et al., "A Putative Host Cell Receptor for Tick-Borne Encephalitis Virus Identified by Anti-Idiotypic Antibodies and Virus Affinoblotting" *Intervirol*. 42: 9-16, 1999.
Kornfield and Kornfield, et al., "Assembly of Asparagine-Linked Oligosaccharides" *Ann. Rev. Biochem*. 54: 631-664, 1985.
Krawczynski, et al., "Effect of Immune Globulin on the Prevention of Experimental Hepatitis C Virus Infection" *J. Infect*. Dis. 173: 822-828, 1996.
Lanford, et al., "Analysis of Hepatitis C Virus Capsid, E1, and E2/NS1 Proteins Expressed in Insect Cells" *Virology*. 197: 225-235, 1993.
Lesniewski, et al., "Antibody to Hepatitis C Virus Second Envelope (HCV-E2) Glycoprotein: A New Marker of HCV Infection Closely Associated With Viremia" *J. Med. Virol*. 45: 415-22, 1995.
Livnah, et al., "Functional Mimicry of a Protein Hormone by a Peptide Agonist: The EPO Receptor Complex at 2.8 $\overset{\circ}{\mathrm{A}}$" *Science*. 273:464-471, 1996.

Mahaney, et al., "Genotypic Analysis of Hepatitis C Virus in American Patients" *Hepatology*. 20: 1405-1411, 1994.
Markowitz, et al., "Prophylaxis Against Hepatitis B Recurrence Following Liver Transplantation Using Combination Lamivudine and Hepatitis B Immune Globulin" *Hepatology*. 28: 585-589. 1998.
Matsuura, et al., "Processing of E1 and E2 Glycoproteins of Hepatitis C Virus Expressed in Mammalian and Insect Cells" *Virology*. 205: 141-150, 1994.
Mattioli, et al., "Mimicry of the Immunodominant Conformation-Dependent Antigenic Site of Hepatitis A Virus by Motifs Selected from Synthetic Peptide Libraries" *J. Virology*. 69: 5294-5299, 1995.
Meola, et al., "Derivation of Vaccines From Mimotopes" *J. Immunol*. 154: 3162-3172, 1995.
Meunier, et al., "Analysis of the glycosylation sites of hepatitis C virus (HCV) glycoprotein E1 and the influence of E1 glycans on the formation of the HCV glycoprotein complex" *J. Gen. Virol*. 80: 887-896, 1999.
Mondelli, et al., "Significance of the Immune Response to a Major, Conformational B-Cell Epitope on the Hepatitis C Virus NS3 Region Defined by a Human Monoclonal Antibody" *J. Virol*. 68: 4829-4836, 1994.
Moradpour, et al., "Characterization of Three Novel Monoclonal Antibodies Against Hepatitis C Virus Core Protein" *J Med. Virol*. 48: 234-241, 1996.
Morita, et al., "Detection of Hepatitis C virus RNA in Circulating Immune Complexes by RT-PCR" *Hapato-Gastroenterology*. 43: 582-585, 1996.
Nakabayashi, et al., "Growth of Human Hepatoma Cell Lines with Differentiated Functions in Chemically Defined Medium" *Cancer res*. 42: 3858-3863, 1982.
Perkins, et al., "Parameters to enhance human hybridoma formation with hypoosmolar electrofusion" *Hum. Antibod. Hybridomas* 2: 155-159, 1991.
Phillips, et al., "Enhanced antibody response to liposome-associated protein antigens: preferential stimulation of IgG2a/b production" *Vaccine*, 10:151-158, 1992.
Piazza, et al., "Sexual Transmission of the Hepatitis C virus and Efficacy of Prophylaxis With Intramuscular Immune Serum Globulin" *Arch Intern Med*. 157: 1537-1544. 1998.
Pileri, et al., "Binding of Hepatitis C Virus to CD81" *Science*. 282: 938-941, 1998.
Plaisant, et al., "Human monoclonal recombinant Fabs specific for HCV antigens obtained by repertoire cloning in phage display combinatorial vectors" *Res. Virol*. 148-169, 1997.
Puntoriero, et al., "Towards a solution for hepatitis C virus hypervariability: mimotopes of the hypervaribale region 1 can induce antibodies cross-reacting with a large number of viral variants" *EMBO Journal*. 17: 3521-3533, 1998.
Ralston, et al., "Characterization of Hepatitis C Virus Envelope Glycoprotein Complexes Expressed by Recombinant Vaccinia Viruses" *J. Virology*. 67: 6753-6761, 1993.
Reineke, et al., "A synthetic mimic of a discontinuous binding site on interleukin-10" *Nature Biotechnology*. 17: 271-275, 1999.
Rosa, et al., "A Quantitative Test to Estimate Neutralizing Antibodies to the Hepatitis C Virus: Cytofluorimetric Assessment of Envelope Glycoprotein 2 Binding to Target Cells". *Proc. Natl. Acad. Sci. USA*, 93: 1759-1763, 1996.
Sato, et al., "Demonstration of Sugar Moiety on the Surface of Hepatitis C Virions Recovered from the Circulation of Infected Humans" *Virology*. 196: 354-357, 1993.
Schwartz, et al., "High-resolution Autoreactive Epitope Mapping and Structural Modeling of the 65 kDa Form of Human Glutamic Acid Decarboxylase" *J. Mol. Biol*. 287: 983-999, 1999.
Seki, et al., "Hemadsorption and Fusion inhibition Activities of Hemagglutinin Analyzed by Vaccinia Virus Mutants" *Virology*. 175: 372-384, 1990.
Shimizu, et al., "Neutralizing Antibodies against Hepatitis C Virus and the Emergence of Neutralization Escape Mutant Viruses" *J.Virol*. 68: 1494-1500, 1994.
Siemoneit, et al., "Isolation and Epitope Characterization of Human Monoclonal Antibodies to Hepatitis C Virus Core Antigen" *Hybridoma*. 13: 9-13, 1994.

Simmonds, et al., "Variability of Hepatitis C Virus" *Hepatology*. 21: 570-583, 1995.

Spaete, et al., "Characterization of the Hepatitis C Virus E2/Ns1 Gene Product Expressed in Mammalian Cells" *Virology*. 188: 819-830, 1992.

Tafi, et al., "Identification of HCV Core Mimotopes: Improved Methods for the Selection and Use of Disease-Related Phase-Displayed Peptides." *Biol. Chem*. 378: 495-502, 1997.

Takasaki, et al., "Structure-based design and characterization of exocyclic peptidomimetics that inhibit TNFα binding to its receptor" *Nat. Biotech*. 15: 1266-1270, 1997.

Teichmann, et al., "Advances in structural genomics" *Curr. Opin. Struct. Biol*. 9: 390-399, 1999.

Unkeless, et al., "Structure and Function of Human and Murine Receptors for IgG" *Annu. Rev. Immunol*. 6: 251-281, 1998.

Ward, et al., "Stringent Chemical and Thermal Regulation of Recombinant Gene Expression by Vaccinia Virus Vectors in Mammalian Cells" *Proc Natl Acad Sci USA*. 92: 6773 6777, 1995.

Weiner, et al., "Evidence for Immune Selection of Hepatitis C Virus (HCV) Putative Envelope Glycoprotein Variants: Potential Role in Chronic HCV Infections" *Proc. Natl. Acad. Sci. USA*, 89: 3468-3472, 1993.

Xue, et al., "Identification of the cell surface receptor for bovine viral diarrhea virus by using anti-idiotypic antibodies" *J. Gen. Virol*. 74: 73-79, 1993.

Zimmermann, et al., "Efficient hybridization of mouse-human cell lines by means of hypo-osmolar electrofusion" *J. Immunol. Methods*. 134: 43-50, 1990.

\* cited by examiner

HCV E2 proteins detected with mMAb E2G

FIG. 2 Sequences amplified from central region of HCV E2 vaccinia virus clones >hcv-1a3, (Q1a)
CTCAACTGGATTCACCAAAGTGTGCGGAGCGCCCCCCTGTGTCATCGGAGGGGCGGG
CAACAAACACCTT     GCGCTGCCCACTGATTGTTCCGCAAGCATCCGGAAGCCAC
GTACTCTCGGTGCGGGTCCCTGGATTACGCCCAGGTGCCTGGTc >hcv-1b8, (Q1b)
TGGCACAGGGTTCACCAAGAGACGTGTGGGGCCCCCATGTAACATCGGGGGGGTCGG
CAATAAACACCTT     GACTTGCCCCACGGACTGTTCCGGAAGCACCCGAGGCCAC
TTACACCAAAATGTGGTTCGGGGCCTTGGCTGACACCTAGGTGCATAGTt >hcv-2a-25, (Q2a)
CTCCACTGT TTCACCAAAAACTTGGGCGCACCACCCTGCCGCATCAGAGCTGACTT
TAATGCCAGCACggaCCTGCTGTGCCCACGGACTGTTCAGGAAGCATCCTGAAGCCAC
TTACATCAAAATGTGGCTCTGGGCCCctgtgacgccaaagtgcctgata >HVC-2B-1, (Q2b)
TGGGACTGGGTTCACTAAGACATGCGGTGCACCACCTTGCCGCATTAGGAGGGACTG
CAACGGAACCCTcgaCCTATTGTGCCCACAGACTGTTCAGAAAGCACCCAGATACTAC
CTACCTTAAGTGTGGGAGCGGGGCCTTGGTTGACCCCAAATGCATGGTa

FIG. 3A

| Name | Sequences | | | | | | |
|---|---|---|---|---|---|---|---|
| | CTCAACTGGA | TTCACCAAAG | TGTGCGGGAGC | GCCTCCTTGT | GTCATCGGAG | GGGCGGGCAA | |
| HCV-1a | .......... | .......... | .......... | .......... | .......... | .......... | |
| HCV-Q1a-FR | .......... | .......... | .......... | ..C....... | .......... | .......... | |
| HCV-1b | TAGT....G. | ...T..GA.. | ........G. | ..C..C..G. | AA........ | ..G....... | |
| HCV-Q1b-FR | TGGC..A..G | .....GA... | ...C..T.G. | C.C..C..A. | AA........ | ..G....... | TC..T... |
| HCV-2a | ...C..C... | ...A....A. | ...CT..... | A.A..C..C. | CG....TA.. | .G........ | ...TC... |
| HCV-Q2a-FR | ...C...-T. | ........A. | ...A.CT... | A.A......A | CG........ | .......A.. | CT.ACTT. |
| HCV-2b | ...GGG...G | ......GA.. | ...CA..... | A.A......T | CG....TA.GA | AA.ACTA.. | CT.ACTTT. |
| HCV-Q2b-FR | TGGG.....G | ...T..GA.. | ...CA..... | A.A....... | CG....TA.GA | ......ACT. | |

| | CAACACC--- | ---CTGCACT | GCCCCACTGA | TTGCTTCCGC | AAGCATCCGG | ACGCCACATA | |
|---|---|---|---|---|---|---|---|
| HCV-1a | .......... | .......... | .......... | .......... | .......... | .......... | |
| HCV-Q1a-FR | ......T...G.. | .......... | .......... | ..T....... | ....C.C... | ....A...G. | |
| HCV-1b | .CG....... | ...T..AT.. | ......G... | .......... | ....C.C... | ...G.T..T. | |
| HCV-Q1b-FR | T......... | ...T..ACT. | ......G... | .....C.... | .......T.. | ...G....T. | |
| HCV-2a | TGC..G ATG GACT..TTG. | .......... | ......G... | .....C..T. | ...TA.G... | ......TA..C. | |
| HCV-Q2a-FR | TGC..G ACG GAC...TG. | .......... | ......G... | .....C..T. | ...A.G.T.. | ....A...T. | |
| HCV-2b | .G...TATC GATT.ATTG. | .......... | ......A... | .....C..T. | ...TA.G.C. | A....T..C. | |
| HCV-Q2b-FR | .GGA....CTC GAC..ATTG. | .......... | ......A... | .....C..T. | .....A.A.C. | A.....TA.T.C. | |

```
Name          Sequences
HCV-1a        CTCTCGGTGC GGCTCCGGTC CCTGGATCAC ACCCAGGTGC CTGGTC
HCV-Q1a-FR    ..A.AAAA..T ........T. ........... .....G.... ......
HCV-1b        .A.CAAA..T ...T.G.G.. ......T.G. .......T.. .A..A.
HCV-Q1b-FR    .A.CAAA..T ...T.G.G.. ......T.C.G ........T. A.A..T
HCV-2a        .ATCAAA..T ......T.G. ..........C .....G.A.. .....A.
HCV-Q2a-FR    .ATCAAA..T ......T.G. ..CT.-.G.. .....G.A.A ...A.A
HCV-2b        TCT.AA...T .AG.A.G... ...T..T.A. ..T..T.... ......A
HCV-Q2b-FR    .CT.AA...T .AG.G.G... ...T..T.G. ..C...AA.. A....A
```

One most parsimonious tree found:

```
                              +--HVC-2B-1.C
                          +--7
                          !   +--hcv-2B,
                     +----6
                     !    !   +--hcv-2a-25.
                     !    +--5
              +------4        +--HCV-2A,
              !      !
              !      !        +--hcv-1b8.se
         +----2      +-----3
         !    !              +--HCV-1B,
         !    !
       --1    !
         !    +-----------------HCV-Q1a
         !
         +---...
```

FIG. 3B

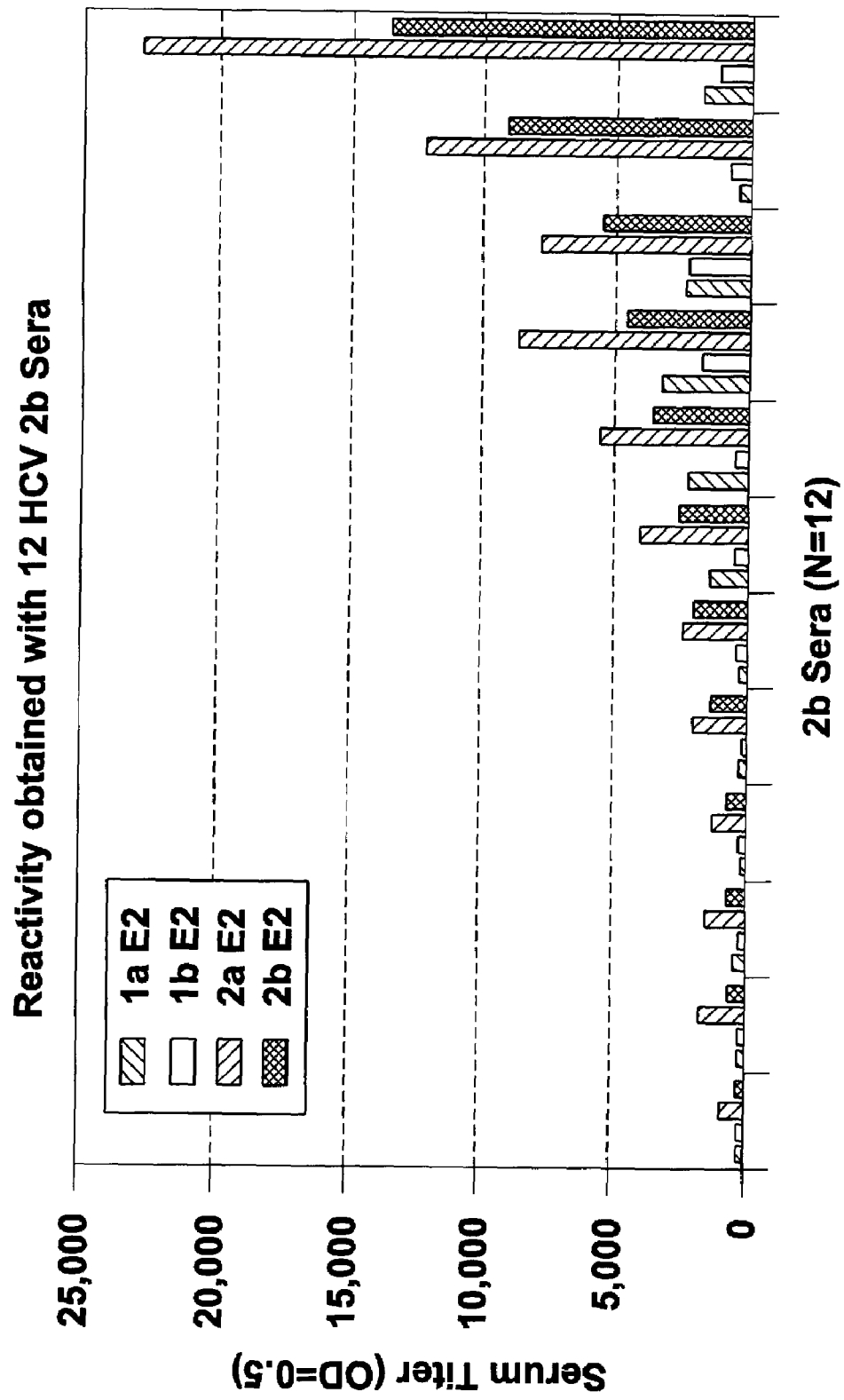

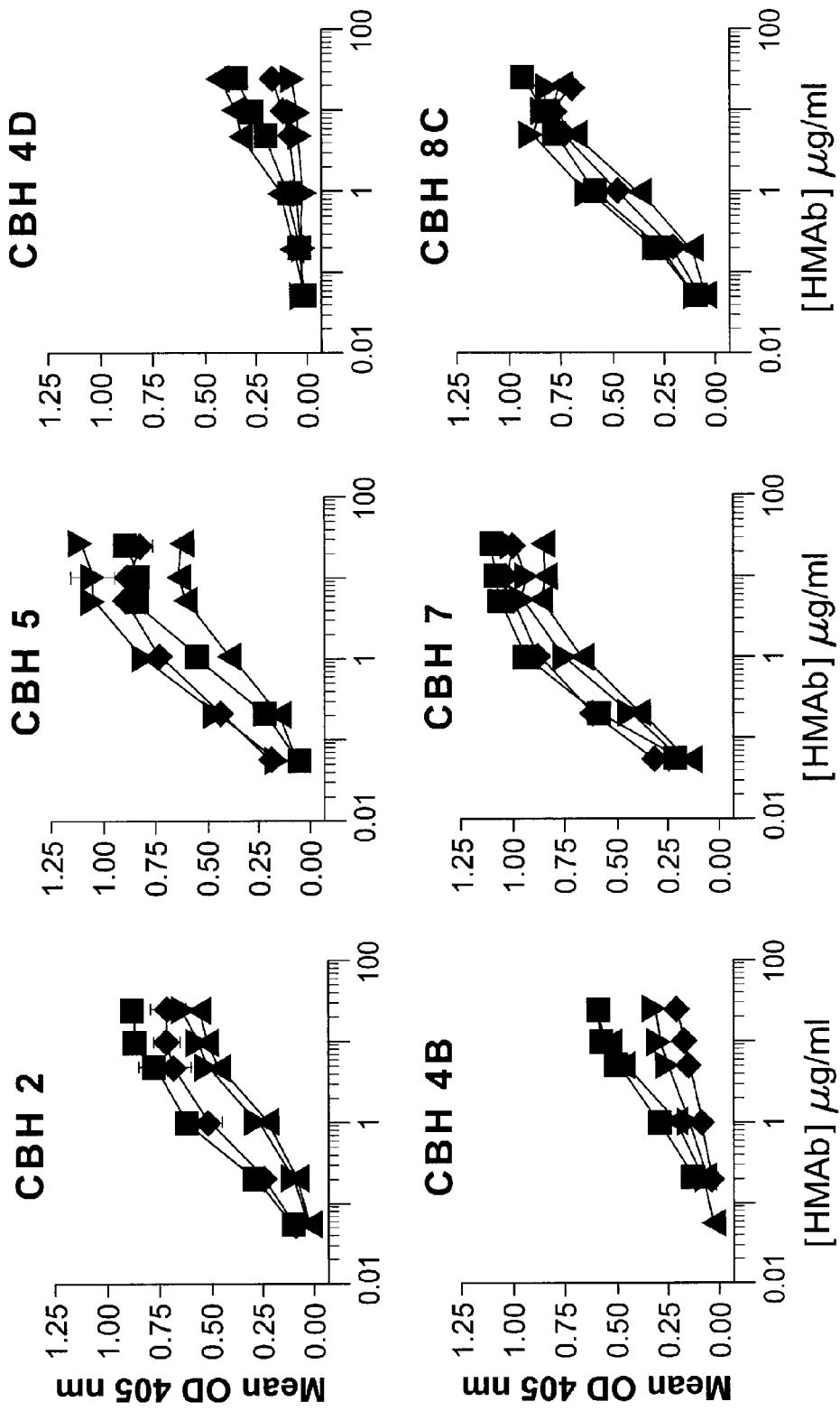

FIG. 14 Binding to CD81-E2 complex

- Coat plates with GNA lectin
- Capture full-length intracellular E2 onto microtiter plate by binding CHO moieties to GNA lectin
- Mix competing HMAb with GNA-captured E2
- Add biotinylated test HMAb. Detect binding of biotinylated test HMAb to E2 with streptavidin-AP conjugate
- Inhibition of binding of test HMAb suggests epitopes within same antibody binding domain

FIG. 22A

Summary of HMAb Competition Analysis

| Competitor Grp | HMAb | E2 | GROUP I | | | | GRP II | GROUP III | | |
|---|---|---|---|---|---|---|---|---|---|---|
| | | | CBH 2 | CBH 5 | CBH 8C | CBH 11 | CBH 7 | CBH 4G | CBH 4B |
| I | CBH 2 | 1a | 18 | 39 | 51 | ND | 93 | 66 | 76 |
| | | 1b | 17 | 50 | 50 | 48 | 91 | 84 | 84 |
| | CBH 8E | 1a | 13 | 39 | 48 | ND | 79 | 63 | 80 |
| | | 1b | 23 | 45 | 57 | 51 | 91 | 87 | 78 |
| | CBH 5 | 1a | 17 | 9 | 22 | ND | 71 | 60 | 74 |
| | | 1b | 4 | 7 | 24 | 9 | 77 | 76 | 80 |
| | CBH 8C | 1a | 27 | 48 | 25 | ND | 85 | 74 | 84 |
| | | 1b | 11 | 23 | 33 | 23 | 84 | 87 | 86 |
| | CBH 11 | 1a | 96 | 93 | 84 | ND | 97 | 72 | 87 |
| | | 1b | 24 | 25 | 43 | 25 | 82 | 97 | 83 |
| II | CBH 7 | 1a | 40 | 42 | 45 | ND | 2 | 251 | 11 |
| | | 1b | 104 | 104 | 89 | 92 | 2 | 146 | 36 |

FIG. 22B

| | | 60 | 63 | 108 | ND | 0 | 1 | 2 |
|---|---|---|---|---|---|---|---|---|
| | XTL U68 | 1a | | | | | | |
| | | 1b | | | | | | |
| | XTL U68 | 60 | 63 | 108 | ND | 0 | 1 | 2 |
| | | 39 | 57 | 73 | 66 | 0 | 23 | 9 |
| III | CBH 4G | 107 | 95 | 85 | ND | 112 | 40 | 68 |
| | | 87 | 83 | 81 | 87 | 114 | 40 | 44 |
| | CBH 4B | 92 | 92 | 87 | ND | 85 | 24 | 29 |
| | | 78 | 93 | 66 | 81 | 63 | 34 | 13 |
| | CBH 4D | 98 | 86 | 90 | ND | 135 | 37 | 58 |
| | | 91 | 82 | 76 | 87 | 102 | 45 | 37 |
| IV | CBH 17 | 94 | 87 | 87 | ND | 114 | 102 | 103 |
| | | 73 | 101 | 88 | 95 | 92 | 89 | 64 |
| C | R04 | 98 | 91 | 92 | ND | 101 | 92 | 98 |
| | | 96 | 104 | 104 | 101 | 99 | 120 | 101 |

Scale: >140% | 60% - 140% | 30% - 59% | 10% - 29% | <10%

Results are the mean percent binding of test antibody relative to wells without any competing antibody. Results are the mean values obtained from 2-5 separate experiments. Both genotype 1a and 1b E2 proteins were tested. ND = not done.

FIG. 23

HCV E2 Deletion Constructs

HCV E2 Deletion Constructs are efficiently expressed

FIG. 25A
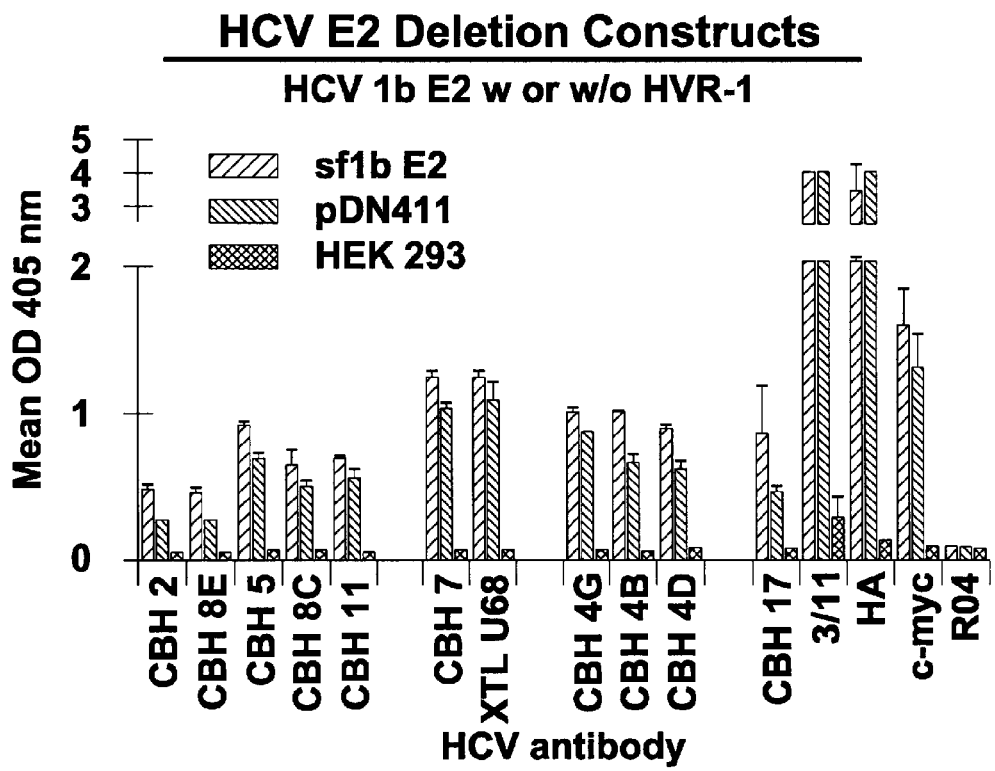
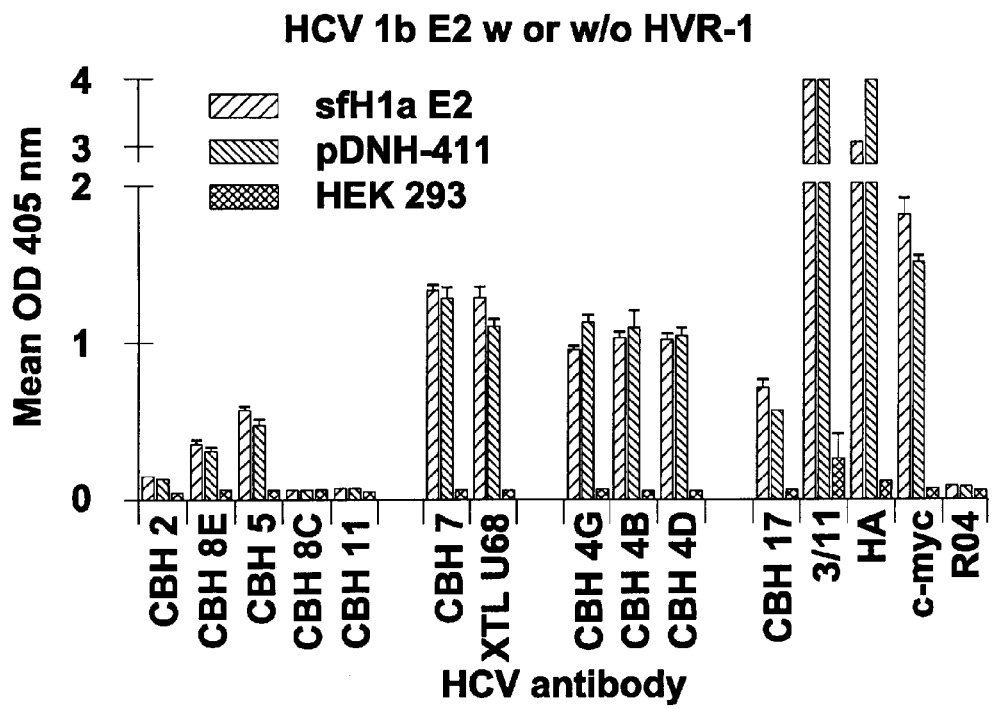

FIG. 25B
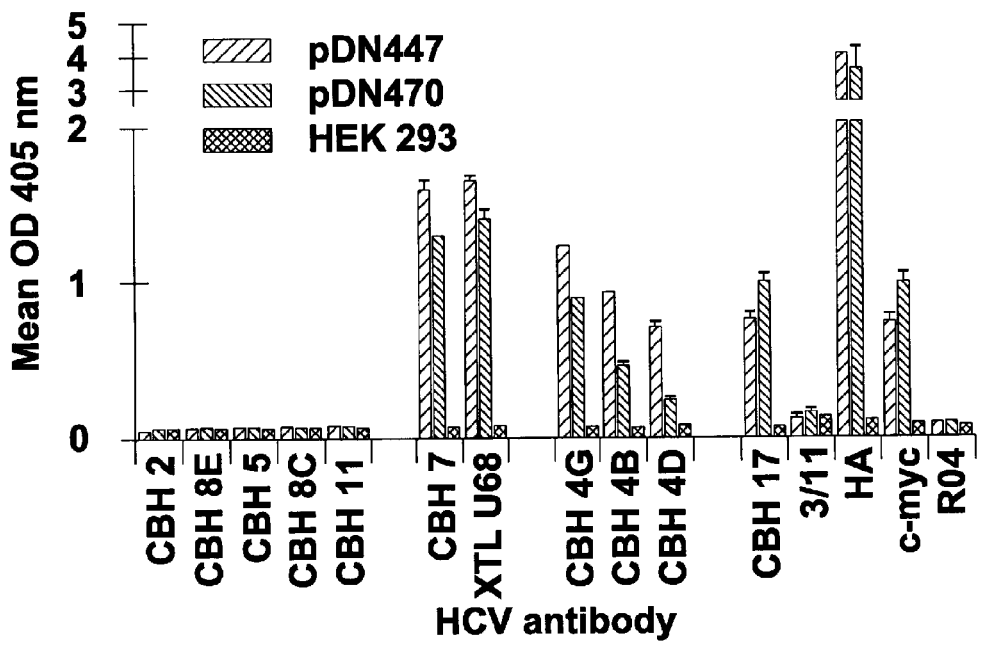
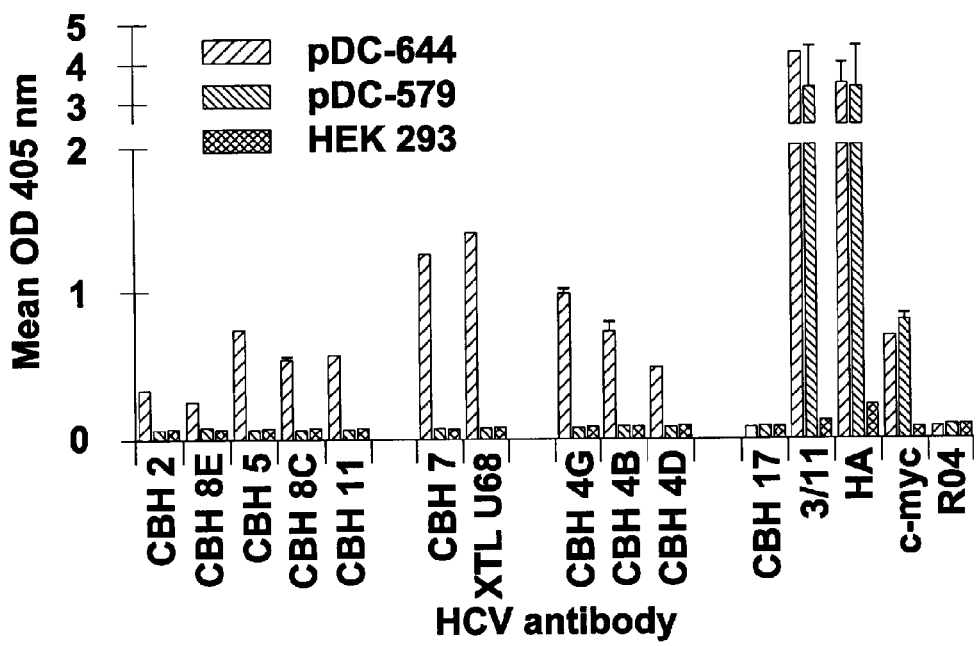

FIG. 26
HCV sera have variable levels of antibodies that inhibit CBH-2 & CBH-7
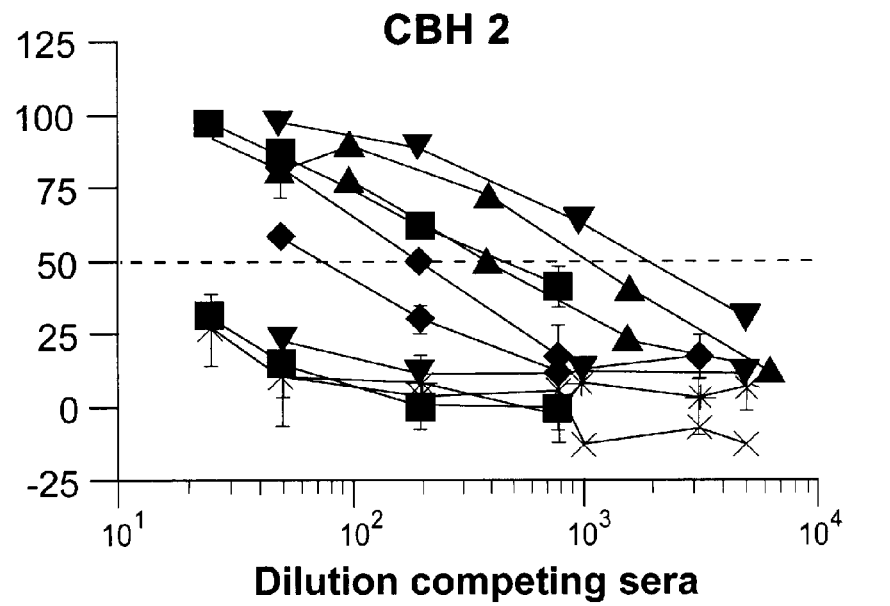
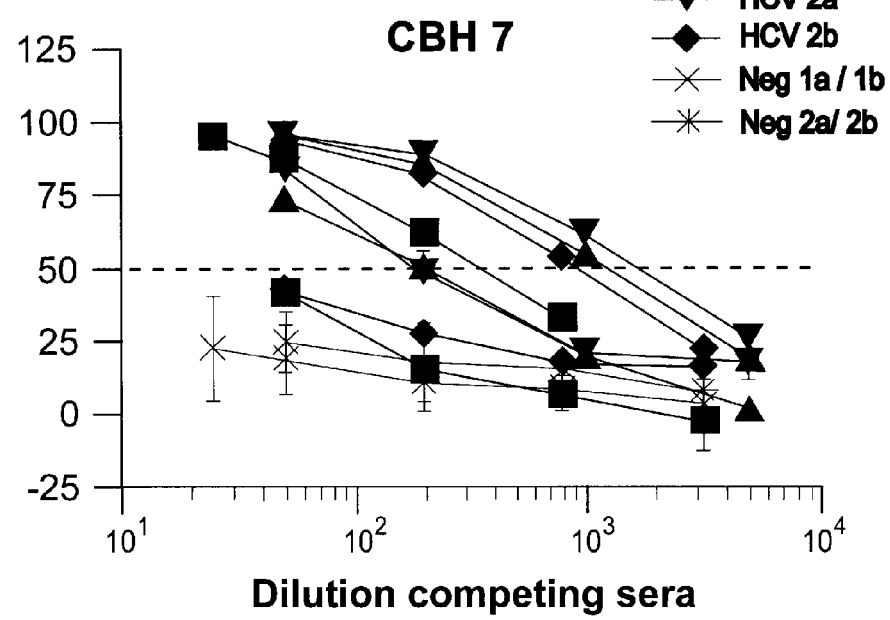

HCV sera have variable levels of antibodies that inhibit CBH-2 & CBH-7

Series of E1 deletions:

| E1 deletion constructs | Position of N-terminal amino acid | Position of C-terminal amino acid |
|---|---|---|
| E1-1 | 192 | 321 |
| E1-2 | 192 | 340 |
| E1-3 | 192 | 352 |
| E1-4 | 192 | 366 |
| E1-5 | 192 | 370 |
| E1-F | 192 | 383 |

E1E2 constructs:

| | | |
|---|---|---|
| E2$_{661}$ | 192 | 661 |
| E2$_{746}$ | 192 | 746 |

FIG. 31

Sequences

| Name | | | | | | | |
|---|---|---|---|---|---|---|---|
| | 200 | 210 | 220 | 230 | 240 | 250 | |
| ZYK-E1 | YEVRNVSGV | YHVTNDCSNS | SIVYEAADMI | MHTPGCVPCV | REGNTSRCWV | ALTPTLAARN | |
| HPCJ491 | ........I. | ........ | .......V. | .......... | ......S... | .......... | |
| HPCST90 | .Q...S..L. | ......P.. | ...A..L... | .......... | .S........ | ..V..V.T.D | |

| | 260 | 270 | 280 | 290 | 300 | 310 | |
|---|---|---|---|---|---|---|---|
| ZYK-E1 | ASVPTAAIRR | HIDLLVGTAT | FCSAMYVGDL | CGSVFLVSQL | FTFSPRRHHT | VQDCNCSIYP | |
| HPCJ491 | ....TT.... | ...V...... | .......... | ....I..... | .......E.. | .......... | |
| HPCST90 | GKL..TQL.. | ......S... | ...L..L... | .......G.. | .....W.... | ..T.....T. | |

| | 320 | 330 | 340 | 350 | 360 | 370 | |
|---|---|---|---|---|---|---|---|
| ZYK-E1 | GHVTGHRMAW | DMMMNWSPTA | ALVVSQLLRI | PQAVMDMVAG | AHWGVLAGLA | YYSMAGNWAK | |
| HPCJ491 | ..S....... | .......T.. | .......... | ....V..... | .......... | .......V.. | |
| HPCST90 | ..I...V... | .......... | ...A...I.. | .....I.... | .......I.. | ...F..V... | |

| | 380 |
|---|---|
| ZYK-E1 | VLIVMLLFAG VDG |
| HPCJ491 | ...A...... ... |
| HPCST90 | ..V.L..... ..A |

FIG. 35

Immunoreactivity of E1 and E1E2 constructs to human antibodies in HCV positive serum

| Sample | E1-321 (1) | E1-340 (2) | E1-352 (3) | HCV E1 CONSTRUCTS E1-366 (4) | E1-370 (5) | E1-383 (FL) | E1+E2-661 | 293 Cells |
|---|---|---|---|---|---|---|---|---|
| TYPE 1b SAMPLES | | | | | | | | |
| J46312(JB) | + | 0 | + | 0 | + | 0 | + | 0 |
| 2746 | + | + | + | + | + | + | + | 0 |
| 2680 | + | + | + | + | + | + | + | 0 |
| 2527 | 0 | 0 | 0 | 0 | 0 | 0 | + | 0 |
| 2221 | 0 | + | + | + | + | + | + | 0 |
| 884 | + | + | + | + | 0 | 0 | + | 0 |
| 2572 | + | + | + | + | + | + | + | 0 |
| 2260 | + | + | + | + | + | 0 | + | 0 |
| 2580 | 0 | + | + | + | + | + | + | 0 |
| 2992 | + | + | + | + | + | 0 | + | 0 |
| 2757 | 0 | + | + | + | + | + | + | + |
| HC04 | + | 0 | 0 | 0 | 0 | 0 | + | 0 |
| HC07 | 0 | 0 | + | 0 | 0 | 0 | + | 0 |
| HC10 | + | + | + | + | + | + | + | 0 |
| HC15 | + | + | + | + | + | + | + | 0 |
| HC26 | + | + | + | + | + | + | + | 0 |
| HC29 | + | + | + | + | + | + | + | 0 |
| | 12/17 (70%) | 12/17 (70%) | 14/17 (82%) | 12/17 (70%) | 13/17 (76%) | 9/17 (53%) | 17/17 (100%) | 1/17 (6%) |
| TYPE 1a SAMPLES | | | | | | | | |
| 1847 | 0 | 0 | 0 | 0 | 0 | 0 | + | 0 |
| 2234 | 0 | + | + | 0 | + | 0 | + | 0 |
| 2290 | + | + | + | 0 | 0 | 0 | + | 0 |
| 2295 | 0 | 0 | 0 | 0 | 0 | 0 | + | 0 |
| 2166 | + | 0 | + | 0 | + | 0 | + | 0 |
| 2021 | 0 | 0 | 0 | + | 0 | 0 | + | 0 |
| HC03 | 0 | 0 | 0 | 0 | 0 | 0 | + | 0 |
| | 2/7 (29%) | 2/7 (29%) | 3/7 (43%) | 1/7 (14%) | 2/7 (29%) | 0/7 (0%) | 7/7 (100%) | 0/7 (0%) |

Notes: * All serum samples tested at 1:40 dilution. * Samples HC04 appears to have anti-cellular antibodies.

FIG.38
E1-352
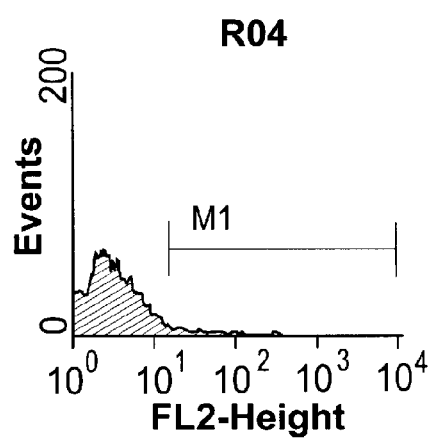
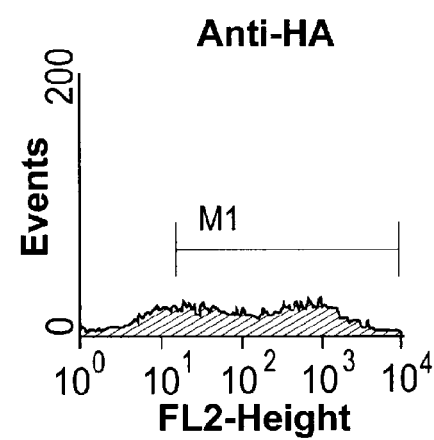
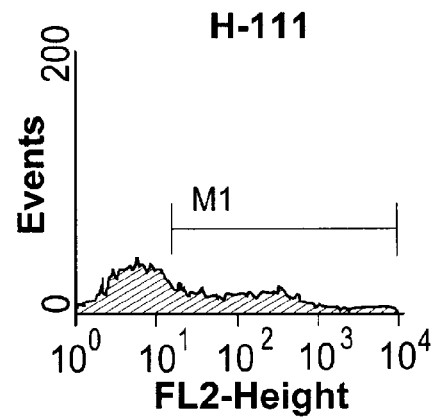
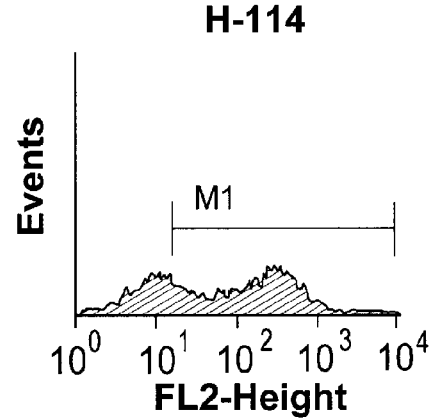

| E1 deletions | | IFA | | |
|---|---|---|---|---|
| | | HA | 111 | 114 |
| E1 (192-370) | ——————————————— | + | + | + |
| E1 (192-366) | ————————————— | + | + | + |
| E1 (192-352) | ———————————— | + | + | + |
| E1 (192-340) | ——————————— | + | + | + |
| E1 (192-321) | ————————— | + | + | + |
| E1 (192-296) | ——————— | + | + | − |
| E1 (192-269) | —————— | + | + | − |
| E1 (192-250) | ———— | + | + | − |
| E1 (192-231) | ——— | + | + | − |
| E1 (192-211) | — | + | + | − |
| E1 (296-321) | — | + | − | − |
| E1 (192-313) | ————————□ | + | + | + |
| E1 (192-305) | □———————— | + | + | − |
| E1 (199-321) | ———————— | + | − | + |
| E1 (206-321) | □——————— | + | − | + |
| E1 (212-313) | ——————— | + | − | − |
| E1 (244-313) | ————— | + | − | − |
| E1 (262-313) | ———— | + | − | − |

FIG. 43A
DCSNSS

Percent of Antibody Bound (0–150), bars for HA and 114:
- ACSNSS
- DASNSS
- DCANSS
- DCSASS
- DCSNAS
- DCSNSA

FIG. 43B
CSIYPGHV

Percent of Antibody Bound (0–400):
- SSIYPGHV
- CSSYPGHV
- CSISPGHV
- CSIYSGHV
- CSIYPSHV
- CSIYPGSV
- CSIYPGHS

| Plasmid | Mutants | HA | IFA & comments | | |
|---|---|---|---|---|---|
| | | | H-114 | H-111 | R04 |
| 107 | E1 WT | + | – | + | – |
| 817 | E1-Cys-226 /A | + | – | + | – |
| 818 | E1-Cys-226 /A | + | – | + | – |
| 821 | E1-Cys-229 /A | + | – | + | – |
| 822 | E1-Cys-229 /A | + | – | + | – |
| 825 | E1-Cys-238 /A | + | – | + | – |
| 826 | E1-Cys-238 /A | + | + | + | – |
| 829 | E1-Cys-272 /A | + | + | + | – |
| 830 | E1-Cys-272 /A | + | + | + | – |
| 833 | E1-Cys-281 /A | + | – | + | – |
| 834 | E1-Cys-281 /A | + | | + | – |
| 837 | E1-Cys-304 /A | + | – | + | – |
| 838 | E1-Cys-304 /A | + | | + | – |

PREVENTION AND TREATMENT OF HCV INFECTION EMPLOYING ANTIBODIES DIRECTED AGAINST CONFORMATIONAL AND LINEAR EPITOPES

CROSS REFERENCE TO RELATED APPLICATIONS

This application is a continuation of and claims priority under 35 U.S.C. §120 to co-pending patent application U.S. Ser. No. 10/958,624, filed Oct. 5, 2004, and published on Aug. 24, 2006 as U.S. Patent Publication 2006/0188511; which is a continuation-in-part of patent application U.S. Ser. No. 10/188,608, filed Jul. 2, 2002, and published on Sep. 25, 2003 as U.S. Patent Publication 2003/180284, now abandoned; which is a continuation-in-part of U.S. Ser. No. 09/728,720, filed Dec. 1, 2000, and issued on Aug. 15, 2006 as U.S. Pat. No. 7,091,324; which is a continuation-in-part of U.S. Ser. No. 09/430,489, filed Oct. 29, 1999, and issued on Feb. 17, 2004 as U.S. Pat. No. 6,692,908; which is a continuation-in-part of patent application U.S. Ser. No. 09/187,057, filed Nov. 5, 1998, now abandoned. Each of these applications is incorporated herein by reference.

FEDERALLY-SPONSORED RESEARCH OR DEVELOPMENT

This invention was made with Government support under contracts AI047355, DA006596, and AI047355 awarded by the National Institutes of Health. The Government has certain rights in this invention.

INTRODUCTION

Technical Field

The field of this invention is related to the preparation of human monoclonal antibodies (HMAb) to structurally conserved epitopes of HCV. Such antibodies can be found in a high proportion of patients and are useful, for example, in the diagnosis and therapy of HCV infection, including being useful in the identification of patients expected to benefit from certain therapeutic strategies.

Background

Hepatitis C virus (HCV) is an enveloped virus the genetic information for which is encoded in a 9.5 kb positive strand RNA genome. A highly conserved noncoding region of 341 bp is localized at the 5'-end of this viral genome, which is followed by a long open-reading frame coding for a polyprotein of approximately 3,010 amino acids. Two putative envelope glycoproteins E1 (gp35) and E2 (gp72) have been identified with 5 or 6 and 11 N-linked glycosylation sites, respectively. A high level of genetic variability is associated with the envelope genes. This variability is highly accentuated at the 5'-end of the E2 gene, where two hypervariable regions termed HVR1 and HVR2, have been described. Antibodies to HVR1 appear to mediate virus neutralization in cell culture and chimpanzee protection studies (Farci et al., 1996 *Proc. Natl. Acad. Sci. USA* 93:15394-15399; Shimizu et al., 1994 *J. Virol.* 68:1494-1500; each of which is incorporated herein by reference). Unfortunately, antibodies to HVR1 tend to be isolate specific and over time drive the replication of new viral variants that the existing immune response does not recognize (Farci et al., 1994 *Proc. Natl. Acad. Sci. USA* 91:7792-7796; Weiner et al., 1992 *Proc. Natl. Acad. Sci. USA* 89:3468-3472; Kato et al., 1993 *J. Virol.* 67:3923-3930; each of which is incorporated herein by reference), although progress has been made at inducing a broader immune response to HVR1 related sequences (Puntoriero et al., 1998 *EMBO Journal* 17:3521-3533; incorporated herein by reference). HCV envelope antigens appear to be highly immunogenic when expressed in glycosylated forms (da Silva Cardoso et al., 1997 *Ann. Hematol.* 74:135-7; incorporated herein by reference). Preliminary data suggest the existence of conserved epitopes within the E2 protein (Lesniewski et al., 1995 *J. Med. Virol.* 45:415-22; incorporated herein by reference). The existence of neutralizing antibodies in serum from infected patients has been proposed.

Studies using HCV E1-E2 proteins expressed in mammalian cells have shown that infected individuals have an antibody response to HCV E2 composed in part to epitopes that are both conformational and linear in nature (Harada et al., 1994 *J. Gen. Virol.* 76:1223-1231; incorporated herein by reference). Studies involving the isolation of human monoclonal or recombinant antibodies to HCV E2 protein showed that a substantial fraction of these antibodies recognize conformational epitopes (da Silva Cordoso et al., 1998 *J. Med. Virol.* 55:28-34; each of which is incorporated herein by reference). As to biological function of these domains, investigators have employed surrogate assays to provide insights into virus neutralization since the virus cannot be grown, in vitro (Houghton, Hepatitis C viruses. In Fields, Knipe, Howley (eds) *Virology*. Lippincott-Raven, Philadelphia, pp. 1035-1058; incorporated herein by reference). One surrogate assay, the neutralization of binding (NOB) assay, evaluates the ability of a given antibody or serum to prevent the association of HCV E2 protein with a human T-cell line (Rosa et al., 1996 *Proc. Natl. Acad. Sci. USA* 93:1759-1763; incorporated herein by reference). The finding that serum antibodies obtained from chimpanzees protected by vaccination were strongly positive in the NOB assay provides support for the relevance of the assay as a measure of virus neutralization activity (Rosa et al., supra; Ishii et al., 1998 *Hepatology* 28:1117-1120; each of which is incorporated herein by reference).

The human tetraspannin cell surface protein CD81 (TAPA-1, for review see Levy et al., 1998 *Ann. Rev. Immunol.* 16:89-109; incorporated herein by reference) is the target protein bound by HCV E2 in the NOB assay (Pileri et al., 1998 *Science.* 282:938-941; incorporated herein by reference). Furthermore, human CD81 binds to free virions, and subsequently is a possible receptor for HCV (Pileri et al., supra). However, little is known about the conservation of the epitopes recognized by the NOB positive antibodies in HCV E2 proteins of different genotypes.

Other approaches to detection of and protection against HCV include the development of peptide mimetics. As an example, peptide mimetics of Hepatitis type A and C viral proteins have been created through production of randomly generated synthetic and phage-display peptide libraries for use in detection assays and vaccination therapies (Mattioli et al., 1995 *J Virology* 69:5294-5299; Prezzi et al., 1996 *J. Immunol.* 156:4504-4513; each of which is incorporated herein by reference). However, effective antibody binding of these mimotopes has only been compared to linearly defined viral epitopes. The sequential recombinant fusing of several linearly defined immunodominant HCV epitopes has been described for use in diagnostic assays (Chein et al., 1999 *J. Clin. Microbiol.* 37:1393-1397; incorporated herein by reference). However, this multiple-epitope fusion antigen designed from linear epitopes was not created to function in the same capacity as a conformational mimetic: It was not designed to interfere with binding to a target receptor.

It is therefore of substantial interest to identify neutralizing antibodies in serum from infected patients, which may be used in diagnosis and passive immunotherapy, where the antibodies would originate from a human cell, and provide for neutralization of a broad spectrum of genotypes, particularly in a particular geographical area. Both breadth of reactivity to multiple HCV genotypes and the ability to interfere with the binding of HCV virions to susceptible cells would be key attributes for a therapeutically useful neutralizing antibody. Also of interest is the design of peptide and non-peptide (organic) structural mimetics of HCV envelope proteins.

Relevant Literature

References providing background information concerning HCV include Abrignani 1997 Springer *Semin. Immunopathology* 19:47-55; Simmonds, 1995 *Hepatology* 21:570:583; and Mahaney et al., 1994 *Hepatology* 20:1405-1411; each of which is incorporated herein by reference.

Deleersnyder et al., 1997 *J. of Virology* 71:697-704 describe an E2 reactive monoclonal antibody. Other references related to the use of antibodies to HCV include Akatsuka, et al., 1993 *Hepatology* 18:503-510; DeLalla, et al., 1993 *J. Hepatol.* 18:163-167; Mondelli, et al., 1994 *J. Virol.* 68:4829-4836; Siemoneit, et al., 1994 *Hybridoma* 13:9-13; and Moradpour, et al., 1996 *J. Med. Virol.* 48:234-241; for producing human antibodies, Foung, et al., 1990 *J. Immunol. Methods* 70:83-90; Zimmermann, et al., 1990 *J. Immunol. Methods* 134:43-50; for producing modified antibodies using combinatorial libraries, Burton and Barbas, Dixon, FJ (Ed.) *Advances in Immunology*, Vol. 57, Vi+391 p. Academic Press, Inc., San Diego, Calif., 191-280, 1994; Plaisant, et al., 1997 *Res. Virol.* 148-169; and Barbas and Burton, *Monoclonal Antibodies from Combinatorial Libraries. Cold Spring Harbor Laboratory Course Manual*, Cold Spring Harbor, N.Y., 1994. Modified antibodies can be produced by mutagenesis followed by in vitro selection for a desirable property, such as increased affinity to a target antigen or broader or narrower specificity. The antibodies can also be modified by a toxin or other bioactive molecule. Of course, antibodies to either E1 or E2 can be produced. Each of the references cited in this paragraph is incorporated herein by reference.

An assay for antibodies binding to HCV E2 is described by Rosa et al., 1996 *Proc. Natl. Acad. Sci. USA* 93:1759-1763; incorporated herein by reference.

Vaccinia virus or baculovirus constructs having a portion of the HCV genome are described by Ralston et al., 1993 *J. Virology* 67:6733-6761 and Lanford et al., 1993 *Virology* 197:225-235; each of which is incorporated herein by reference.

SUMMARY OF THE INVENTION

One aspect of the present invention provides monoclonal antibodies, including human monoclonal antibodies, which bind to the dominant HCV types in major geographical areas. Specifically, a family of monoclonal antibodies binding to conserved conformational and linear epitopes of the HCV E1 and E2 proteins is provided. Among the family are antibodies, which bind to the dominant genotypes found in the United States, so as to be substantially pan-monoclonal antibodies in being able to bind to almost all cases of HCV infection, which have been diagnosed in the United States, as well as at least a substantial proportion of the cases in other geographic locales. The monoclonal antibodies find use in a variety of diagnostic assays. In addition, conserved expression of recombinant HCV E1 and E2 proteins and fragments thereof are provided for use in assays, screening drugs, vaccines, diagnostic assays, and for other purposes. The inventive antibodies find use in passive immunotherapy strategies for reducing viral load of infected individuals and interfering with the infection of target cells. Antibodies recognizing conserved epitopes can also be used to provide a template for the rational design of peptide and conformationally defined epitope mimetics (e.g., organic compounds, organometallic compounds, inorganic compounds, small molecules).

In a particularly preferred embodiment, the inventive antibodies are directed to both conformational and linear epitopes of the E2 or E1 protein of HCV. Conformational and linear epitopes of E2 have been identified using a panel of monoclonal antibodies and a series of deletion constructs of E2. One group of antibodies has been found to bind to conformational epitopes between E2 amino acids 411-644 from HCV 1b. Antibodies of this group have been found to inhibit the interaction of E2 with CD81. Another group of antibodies has been found to bind to conformational epitopes between HCV 1b E2 amino acids 470-644. A third group of antibodies binds to conformational epitopes between HCV 1b E2 amino acids 470-644 but fails to inhibit the binding of E2 to CD81. A fourth group binds to epitopes between HCV 1b E2 amino acids 644-661. A fifth group binds to conformational epitopes between HCV 1b E1 amino acids 230-313. A sixth group binds to a linear HCV E1 epitopes derived from multiple genotypes. In a particularly preferred embodiment, the conformational epitopes to which the antibodies are directed are conserved among HCV strains. The antibodies of the present invention may be combined with pharmaceutically acceptable excipients to provide pharmaceutical formulations.

A further aspect of the present invention is a pharmaceutical composition for the treatment and/or prevention of hepatitis C infection. The pharmaceutical composition of the invention comprises human antibodies capable of binding to the hepatitis C virus envelope glycoprotein E2 and capable of neutralizing HCV infection in vitro and in vivo in an animal model.

In a preferred embodiment of the present invention the anti HCV E2 antibodies comprising the pharmaceutical composition are selected from the group consisting of the human monoclonal antibody (HMAb) CBH-2 which is secreted by the hybridoma cell line deposited in the American Type Culture Collection (ATCC) under Accession no. ATCC PTA-4465, the HMAb CBH-5 secreted by the hybridoma cell line deposited in the ATCC under Accession no. ATCC PTA-4469, and the HMAb CBH-7 secreted by the hybridoma cell line deposited in the ATCC under Accession no. ATCC PTA-4470.

In another embodiment the pharmaceutical composition of the invention may comprise fragments of said antibodies that retain the antigen binding characteristics of the whole antibody, or CBH-2, CBH-5, and/or CBH-7 antibodies produced by recombinant methods that are well known in the art.

Further aspects of the present invention are various prophylactic and therapeutic uses of the anti-HCV monoclonal antibodies. In accordance with this aspect of the invention, pharmaceutical compositions comprising the CBH-2, CBH-5, and/or CBH-7 antibodies may be used for the treatment of chronic hepatitis C patients by administering to such patients a therapeutically effective amount of the antibodies or fragments thereof capable of binding to HCV E2. Those of ordinary skill in the art will appreciate that a therapeutically effective amount is an amount sufficient to achieve one or more particular biological effects. Those of ordinary skill in the art will further appreciate that a therapeutically effective amount may be administered in a single bolus at a single time, or may be distributed over time in multiple individual boluses (of the same or different sizes), or in continuous delivery (at a constant or variable rate). In certain embodiments of the invention, the therapeutically effective amount is an amount effective to achieve one or more desired biological results including, but not limited to: (i) alleviating one or more symptoms of the HCV infection; or (ii) reducing the number of circulating viral particles in an individual or in an individual's liver; or (iii) preventing reemergence or reducing the likelihood of reemergence of one or more symptoms of the HCV infection; or (iv) preventing, or reducing the likelihood of, an increase in the number of circulating viral particles in an HCV-infected individual or in the individual's liver; or (v) any combination of the foregoing. Such pharmaceutical compositions may also be used to prevent or reduce the recurrence of HCV infection. They may be used for example, for passive immunization of recently HCV exposed individuals or of newborn babies born to HCV positive mothers, and for passive immunization of liver transplantation patients to prevent possible recurrent HCV infections in such patients. A "recurrent HCV infection" is reemergence of clinical and/or laboratory evidence of infection, e.g., one or more symptoms of infection or the presence of circulating HCV particles or HCV particles in the subject's liver, in a subject who has been previously infected with HCV but who has received a liver transplant.

A further aspect of the invention is a pharmaceutical composition comprising a therapeutically effective amount of the antibodies of the invention combined with at least one other anti-viral agent as an additional active ingredient. Such agents may include but are not limited to interferons, e.g., interferon alpha-2b, anti-HCV monoclonal antibodies, anti-HCV polyclonal antibodies, RNA polymerase inhibitors, protease inhibitors, ribavirin, IRES inhibitors, helicase inhibitors, immunomodulators, antisense compounds, short interfering RNAs, short hairpin RNAs, RNA aptamers, and ribozymes.

Another aspect of the invention provides definition of conformational epitopes in HCV proteins, and further provided compositions and compounds containing such epitopes. For example, the present invention provides proteins, peptides, and small molecules comprising both conformational and linear epitopes of HCV E1 or E2 protein. The peptides may be deletion constructs such as those in FIG. 23. The peptides may contain one or more epitopes recognized by the antibodies of the present invention. In certain preferred embodiments, the proteins are strings of concatenated peptides at least one of which contains a conformational epitope of HCV. The peptides of the string may contain different conformational or linear epitopes of HCV or the peptides may contain the same epitope. The peptides of the string should preferably fold properly in order to display the conformational epitope substantially as it appears in nature. Such proteins and peptides may be used in formulating vaccines or used in diagnostic tests.

The present invention also provides a method for stratifying patients based on their immunological response to HCV and of identifying those patients likely to respond well to HCV immunotherapy. For example, a patient's serum may be used to test for the presence of antibodies directed against a particular epitope of HCV. If the patient does not have adequate levels of antibodies directed to such an epitope, human monoclonal antibodies directed against the epitope may be administered to the patient.

DEFINITIONS

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Antibody": The term antibody refers to an immunoglobulin, whether natural or wholly or partially synthetically produced. All derivatives and fragments thereof, which maintain specific binding ability, are also included in the term. The term also covers any protein having a binding domain, which is homologous or largely homologous to an immunoglobulin-binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

"Peptide": According to the present invention, a "peptide" comprises a string of at least three amino acids linked together by peptide bonds. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-douridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g. via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

BRIEF DESCRIPTION OF THE DRAWING

FIG. 22 shows the results of a human monoclonal competition analysis. Results are the mean percent binding of test antibody relative to wells without any competing antibody. Results are the mean values obtained from 2-5 separate experiments. Both genotype 1a and 1b E2 proteins were tested. ND=not done.

Figure 23:
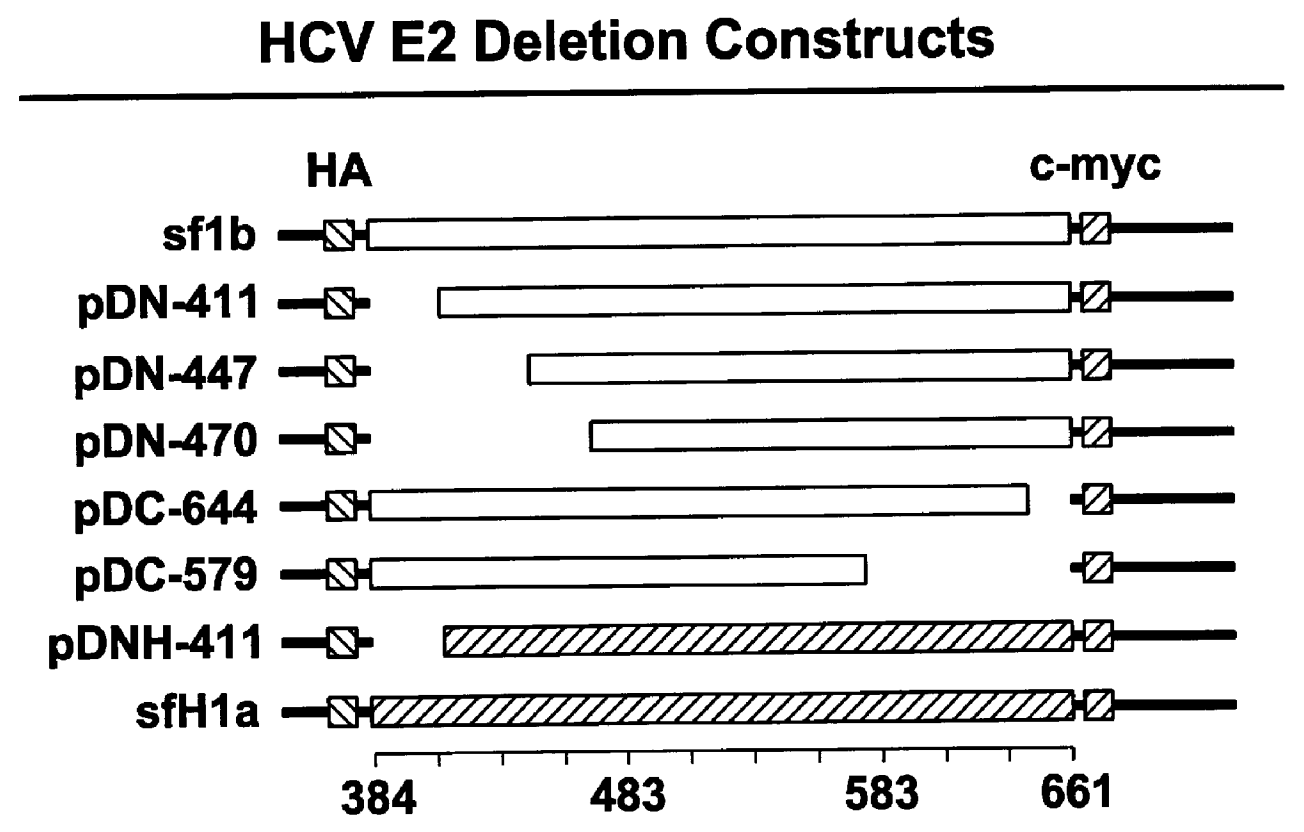

FIG. 23 depicts HCV E2 deletion constructs described herein. The names of the E2 constructs are provided at left. Sequences derived from the vector pDisplay are indicated as solid black bars. The positions of the HA epitope and the c-myc epitope present in the pDisplay vector are also indicated. Sequences derived from HCV 1b E2 are indicated as white boxes. Sequences derived from HCV 1b E2 are indicated as light gray boxes. Numbering of the X-axis (below) is according to the polyprotein of the HCV-1 isolate.

FIG. 25 shows reactivity of certain inventive human monoclonal antibodies with the various HCV E2 deletion constructs. HEK-293 cells were mock transfected (white bars) or transfected with the indicated HCV E2 constructs (see keys each graph). Twenty four hours post transfection cytoplasmic extracts were prepared and equivalent aliquots were captured onto GNA lectin coated microtiter plates as described above. The captured E2 proteins were then incubated with the indicated HCV HMAb (x-axis) and the amount of bound antibody was determined. Bars represent the mean absorbance value obtained from duplicate wells. Error bars indicate one standard deviation from the mean.

FIG. 26 shows graphs demonstrating that sera from HCV infected individuals have variable levels of antibodies that inhibit CBH-2 and CBH-7. Homologous HCV E2 proteins were captured onto wells and incubated with the increasing dilutions of HCV 1a, 1b, 2a, or 2b sera. Values are the specific inhibition of binding of biotinylated CBH-2 or CBH-7 obtained with individual sera. The mean percent inhibition (y-axis) obtained from duplicate determinations at a given dilution (x-axis) is plotted. The mean specific inhibition obtained for eight negative sera are also presented (genotypes of E2 proteins employed are indicated). Error bars on negative sera indicate one standard deviation from the mean.

FIG. 31 shows an alignment of amino acid sequences of E1 constructs from HCV E1 1b (ZYK-E1); full-length HCV 1b (HPCJ491); and H isolate of HCV 1a (HPCST90). Conserved amino acids are indicated by dots and numbering is relative to the initiating methionine of the HCV polyprotein.

FIG. 35 is a Table showing the immunoreactivity of E1 and E1/E2 constructs to human antibodies in HCV positive serum.

FIG. 38 shows graphs representing FACScan analysis of HCV HMAbs H-111 and H-114 with E1-1 recombinant protein transiently expressed in HEK-293 cells.

FIG. 43 shows graphs illustrating the effect of point mutations of amino and carboxy terminal regions of HMAb H-114 epitope. A. Mutational analysis of amino acids 206-211. B. Mutational analysis of amino acids 306 to 313.

FIG. 45 is a table showing the results of an alanine scanning experiment on internal E1 cysteine residues.

FIG. 47A: HCV pseudo-particles were pre-incubated before infection of Huh-7 cells with 20 μg/ml saturating concentrations of anti-E2 HMabs. A negative control experiment was performed using a non-specific HMab (RO4). Results are expressed as the percentages of neutralization. FIG. 47B: Saturation studies of virus neutralization with each HMAb.

FIG. 48A is a photograph (x40) of a slice of a liver fragment obtained from an HCV-infected patient. FIG. 48B is a photograph (x40) of a slice of a liver fragment obtained from an HBV-infected patient. The liver slices were stained using CBH-5. Arrows indicate cells specifically stained with the CBH-5 antibody.

DETAILED DESCRIPTION OF CERTAIN PREFERRED EMBODIMENTS OF THE INVENTION

Figure 1:
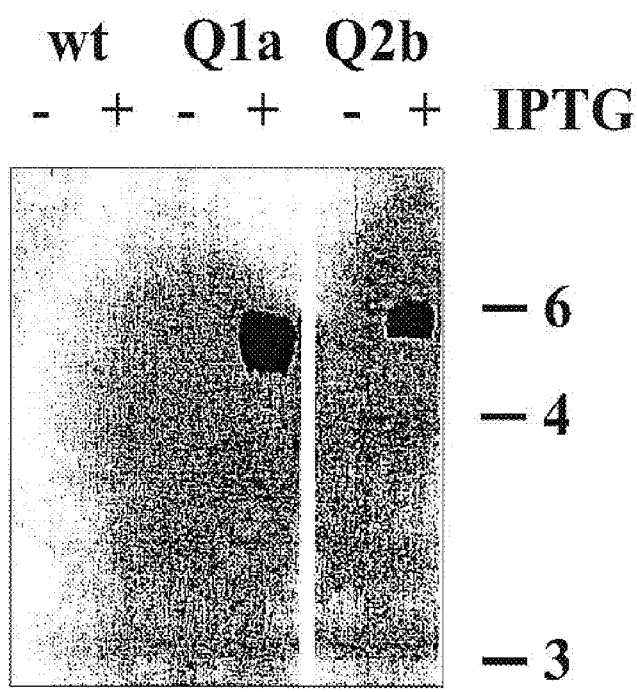
FIG. 1 is a Western blot indicating the expression of HCV E2 proteins by some of the vaccinia virus constructs described in this application. Cytoplasmic extracts were prepared from CV1 cells infected with wild type vaccinia virus and then transfected with pVOTE (wt) or recombinant pVOTE expressing HCV E2 of genotype 1a (Q1a) or 2b (Q2b). Cells were cultured for 24 hours in the presence (+) or absence (−) of the inducer IPTG. Extract corresponding to $2\times10^5$ cells was fractionated by SDS PAGE and blotted onto nitrocellulose. HCV E2 protein was revealed by incubation with 1/500 di detected with 2 µg/ml of biotinylated CBH-2 in the presence of 20 µg/ml of the indicated HMAbs (x axis). The bars indicate the binding observed in the presence of the indicated antibody relative to binding of biotinylated CBH-2 to HCV E2 in the absence of any competing antibody (y axis). R04 is a control HMAb that recognizes a cytomegalovirus protein. Bars indicate the mean value obtained from replicate wells. Error bars indicate one standard deviation from the mean.
Figure 4A:
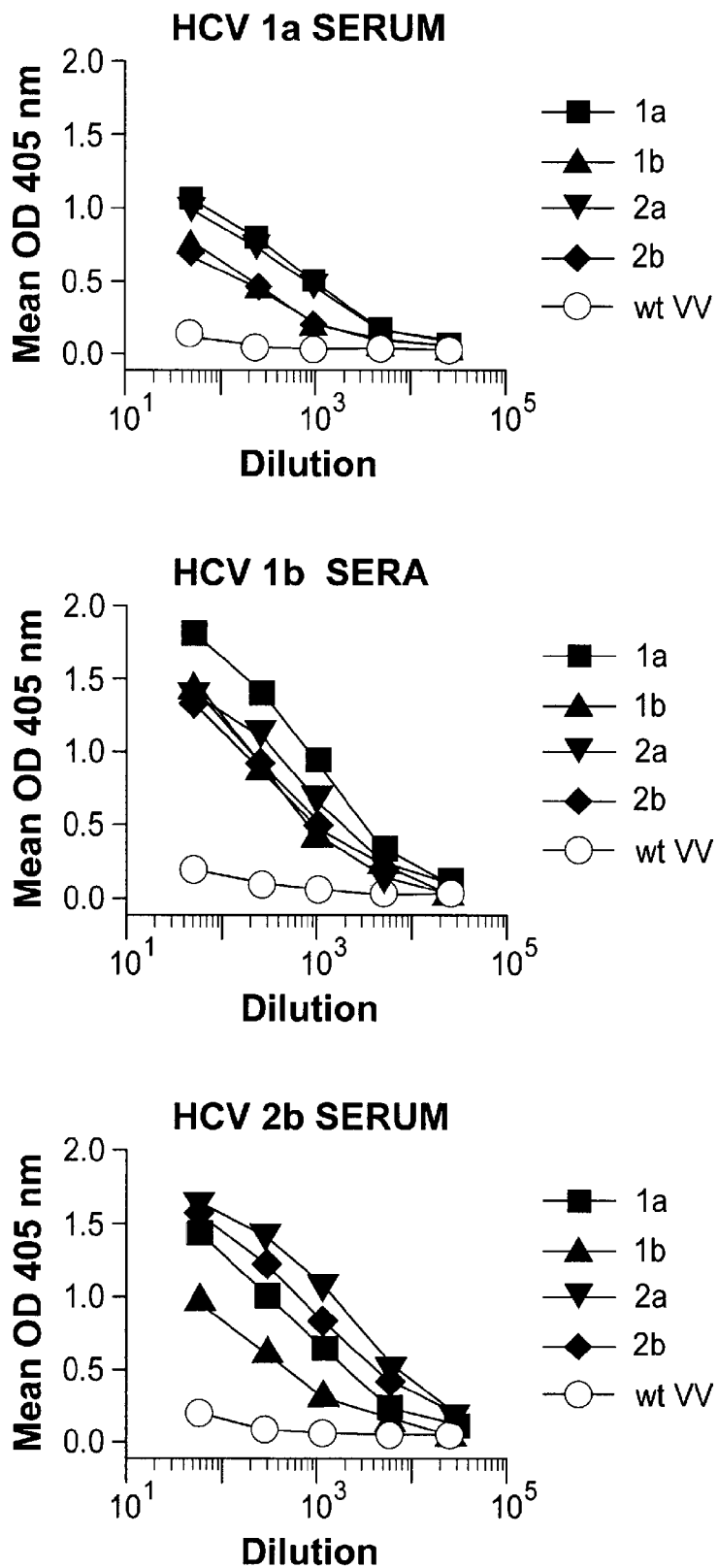
Figure 4B:
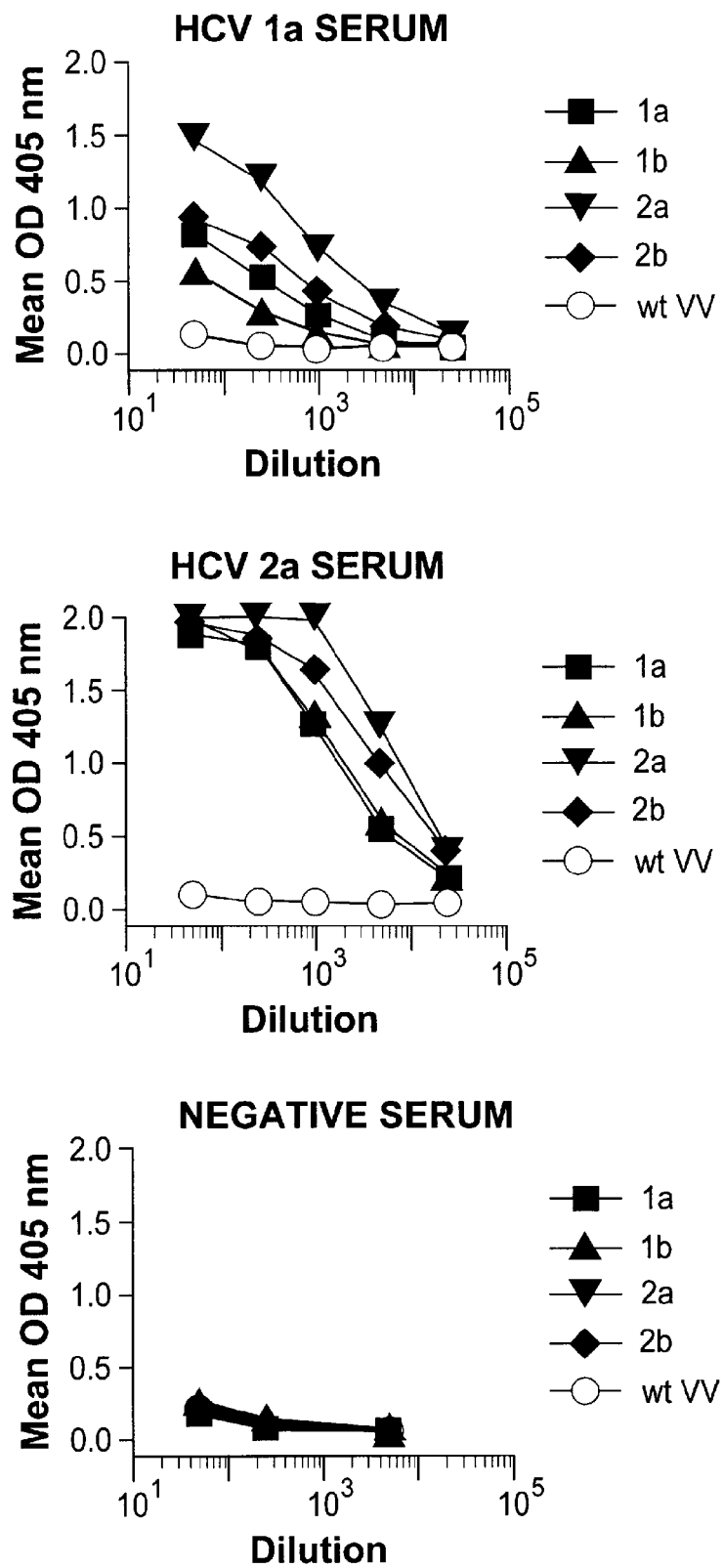

Monoclonal antibodies, particularly human monoclonal antibodies ("HMAbs"), are provided which bind to one or more hepatitis C virus genotypes, which antibodies find use for diagnosis, therapy, and vaccine development. A panel of human monoclonal antibodies (HMAbs) from peripheral B-cells of an individual with asymptomatic HCV infection and having a high serum neutralization of binding titer were produced and characterized. Eleven HMAbs to HCV E2 and two HMAbs to HCV E1 have been produced. One group of antibodies binds to the genotypes 1 and 2 of HCV, while other antibodies bind to fewer than this group of genotypes. HCV genotypes 1 and 2 together are the dominant virus types encountered in the western hemisphere and other geographic locations. The antibodies bind to conformational and linear epitopes, which are conserved across virus types and genotypes. The antibodies binding to HCV E2 proteins of genotypes 1a, 1b, 2a, and 2b and a subset of these antibodies inhibit the interaction of these E2 proteins with human CD81. Additionally, one of two HMAbs to HCV E1 binds to multiple genotypes of HCV.

By virtue of the variety of binding profiles of the antibodies, diagnostic assays may be employed which will detect a plurality of types and genotypes, so as to provide a pan-anti-HCV antibody for HCV encountered in the United States, while at the same time being able to dissect individual genotypes by subtractive analysis. In addition, the antibodies being human may be used for passive immunization, as protective therapy for individuals at risk for HCV or as a therapy for people who are seropositive for HCV.

The HMAbs of the invention offer several advantages over existing HMAbs against HCV. Because non-homologous primary amino acid sequences may still define immunologically identical tridimensional protein structures, HMAbs binding to structurally conserved epitopes can recognize multiple, sequentially divergent HCV genotypes in native conformation, whereas antibodies recognizing only linear or denatured epitopes may not. In particular, conformationally dependent and selected linear-dependent epitopes of anti-HCV E1 or E2 HMAbs may effectively interfere with the interaction of native HCV virus and its cellular target receptors. Using conformationally dependent and selected linear-dependent epitopes of HMAbs to actively interfere with the ability of native HCV virus to bind to target cell receptors such as CD81 has specific therapeutic application for reducing viral load in infected individuals, and preventing infection or re-infection of organs in non-infected individuals (by, e.g., a) recognizing HCV E1 or E2 proteins encoded by different HCV genotypes; b) binding HCV particles; c) preventing attachment and entry of HCV viral particles to their target cells), particularly in recent organ transplant recipients, individuals undergoing renal dialysis, and individuals undergoing treatment for hemophilia or other blood clotting disorders. Other recipients include individuals recently exposed to HCV containing bodily fluids. Both individual HCV HMAbs and a cocktail of several HCV HMAbs recognizing several epitopes may be employed.

Certain subsets of the HMAbs interfere with E2-associated viral infection by mechanisms other than preventing direct interaction with CD81. This subset of antibodies interferes with viral infectivity by a number of possible mechanisms, including preventing E2 binding to co-receptor proteins, conformational changes in E1 and/or E2 proteins necessary for target cell binding, E1 and E2-mediated viral fusion to target cells, and uncoating of HCV virions. Because they bind distinct epitopes, the subset of HMAbs that directly interferes with E2 binding to CD81 complements HMAbs in the subset that interfere with infectivity by other mechanisms for both therapeutic, vaccine, and diagnostic applications.

HMAbs, which recognize viral epitopes and interfere with virus/target receptor interaction, and viral epitopes which bind to such HMAbs, may also serve as templates for rationally designing peptide and other structural mimics of the viral epitopes. Structural molecular mimics defined by these anti-HCV HMAbs find use in their ability to block binding of the native virus to target receptors by binding to the target receptor themselves.

By producing human monoclonal antibodies, it is possible to directly analyze the human immune response to HCV. Importantly, by using human monoclonal antibodies, immune responses against the antibodies themselves as foreign antigens are minimal, whereas vigorous immune responses are generated against monoclonal antibodies produced from non-human sources, because they are recognized as foreign antigens. Selecting for HMAbs that recognize conserved viral conformational epitopes affords broader and more effective therapeutic application of these reagents for ameliorating or preventing HCV infection than antibodies able to bind only linear or denatured epitopes. All previous antibodies described as having the property of preventing HCV infection or uptake into target cells recognize a highly variable sequence of HCV E2 known as the hypervariable region. In contrast, the antibodies described above recognize both conformational and linear epitopes, the majority of which are highly conserved HCV E2 proteins of multiple different genotypes. Thus the antibodies described herein have the advantage that they are active against a much wider range of HCV isolates than previously described neutralizing antibodies. An additional advantage is that the high conservation of the epitopes recognized by the antibodies described herein indicates that these antibodies recognize sequences with functional and/or structural significance within the HCV E1 or E2 protein. Thus peptides or small molecules isolated with these antibodies have a high probability of being targeted to functional regions within HCV E1 or E2. This is not true for other HCV antibodies described to date.

Of the detection antibodies described, CBH-4G has essentially equal reactivity to HCV E2-CD81 complexes of multiple HCV genotypes, whereas CBH-4B recognizes HCV genotypes 1a and 1b. The level of interfering antibodies present in HCV antisera has also been shown to be quite low. Therefore they provide a straightforward means of assaying the level of neutralizing antibodies present in a sample in a microtiter plate format without resorting to multiple flow cytometric analyses.

The overall strategy employed for the development of the subject HMAbs was as follows: (1) individuals with evidence of exposure to HCV were identified; (2) antigen specific B-cells from their peripheral blood were expanded and activated in vitro; (3) these cells were immortalized by electrofusion with a suitable mouse-human heteromyeloma; (4) relevant human antibody secreting hybridomas were identified; and (5) the relevant hybridomas were stabilized by cloning. This strategy resulted in the identification of HMAbs that are specific to the HCV E2 protein, a number of which bound to conformation epitopes of E2 of HCV genotypes 1a and 1b and HCV genotypes 2a and 2b, so as to recognize the primary genotypes encountered in the United States and elsewhere with a single antibody, while others bound to fewer of the indicated genotypes, so as to be useful in identifying an HCV type or genotype. The above strategy also resulted in the identification of HMAbs that are specific to HCV E1 protein, described herein.

As an example, peripheral B cells from an individual with asymptomatic HCV infection and a high serum neutralization of binding titer were used to produce and characterize a panel of human monoclonal antibodies. The initial screening made use of a genotype 1a E2 protein having an amino acid sequence with 98% homology to the same region of the HCV-1 isolate (Lanford et al., 1993 *Virology* 197:225-235; incorporated herein by reference). This step biased the screening approach used to the selection of antibodies to epitopes conserved between genotypes 1a and 1b since the donor was infected with a 1b isolate. All of the HMAbs also reacted with E2 from a heterologous HCV 1b isolate, Q1b, which was 79% homologous with the HCV 1a isolate employed in the selection of HMAbs. Denaturation of recombinant E2 completely abrogated the reactivity of 10 of 11 HCV HMAbs. Thus, the majority of the HMAbs recognized conformational epitopes.

Five HMAbs, CBH-4D, -4B, -4G, -9, and -17, were negative in the NOB assay and reacted with HCV E2-CD81 complexes. Two of these antibodies, CBH-4G and CBH-9, reacted with HCV E2 proteins of genotypes 1a, 1b, 2a, and 2b in both the GNA and CD81 capture assays. The other three antibodies, CBH-4B, -4D, and -17, exhibited restricted reactivity to E2 proteins of genotypes 1a and 1b. HMAbs CBH-4B and CBH-4D have kappa and lambda lights chains, respectively, and probably recognize different epitopes. HMAb CBH-17 was the only antibody to recognize a denaturation insensitive epitope. Thus it is likely that each of the NOB negative antibodies recognizes a distinct epitope.

Six of the HMAbs recognizing conformational epitopes, CBH-2, -5, -7, -8E, and -11, were positive when tested with the neutralization of binding assay using HCV 1a E2 protein. Five of these antibodies HMAbs CBH-2, -5, -7, -8C, and -8E reacted with E2 proteins of all tested genotypes. The same six antibodies failed to bind to E2 of genotypes 1a, 1b, 2a, or 2b when complexed to CD81-LEL. Thus epitopes that partially or fully overlap the CD81 binding site within HCV E2 are both conformational in nature and highly conserved. A high degree of sequence conservation in the CD81 binding site is consistent with the proposition that the interaction between HCV E2 and CD81 is biologically relevant. Two of the four NOB positive antibodies tested, HMAbs CBH-2 and CBH-5 were able to prevent the binding of intact HCV virions to CD81. The HMAbs CBH-7 and CBH-11 did significantly inhibit binding of HCV virions to CD81, despite the antibodies having equivalent activity in the NOB assay. This may reflect the fact that HCV virions are thought to have E1-E2 complexes at their surface, and that not all of the epitopes present in E2 may be exposed in such complexes. Testing of the HMAbs with E1-E2 complexes may shed light on this issue. Alternatively, the differential results in the NOB and virion inhibition assays may reflect differences in the true affinity of the HMAbs for the E2 protein or E1-E2 complexes. In any event, a strong neutralization of binding activity in and of itself does not ensure that an antibody will bind to intact HCV virions. Thus it is probable that not all antibodies inhibiting the interaction of E2 protein with CD81-LEL in vitro will neutralize infectivity in vivo.

Five of these six NOB positive antibodies are to epitopes shared among the five HCV isolates used in this study. The other antibody CBH-11 exhibited differential reactivity to two 1a isolates and probably recognizes an epitope distinct from the other antibodies. Indeed the variable reactivity of CBH-11 to different 1a isolates may have contributed to its negative result in the virion binding experiment. Both the differential reactivity of CBH-2 and CBH-7 with HCV virions and competition experiments indicate that CBH-2 and CBH-7 recognize distinct epitopes. Competition experiments also suggest that the epitopes recognized by HMAbs CBH-5 and CBH-2 are distinct. It remains possible that CBH-2 and CBH-8E recognize the same or very similar epitopes, however. Determining the total number of unique epitopes will require sequencing of the antibody genes produced by the hybridomas as well as competition studies and testing with additional HCV isolates.

Competition analysis (FIG. 22) has been employed to define antibodies with similar binding sites in HCV E2. Seven HMAbs were biotinylated and the binding of the biotinylated antibodies to HCV E2 in the presence of increasing amounts of competing HCV HMAbs was determined. Antibodies that cross-competed significantly were grouped together. Regions of HCV E2 that contained the binding sites were localized using a series of HCV E2 deletion constructs (FIG. 23). Four competition groups were defined. Group I consisted of five HMAbs, CBH-2, -8E, -5, -8C, and -11. Antibodies from this group inhibit binding of HCV E2 to CD81 and recognize conserved epitopes localized to HCV E2 amino acids 411 to 644. Group II consists of HMAbs CBH-7, which recognize a highly conserved epitope located between HCV E2 amino acids 470-644. Antibodies from groups I and II exhibited minimal cross-competition. Group III consisted of three antibodies, CBH-4G, -4B, and -4D, which do not inhibit binding of HCV E2 to CD81 and recognize epitopes between HCV E2 amino acids 470 to 644. Group IV consisted of one antibody, CBH-17, that recognized an epitope located between HCV E2 amino acids 644 to 661. Antibodies in group I and II have been found to inhibit HCV replication in a small animal model and recognize two distinct conserved binding sites outside of the hypervariable region of E2. The low level of competition between antibodies of groups I and II should lead to additive virus neutralization activity and raises the possibility that these antibodies might act synergistically in vivo.

These results indicate that several conformational epitopes within HCV E2 are highly conserved among divergent HCV genotypes. The antibodies that recognize these epitopes are useful as reagents to better define the structure of HCV E2. Furthermore, the antibodies that inhibited binding of HCV virions to human CD81, CBH-2 and CBH-5, are prime candidates to mediate virus neutralization. The absence of a true in vitro model for virus neutralization, however, will require that the fundamental proof be obtained by the ability of selected HMAbs to prevent or modify HCV infection in appropriate animal models. If successful, broadly reactive neutralizing antibodies will likely have therapeutic utility. Analogous to the success achieved with hepatitis B immunoglobulin in liver transplantation (Dickson, 1998 *Liver Transpl. Surg.* 4(5 Suppl 1):S73-S78; Markowitz et al., 1998 *Hepatology* 28:585-589; each of which is incorporated herein by reference), one possible application is to suppress HCV infection in liver transplant recipients with broadly reactive neutralizing human monoclonal antibodies.

The above strategy for isolating HMAbs also resulted in the identification of HMAbs that are specific to the HCV E1 protein. These HMAbs, like the HMAbs to E2, also bound both conformational and linear epitopes of HCV E1. One HMAb to E1 of HCV genotype 1b was identified, H-114. Another antibody to E1, H-111, recognized epitopes from four or more genotypes (genotypes 1a, 1b, 2b, and 3a). This broad specificity is particularly preferred in the diagnostic and therapeutic applications described above. The isolation and characterization of the H-114 and H-111 HMAbs are described in Example 10.

The HMAbs to HCV E1 of the present invention recognize different epitopes than previously identified anti-E1 antibodies. H-114 recognizes a non-linear sequence of amino acids that may include the putative fusion peptide of E1. Since the fusion between the viral envelope and cellular membranes is a critical event in the initiation of virus infection, the H-114 antibody that might interfere with this event and inhibit the HCV life cycle including the steps of cell entry, uncoating, and virion assembly. The antibody H-111 has the unique feature of recognizing individual amino acids across multiple genotypes.

The epitopes recognized by H-111 and H-114 provide new possibilities for virus neutralization. E1 and E2 are believed to interact to form a heterodimeric nonvalent E1-E2 complex that ultimately constitutes the virion envelope. Due to the unique binding activities of H-111 and H-114, these antibodies can be used to gain insights on the interaction of E1/E2 and the formation of mature envelope on virions.

While human monoclonal antibodies are provided, other antibodies from other sources may recognize the same epitopes recognized by the human antibodies described herein, and may also be employed. Generally antibodies from murine sources, mice and rats, lagomorpha and domestic animals find use. One may produce antibodies having the conserved regions of these mammalian sources using genetic engineering and replacing the constant regions of the HMAbs provided herein or may use the proteins to be described below as immunogens for immunizing the animals and then immortalizing the resulting B cells and screening as described below for immortalized cells which produce monoclonal antibodies having analogous broad range binding specificity. By screening in competitive assays with the subject HMAbs, one can determine whether the non-human antibodies bind to the same epitope.

For diagnosis, the antibodies may be used in a variety of ways, for capturing and/or identifying circulating HCV virions, E1 or E2 protein, or anti-E1 or anti-E2. The antibodies may be used for immunotherapy, prophylactic, or therapeutic. The antibodies may also be used for development of vaccines for HCV.

The isolated antibodies are of the IgG class. The following are the designations for the antibodies and the HCV genotypes, which the antibodies recognize. Some of the HMAbs exhibited good affinity for HCV E2 proteins, with the antibodies exhibiting maximal signals at concentrations ranging between 1 to 20 µg/ml. These antibodies are the IgG class, particularly $IgG_{1\kappa}$. The following are the designations for the antibodies and the HCV genotypes, which the antibodies recognize. The below HMAbs exhibited good affinity for HCV E1 or E2 proteins,

TABLE 1

HCV Genotypes bound by HMAbs

| Antibody | Protein bound | Genotypes bound |
| --- | --- | --- |
| CBH-2 | E2 | 1a, 1b, 2a, 2b |
| CBH-4D | E2 | 1a, 1b |
| CBH-4B | E2 | 1a, 1b |
| CBH-4G | E2 | 1a, 1b, 2a, 2b |
| CBH-5 | E2 | 1a, 1b, 2a, 2b |
| CBH-7 | E2 | 1a, 1b, 2a, 2b |
| CBH-8C | E2 | 1a, 1b, 2a, 2b |
| CBH-8E | E2 | 1a, 1b, 2a, 2b |
| CBH-9 | E2 | 1a, 1b, 2a, 2b |
| CBH-11 | E2 | —, 1b, 2a, 2b |
| CBH-17 | E2 | 1a, 1b |
| H-111 | E1 | 1a, 1b, 2b, 3a |
| H-114 | E1 | 1b |

The antibodies may be used in their native form or may be truncated to provide Fab or $F(ab')_2$ fragments. The genes encoding the heavy and light chains may be isolated and modified in a number of different manners. Conveniently, using RT-PCR, the cDNA may be obtained for the genes in a convenient construction for further manipulation. The nucleotide sequences of the variable regions of the heavy and light chains may be isolated and joined, either directly or indirectly or through a chain of 3n nucleotides, where n is at least 1 and not more than about 60, usually not more than about 40, to provide a linker of amino acids between the two variable regions. The length of the chain can be determined empirically to provide the optimum affinity and other properties, e.g., linkage through mercapto, carboxy, or amino groups, for chelation, bonding to a surface or other molecule, or the like. In addition, the genes, intact or portions thereof, including at least the variable regions, may be fused to other sequences to provide for each of attachment to a surface, labels or tags for identification, sequences for affinity isolation, and the like. Any of these reagents can be attached to the antibody with a cleavable arm, e.g., a protease site or chemical linker.

Labels or tags may be attached to the gene encoding the antibody to provide for specific affinity isolation methods for the expressed antibody. The labels or tags may otherwise improve the utility of the isolated antibody gene. Some examples of tags include the biotinylation sequence of *E. coli* biotin carboxylase carrier protein; a sequence of six histidines or a sequence of alternating histidines and aspartic acids that are suitable for allowing binding of the antibody to a column containing immobilized diavalent cations; the sequence of any one of several known high affinity antibody epitopes including the FLAG epitope DYKDDDDK, the T7 tag sequence MASMTGGQMG, the S-tag sequence KETAAAKFERQHMDS, or any other known sequence that confers binding to a specific antibody; a fusion protein partner such as glutatione-S-transferase, streptavidin, or ligands to cell surface receptors found on a desirable cell target; and fluorescent, radioactive, luminescent or enzymatically detectable moieties.

Where labels are polypeptides, the sequence can be directly fused to a gene of one of the antibody chains. In any case, sequences may be provided which provide a site for linking a label, such as cysteines for forming thioethers with maleimide groups, polyhistidine/cysteines or polyhistidines/aspartic acids for chelating metals, which may be bonded to a variety of molecules, polylysines for reacting with aldehydes in reductive animation reactions, etc. Labels may include enzymes, chelating groups, ligands for binding to a ligand binding proteins, e.g., biotin and streptavidin, digoxigenin and antidigoxigenin, etc., green fluorescent protein, and the like. The biotinylation sequence of E. coli biotin carboxylase carrier protein (BCCP) can be used for in vivo biotinylation of proteins expressed in E. coli or introduced in a lysate of E. coli. A sequence of six histidines or a sequence of alternating histidines and aspartic acids that are suitable for allowing binding of the antibody to a column containing immobilized divalent cations can be used. Sequences encoding high affinity epitopes may be employed, such as the FLAG epitope DYKDDDDK (SEQ ID NO: 13), the T7 tag sequence MASMTGGQMG (SEQ ID NO: 14), the S-tag sequence KETAAAKFERQHMDS (SEQ ID NO: 15), or any other sequence that confers high affinity binding to its correlative binding member or a protein reagent. Fusion proteins, besides the ones indicated above, include glutathione-S-transferase, luciferase, ligands to cell surface receptors found on hepatocytes, T-cells or other desirable cellular target, and the like. Such fusions are usually joined via a linker sequence of 3-50 amino acids that promotes the bi-functionality of the protein. These molecules can be linked to the antibodies via cleavable arms (protease sites) or other means. The antibodies may be chemically linked or fused to various toxins, such as diphtheria toxin, ricin, abrin, ribosome inactivating proteins, apoptosis signaling proteins, pore forming proteins, e.g., perforin, and the like. Alternatively, the antibodies may be linked to chelated toxic heavy metals or radioactive isotopes, particularly technetium, radioactive iodine or the like. The antibodies may be chemically linked to fluorophores or chemiluminescent molecules. Chemical coupling may involve biotinylation using the activated carboxylic acid group or biotin-C11-hydroxysuccinimide ester, which will react with cysteines; coupling through the use of CNBr activation of various beads (sepharose, agarose, magnetic, polystyrene, etc.) or surfaces to link the antibodies, and the like; any number of other methods generally involving bridging the antibody to a useful chemical moiety, usually accomplished by modifying lysine or other basic residues or through use of reagents specific for free sulfhydryl groups.

Using the genes for the heavy and light chain variable regions, particularly the hypervariable regions of the variable region may be mutated in accordance with known ways to enhance the binding affinity of the antibody or to broaden reactivity. One may use in vitro selection to identify the optimum binding antibodies using phage display methodologies, random or directed mutagenesis of sequences, or other similar methodologies. Alternatively, one may use an alanine or glycine walk of the hypervariable regions to identify essential amino acids and then vary the amino acids at those or other sites to identify improved binding of the epitope. Other techniques known in the art may be employed to provide the mutagenized antibodies.

Instead of using the hybridomas as a source of the antibodies, the genes may be isolated and introduced into an appropriate mammalian host cell, e.g., CHO, HeLa, CV1, or the like. Suitable expression plasmids are exemplified by pcDNA3.1 Zeo, pIND(SP1), pREP8 (all available from Invitrogen, Carlsbad, Calif.) (see Example 11), and the like. The antibody genes may be expressed via viral or retroviral vectors, which may be exemplified by MLV based vectors, vaccinia virus based vectors, etc. Similarly, the antibody genes may be expressed using the pCOMB series of vectors on the surface of M13 phage, as two independent chains, which may be renatured to form the intact antibody. Alternatively, the antibodies may be expressed as a single chain, including at least the variable regions. The genes may be used for gene therapy by introducing the genes into appropriate cells, such as lymphocytes, muscle cells, fibroblasts, and the like, where the antibodies may be expressed and secreted, either constitutively or inductively, to provide a continuous or intermittent source of the antibodies over a predetermined period of time, based on the lifetime of the host cell. The genes in conjunction with a marker gene, e.g., antibiotic resistance, may be introduced in cell cultures of cells taken from a subject, the modified cells selected by means of the marker and the marked cells returned to the host. The DNA may be introduced into the cells using various plasmid DNA, naked DNA, DNA virus constructs, such as adenovirus, adeno-associated virus, or vaccinia virus or RNA viruses such as Vesicular stomatitis virus, sindbis virus, and semiliki forest virus to name but a few. The DNA would have a construct having a promoter for which transcription factors are present in the subject cells or can be induced or introduced and the genes under the transcriptional control of such promoter. Other regulatory sequences may also be present, such as leaders for secretion, enhancers, RNA stabilizing sequences, and the like.

For diagnostic purposes, the antibodies may be used in a wide variety of formats for detecting the E1 or E2 protein, discerning HCV genotypes, detecting virions and antibodies, see for example U.S. Pat. No. 5,695,390, incorporated herein by reference. The antibodies may be used individually or in combination with other of the subject group or other antibodies or with lectins which bind to the glycosyl groups present on E1 or E2, the virion envelope proteins, or other proteins with which HCV E1 or HCV E2 complexes, e.g., a HCV E1:HCV E2 complex. For diagnostic purposes, a wide variety of labels may be employed, which for the most part have been mentioned previously. These include, but are not limited to, fluorophores, chemiluminescers, radioisotopes, enzymes, particles, e.g., colloidal carbon and gold, latex particles, etc., ligands for which there are high affinity receptors, and prolabels, which can be activated to provide a detectable signal.

In one embodiment, a surface is coated with a protein, which will bind to HCV antigens as free, or circulating proteins or as part of an intact or partially intact virion. One may use antibodies of the subject invention which bind to both type 1 and 2 HCV, or lectins, such as *Galanthus nivalis* lectin. One may also use antibodies of the subject invention, which bind to types 1, 2, and 3. In particularly preferred embodiments, the antibodies of the invention bind to at least four genotypes. In particularly preferred embodiments, the antibodies of the invention bind to E1 of the genotypes HVC 1a, 1b, 2b, and 3a. The assay involves contacting the surface with a medium, which may contain free or virion involved protein, where the medium may be the sample or a solution of known E1 or E2 of one or more genotypes. After incubation and washing to remove non-specifically bound protein, the assay may proceed in various manners depending upon what is being assayed. Where a blood sample suspected of being seropositive is being assayed, the sample is applied to the layer of E1 or E2 protein, incubated, and washed, and the presence of human antibodies bound to the protein layer determined. One may use labeled anti-(human antibodies) (other than against the isotype of the subject antibodies, where the subject antibodies have been initially used). In assays for antibodies in seropositive subjects, the subject antibodies may be used as controls with the same reagent used to detect any human anti-HCV in the sera of such subjects.

The specificity of the antibodies in the sample can be confirmed by using the subject antibodies, which are differentially labeled from the anti-(human antibodies) and determine whether they are blocked by the antibodies in the sample.

Where the sample is assayed for HCV E1 or HCV E2 protein, detection employs labeled subject antibodies, the selection depending upon whether one is interested in genotyping or detection of E1 or E2 protein. After washing away non-specifically bound antibody, the presence of the labeled antibodies is determined by detecting the presence of the label in accordance with known techniques. Alternatively, where the subject antibodies are bound to the surface, a labeled lectin for E1 or E2 may be employed to detect the presence of the E1 or E2 protein.

The subject antibodies can be used to measure the reactivity of other antibodies, including antibodies in sera, monoclonal antibodies, antibodies expressed as a result of genetic engineering. Desirably, intact virions are used, rather than HCV proteins, although conformationally conserved envelope proteins may also find use. For virion capture, see, for example, Kimura et al., 1998 *J. Med. Virology* 56:25-32; Morita et al., 1996 *Hapato-Gastroenterology* 43:582-585; Sata et al., 1993 *Virology* 196:354-357; and Hijikata et al., 1993 *J. Virology* 67:1953-1958, each of which is incorporated herein by reference. One protocol is to coat a solid support with a lectin, e.g., GNA, and then contact the surface with a medium, e.g., serum of a seropositive patient, comprising intact HCV virions. Additives which might destroy the virions should be avoided, e.g., detergents. After incubating the medium and washing to remove non-specifically bound components of the medium, the virions may be contacted with the antibodies of the subject invention and the antibodies of the sample. This may be performed concurrently or consecutively, where the sample is added first. An amount of the subject antibody is used which is sensitive to displacement by another antibody. Such amount may be determined empirically, and one may wish to use different amounts of the subject antibody in a series of tests. By knowing the signal, which is obtained in the absence and presence of the sample, one can determine the reactivity or binding affinity of the antibodies in the sample. Various techniques may be used to determine the amount of a subject antibody bound to the virions. Where the subject antibodies are labeled, e.g., biotin or digoxigenin, streptavidin or anti(digoxigenin) labeled with a fluorophore or enzyme whose substrate produces a detectable signal can serve to determine the amount of the subject antibodies.

Where the receptor (antibody or lectin) is labeled with a DNA sequence, either directly or indirectly (indirectly intends a ligand-nucleic acid sequence conjugate which can bind to empty sites of the receptor bound to the virion), by using primers homologous to the label sequence and standard conditions of the PCR, the sequence may be expanded. The DNA may then be detected in a separate hybridization reaction or by agarose gel electrophoresis. Alternatively, the Taqman approach may be used, using an internal labeled oligonucleotide probe homologous to the amplified sequence, having a light emitting label, fluorophore or luminescer, at one end and a quenching moiety at the other end. As the fragment is amplified, the 5'-3' exonuclease activity of the Taq polymerase degrades the hybridizing oligonucleotide freeing the fluorophore from the quencher, so that the fluorophore may now be detected by irradiation of the medium with light of an appropriate wavelength.

One may also use a labeled oligonucleotide probe appropriate for performing cycling probe technology. An oligonucleotide is constructed of about 15-20 deoxynucleotides homologous to the label and having a TM$\leq$45° C., a sequence of about 5 or more ribonucleotides homologous to the label and having a TM$\leq$45° C. The intact oligonucleotide will have a TM>60° C. The oligonucleotide is further modified as described above with a light emitting label and a quencher label. After adding an excess of the oligonucleotide construct to the bound label and allowing it to hybridize to the bound label at a temperature of about 55° C., RNase H, active at 55° C. is added to degrade the ribonucleotides. Upon denaturation the light-emitting label will be released and free of the quencher, and upon irradiation or activation its light emission determined.

Alternatively, transcription mediated amplification (TMA) may be employed. In this case, the bound oligonucleotide label contains a promoter recognized by T7 polymerase or other convenient polymerase. Addition of T7 or other appropriate polymerase and rNTPs under appropriate conditions results in the transcription of the bound oligonucleotide to oligoribonucleotides, which can then be detected by any convenient means, e.g., electrophoresis.

Labeled subject antibodies may be used in assaying for the presence of HCV from biopsy material. Labeled antibody may be incubated with immobilized biopsy material, such as a liver slice, with a solution of one or more of the subject labeled antibodies. After washing away non-specifically bound antibodies, the presence of the antibodies bound to the cells of the biopsied tissue may be detected in accordance with the nature of the label.

Conformationally conserved E2 genotype proteins 1a, 1b, 2a, and 2b, the latter two being novel expression compositions are provided as proteins expressed from vaccinia virus constructs. Their preparation is described in the experimental section. The proteins are obtained free of amino acids of E1 proteins, although they can be prepared from genes encoding both E1 and E2, where the resulting fusion protein is processed to provide the two proteins which are no longer covalently joined, but may exist as a complex. Conformationally conserved E1 genotype proteins can similarly be prepared by any mammalian expression vector such as pDisplay by Invitrogen (Carlsbad, Calif.) described in the experimental section. The proteins may be isolated from a lysate. The protein may be readily purified using affinity chromatography, HPLC or non-denaturing gel electrophoresis. The proteins may be obtained in purities exceeding 95 wt. %, usually at least 99 wt. %. The proteins may be used in assays for genotyping sera from HCV infected patients, in screening monoclonal antibodies for affinity and specificity, for evaluating drugs where the proteins are the target of the drugs, for immunizing mammalian hosts for the production of antisera and monoclonal antibodies, and the like. Their use in diagnostic assays has already been discussed.

The antibodies may be used to identify the structural epitopes on E1 or E2 proteins that they bind. Two basic approaches may be employed using the monoclonal antibodies for identifying conformational epitopes. In the first, natural variants or mutation analysis of HCV isolates may be used to identify regions, and ultimately individual amino acids that are involved in the epitopes recognized by the monoclonal antibodies (Schwartz et al., 1999 *J. Mol. Biol.* 287:983-999; incorporated herein by reference). The antibodies are screened against a number of different HCV E1 or E2 isolates, identifying isolates that are selectively non reactive with individual antibodies. For example, HMAb CBH-11 reactivity with HCV E2 protein Q1a is reduced compared to its reactivity with HCV E2 Q2a (FIG. 9). "Chimeric" E2 envelope proteins are then constructed in which portions of the chimera are derived from E2 proteins from one HCV genotype and other portions are derived from E2 proteins of another HCV genotype. These chimeric E2 proteins are constructed by PCR amplifying overlapping fragments, and/or by using restriction sites common to both E2 proteins. An alternative method is DNA shuffling as pioneered by the biotechnology company Maxy-Gen. By surveying the observed binding reactivities of different chimeric E2 proteins with different monoclonal antibodies, amino acid regions in the E2 proteins critical in forming conformational epitopes are identified. Once the critical regions are identified, individual amino acids that differ between the different genotypes are mutated to compose a reactive E2 sequence. Mutants that restore full reactivity identify amino acids that are involved in forming the epitope.

A second basic approach to defining a conformational epitope is to synthesize a series of overlapping peptides 10-15 residues in length that encode the desired sequence of HCV E1 or E2. The peptides are then screened against the antibodies using high concentrations of antibody (often 100 µg/ml or higher). Individual regions that comprise the full conformational epitope often retain residual binding activity with the antibody that can be detected. Once these regions are identified, they can be confirmed using mutational studies involving the 10-15 residues of the peptide, either in the context of the peptide or by substituting into a conformationally intact HCV E1 or E2 protein. A variation of this methodology is described in (Reineke et al., 1999 *Nature Biotechnology*, 17:271-275; incorporated herein by reference).

The subject antibodies also may be used for screening for mimotopes. Mimotopes may be prepared using phage display, and the peptides screened with the subject antibodies (Livnah et al., 1996 *Science* 273:464-471; Prezzi et al., 1996 *J. Immunol.* 156:4504-4513; each of which is incorporated herein by reference). Antibodies that recognize conformationally conserved HCV epitopes may be used as templates for the rational design of peptide or non-peptide structural mimics of the conformational epitope or mimotopes.

The generation of mimotopes is biologically significant. By mimicking the structure of the conformationally defined viral epitope, the mimotope can interfere with the ability of the virus to bind its target receptor by binding to the receptor itself. For example, analysis of a solved crystal structure defining the interface between a monoclonal antibody and tumor necrosis factor (TNF) enabled the rational design of a non-peptide mimetic capable of antagonizing the biological function of TNF by binding to the TNF receptor (Takasaki et al., 1997 *Nat. Biotech.* 15:1266-1270; incorporated herein by reference). Computational techniques that may be employed to rationally deduce protein folding from a primary amino acid sequence for use in designing a peptide structural mimetic are reviewed in Teichmann et al., 1999 *Curr. Opin. Struct. Biol.* 9:390-399; incorporated herein by reference. The practical application of computer programs for use in structurally modeling conformationally conserved epitopes is described by Schwartz et al., 1999 *J. Mol. Biol.* 287:983-999; incorporated herein by reference. An alternative method for rationally creating a peptide structural mimic of an antibody epitope involves systematic permutations of synthetic peptides designed to be a linear representation of a discontinuous antibody binding site (Reineke et al., 1999 *Nat. Biotech.* 17:271-275; incorporated herein by reference).

Peptides, or other small molecules having specific affinity for a monoclonal antibody and competitive with an epitope of a conformationally intact E1 or E2 protein. Alternatively, peptides or other small molecules may have specific affinity for a monoclonal antibody and competitive with an epitope of E1 complexed with E2 or E2 complexed with E1. Such peptides may be used as vaccines, in diagnostic assays, for immunization for the production of antibodies to a specific HCV epitope, in competitive assays for defining genotype, and the like. See, for example, Puntoriero et al., 1998 *EMBO J.* 17:3521-3533; Meola et al., 1995, *J. Immunol.* 154:3162-3172; Tafi et al., 1997 *Biol. Chem.* 378:495-502.

Another approach to effectively create structural mimetics of conformationally conserved HCV epitopes is to produce anti-idiotypic antibodies to the conformationally dependent anti-HCV HMAbs. Anti-idiotypics may effectively block the binding of native virus with its target receptor (Chanh et al., 1987 *Proc. Natl. Acad. Sci. USA* 84:3891-3895; Kopecky et al., 1999 *Intervirol.* 42:9-16; Xue et al., 1993 *J. Gen. Virol.* 74:73-79; each of which is incorporated herein by reference). Anti-idiotypic antibodies recognizing the conformational binding sites of any one of the anti-HCV HMAbs CBH-2, 5, 4B, 4D, 4G, 7, 8C, 8E, 9, or 11 could prevent viral infectivity by interfering with E2 binding to a target cellular protein, or even by interfering with virion attachment to the target cell. Similarly, anti-idiotypic antibodies recognizing the conformational binding sites of either of the HCV HMAbs H-114 or H-111 could also prevent viral infectivity by interfering with E2 binding to a target cellular protein, or even by interfering with virion attachment to the target cell.

The subject antibodies find use for prophylactic therapy or for treating HCV infection, by reducing viral load, by inhibiting binding of the virus to its target proteins, by inhibiting virus mediated fusion with a target cell, and by interfering with conformational changes in the viral envelope proteins necessary for cell infectivity. The composition used can be a monoclonal antibody directed to a single conformational epitope, or a mixture of complementary monoclonal antibodies that recognize distinct conformational epitopes on one or more viral envelope proteins, thereby simultaneously interfering with multiple mechanisms in the infectious process.

For reducing viral load of a body component, particularly a body component of a patient infected with HCV, patient blood is passed through a device comprising the antibodies bound to a surface for capturing the HCV. See, for example, U.S. Pat. Nos. 5,698,390 and 4,692,411; each of which is incorporated herein by reference. Various other devices found in the literature can be used with the subject antibodies to achieve a similar result. A body component can be a biological fluid, a tissue, an organ, such as the liver, and the like.

The antibodies also may be used for passive immunization therapies or other in vivo therapies. See, for example, Piazzi et al., 1997 *Arch Intern Med.* 157:1537-1544; Farci et al., 1996 *Proc. Natl. Acad. Sci. USA.* 93:15394-15399; al-Hemsi et al., 1996 *Clin. Transplant.* 10:668-675; Krawczynski et al., 1996 *J. Infect. Dis.* 173:822-828; each of which is incorporated herein by reference. For such therapeutic use, the antibodies may be formulated in any convenient way for injection or intravenous administration. Various media may be used such as phosphate buffered saline, saline, or the like. The amount of the antibodies may be varied depending on the level of infection, the affinity of the antibodies, the manner of administration, the frequency of administration, the response of the patient, the use of other therapeutics, and the like. Generally the amount of antibody administered will be in the range of about 0.1 to 5 mg/kg. See, for example, Andrus et al., 1998 *J. Infect. Dis.* 177:889-97 and Kreil et al., 1988 *J. Virology* 72:3076-3081; each of which is incorporated herein by reference.

The chimpanzee is an accepted animal model for screening HCV vaccines and therapeutics. See, for example, Farci et al., 1996 *Proc. Natl. Acad. Sci. USA* 93:15394-15399; Farci et al., 1994 *Proc. Natl. Acad. Sci. USA* 91:7792-7796; Farci et al., 1992 Science 258:135-140; Krawczynski et al., 1996 *J. Infect. Dis.* 173:822-828; Bassett et al., *J. Virology* 72:2589-2599; each of which is incorporated herein by reference. The effectiveness of the antibodies can be determined by monitoring for the presence and titer of HCV RNA using quantitative PCR methods. A successful reduction of viral load, or prevention of infection in a test animal or subject is reflected as a reduction or elimination of HCV RNA in serum. Enzymatic tests such as measurement of alanine aminotransferase and/or use of sequential punch needle liver biopsies also is used to test effectiveness, where improvement in the rating of either would indicate a reduction in viral-induced liver damage.

Vaccines

In formulating vaccines to HCV, any agent that mimics at least one conformational epitope of the HCV E1 or HCV E2 protein may be used. For example, the agent may be a peptide, protein, small molecule, mimotope, organic compound, organometallic compound, or inorganic compound, etc. In a preferred embodiment, the epitopes represented in the vaccine include those against which antibodies known to prevent infection are directed. In another preferred embodiment, the epitopes represented in the vaccine include ones that are conserved among different genotypes of the virus or among different strains of the virus. In a particularly preferred embodiment of the present invention, peptides or proteins that contain the conformationally-defined epitopes of E1 or E2 of HCV are used in the formulation of a vaccine to prevent an infection by HCV or to treat an HCV infection. In other particularly preferred embodiments, peptides or proteins that contain conformationally defined epitopes of at least one conformationally defined epitope of E1 and at least one conformationally defined epitope of E2 of HCV are used in the formulation of a vaccine. Alternatively, the E1 and E1 epitopes may be linear epitopes. In yet another preferred embodiment, the E1 and E2 epitopes may be a mixture of linear and conformational epitopes. The peptides or proteins are preferably less than 100 amino acids in length, and more preferably less than 50 amino acids in length. In a particularly preferred embodiment, the peptides to be used in formulating a vaccine are peptide fragments of the E1 or E2 protein of HCV. Preferably the peptide folds in a manner similar to its fold in the native E1 or E2 protein thus preserving the three-dimensional structure of the conformational epitope.

The vaccine may also contain proteins that represent concatenated peptides that have the conformational epitope to which antibodies are desired. Several different peptides making up the multimer may be used so that each peptide contains a different epitope, or the same peptide may be used more than once in the multimer.

Peptides of the invention may be synthesized using any method known in the art including Merrifield solid phase chemistry. The peptides may also be obtained by cleavage of E1 or E2 protein and purification. The peptides may be made recombinantly and produced in *E. coli*, yeast (e.g., *S. cerevisiae*), insect cells (e.g., Sf9 cells), or mammalian cells (e.g., CHO cells) using any available techniques in the art (Sambrook et al.; Miller & Calos, eds., *Gene Transfer vectors for Mammalian Cells,* 1987; Ausubel et al., eds., *Current Protocols in Molecular Biology,* 1987; each of which is incorporated herein by reference). The peptides may be modified to increase their immunogenicity, solubility in aqueous solution, or to increase their propensity to fold correctly. For example, peptides may be glycosylated, farnesylated, hydroxylated, reduced, oxidized, etc.

In a particularly preferred embodiment, the peptide comprises amino acids 411 through 644 of the E2 protein of HCV genotype 1b. In another embodiment, the peptide comprises amino acids 470 through 644 of the E2 protein of HCV genotype 1b. In yet another embodiment, the peptide comprises amino acids 644 through 661 of the E2 protein of HCV genotype 1b. As would be appreciated by one of ordinary skill in this art, analogous amino acid sequences of E2 proteins from other genotypes of HCV may be used. Analogous sequences may be determined by aligning multiple sequences of the E2 protein from different strains or genotypes of HCV. Homologous sequences that preserve the desired epitope may also be used in the formulation of vaccines. Preferably, the sequences are at least 50% homologous to the native sequence from HCV 1b E2 protein, more preferably at least 60% homologous, and most preferably at least 70% homologous.

In a particularly preferred embodiment, the peptide comprises amino acids 192 through 383 of the E1 protein of HCV genotype 1b. In another embodiment, the peptide comprises amino acids 192 through 340 of the E1 protein of HCV genotype 1b. In yet another embodiment, the peptide comprises amino acids 192 through 352 of the E1 protein of HCV genotype 1b. In yet another embodiment, the peptide comprises amino acids 192 through 366 of the E1 protein of HCV genotype 1b. In yet another embodiment, the peptide comprises amino acids 192 through 370 of the E1 protein of HCV genotype 1b. As would be appreciated by one of ordinary skill in this art, analogous amino acid sequences of E1 proteins from other genotypes of HCV may be used. Analogous sequences may be determined by aligning multiple sequences of the E1 protein from different strains or genotypes of HCV. Homologous sequences that preserve the desired epitope may also be used in the formulation of vaccines. Preferably, the sequences are at least 50% homologous to the native sequence from HCV 1b E1 protein, more preferably at least 60% homologous, and most preferably at least 70% homologous.

In a particularly preferred embodiment, the peptide or collection of peptides is mixed with an adjuvant and optionally other pharmaceutically acceptable excipients before administration to an individual.

Adjuvants

Compositions utilized in the practice of the present invention may include, or may be administered as part of a protocol that includes one or more adjuvants or cytokines. Any adjuvant may be used in accordance with the present invention. A large number of adjuvant compounds is known; a useful compendium of many such compounds is prepared by the National Institutes of Health and can be found on the world wide web (http:/www.niaid.nih.gov/daids/vaccine/pdf/compendium.pdf, incorporated herein by reference; see also Allison *Dev. Biol. Stand.* 92:3-11, 1998; Unkeless et al. *Annu. Rev. Immunol.* 6:251-281, 1998; and Phillips et al. *Vaccine* 10:151-158, 1992, each of which is incorporated herein by reference). Hundreds of different adjuvants are known in the art and could be employed in the practice of the present invention.

Administration

Those of ordinary skill in the art will appreciate that antibodies or vaccines to be administered to individuals according to the present invention may be administered via any of a variety of routes, protocols, and dosing regimens. Known routes of administration include, for example, intravenous (IV), intraperitoneal (IP), intragastric (IG), subcutaneous (SQ), intramuscular (IM), oral (PO), rectal (PR), intrathecal, vaginal, intranasal, transdermal, intradermal, etc. Intravenous, intramuscular, transdermal, intradermal, intranasal, and oral deliveries are generally preferred.

Pharmaceutical Compositions

Pharmaceutical compositions for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of an agent, it is often desirable to slow the absorption of the drug from subcutaneous or intramuscular injection. This may be accomplished by the use of a liquid suspension of crystalline or amorphous material with poor water solubility. The rate of absorption of the agent then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of agent to polymer and the nature of the particular polymer employed, the rate of release of the agent can be controlled. Examples of other biodegradable polymers include poly(orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions, which can be used, include polymeric substances and waxes.

Solid compositions of a similar type may also be employed as fillers in soft and hard-filled gelatin capsules using such excipients as lactose or milk sugar as well as high molecular weight polyethylene glycols and the like.

The compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of an inventive pharmaceutical composition include ointments, pastes, creams, lotions, gels, powders, solutions, sprays, inhalants, or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the compounds of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Treatment of Patients

The present invention also provides a method of stratifying and optionally treating patients infected with HCV. In a particularly preferred embodiment, the treatment regimen is particularly suited for an individual. A patient to be treated is provided, and a sample of serum is taken from the patient. The serum is then analyzed for the presence of particular antibodies such as neutralizing antibodies or antibodies that bind to a particular region or epitope of a protein of HCV. Any method known in the art including those described in this application may be used to determine the presence of the antibodies to be detected (e.g., ELISA, competition assay). Based on the level of antibodies in the patient's serum, a treatment can be designed for the patient. For example, a patient who does not have antibodies known to interfere with the binding of virions to their natural receptor may be treated with monoclonal antibodies of this type. In one particularly preferred embodiment, the sera from the HCV-infected patient is considered positive for the presence of a competing antibody if 50% or greater inhibition of E2 binding was obtained at a dilution of 1/200 or greater of the patient's serum, more preferably of 1/500 or greater, and most preferably of 1/1000 or greater.

One of the advantages of this method is that the treatment is tailored to the particular individual being treated. Only those antibodies that are needed and not produced naturally by the patient are administered. This avoids or reduces the risk of adverse reactions from administering therapeutics that are not needed. This method would also eliminate the expense of treating patients who would not benefit from such treatment. For example, if a patient were already producing an antibody to a particular epitope of E2, there would be no need to administer a human monoclonal antibody directed against the epitope exogenously.

Those skilled in the art will further appreciate that a patient may receive infusions of one or several HCV HMAbs that can reduce the amount of HCV virions circulating that are capable of infecting new cells. This antibody treatment may be given alone, during the course of another treatment, or after the cessation of treatment of other antiviral compounds. Additionally, the HCV HMAbs may be linked to known toxins or proteins capable of inducing apoptosis or other cell death processes. These modified HCV HMAbs can be administered to individuals suffering from HCV mediated liver disease as a means of killing HCV infected cells.

In another particularly preferred embodiment, the treatment may include administering a vaccine designed to induce the production of antibodies that have been found to be lacking in the patient. The most effective vaccines are preferably composed of antigens that have a native conformation, mediate a protective response (such as complement activation or virus neutralization) or can induce a strong antibody response. In a particularly preferred embodiment, the vaccine contains an epitope or mimotope thereof, to which antibodies are not being produced naturally in the individual. For example, synthetic peptide mimotopes isolated with HCV HMAbs, especially HCV HMAbs recognizing multiple genotypes, have the potential to induce a potent immune response similar to the antibody used in the original isolation of the mimotope. The administration of such a vaccine would induce the patient's immune system to start producing a set of antibodies directed against the administered epitope. It will be appreciated that the mimotopes (or epitopes) of the invention can be used alone or in combination with recombinant proteins or as a cocktail of several different mimotopes.

In the present invention, pharmaceutical compositions are provided that include HMAbs to one of either HCV E1 or HCV E2 protein. In certain preferred embodiments, the pharmaceutical compositions include antibodies to both HCV E1 and E2. In other preferred embodiments, the pharmaceutical compositions include two or more antibodies to HCV E1 and HCV E2. As described herein the HCV E1 and E2 antibodies can be directed to E1 or E2 epitopes of a single HCV genotype or multiple HCV genotypes. It will also be appreciated that the antibodies can be directed to either linear or conformational epitopes, as described herein. Particularly preferred combinations of antibody include H-111 with any anti-E2 human monoclonal antibody. Some particularly preferred combinations of antibodies include combinations of the H-111 HMAb with any one or more of CBH-5, CBH-7, CBH-4G, CBH-8C, CBH-17, or CBH-2.

Applications

The HCV antibodies of the present invention can be used to identify HCV receptors. Those skilled in the art will appreciate the multitude of ways this can be accomplished (Sambrook J., Fritsch E. and Maniatis T. *Molecular Cloning: A Laboratory Manual. Cold Spring Harbor Press*, Cold Spring Harbor, N.Y., 1989; Ausubel et al., eds., *Current Protocols in Molecular Biology*, 1987; each of which is incorporated herein by reference). Typically, protein and peptide receptors, and in the case of the present invention, receptors for HCV proteins and peptides, preferably E1 and E2, can be identified by determining whether an antibody to E1 or E2 can inhibit HCV virions attachment to a cell susceptible to HCV infection. A susceptible cell can be incubated in the presence of HCV and anti-HCV E1 or E2 antibody and use a cell binding assay to determine whether attachment is decreased in the presence of the antibody.

Cells expressing putative receptors for HCV or libraries of putative receptors for HCV may also be screened for their ability to bind HCV. For example, cells expressing a putative HCV receptor (e.g. a receptor for HCV E1 or E2) can be contacted with an HCV protein or peptide in the presence of an antibody for a time and under conditions sufficient to allow binding of the HCV protein or peptide to putative receptor on the surface of the cell. Alternatively, the HCV protein or peptide, or HCV virions, can be pre-incubated with the antibody prior to contacting the putative receptor on the cell surface. Binding can be detected by any means known in the art, e.g., flow cytometry etc. (see Ausubel et al. or Sambrook et al., supra). A decrease in binding to the surface of the cell in the presence of antibody compared to binding in the absence of the cell in the absence of the antibody indicates the identification of an HCV receptor.

Other methods of identifying HCV receptors, such as E1 or E2 receptors, include the use of solid supports, such as beads, columns and the like. For example, receptors for HCV proteins and peptides, or HCV virions, can be identified by attaching an HCV antibody to a solid support and then contacting the antibody with an HCV protein or peptide for a time sufficient for the HCV protein or peptide to bind to the antibody. This provides an HCV protein ligand for putative HCV receptors that can be contacted with the antibody:ligand complex on the solid support for a time and under conditions sufficient to allow binding of a receptor to the HCV protein or peptide. The proteins can be expressed from a library or provided as a cell extract or purified protein preparation from natural or recombinant cells. Once specific binding complexes between the HCV protein or peptide are formed, unbound HCV proteins or peptides, e.g., library proteins or peptide that did not bind specifically to the HCV proteins or peptides, are removed, e.g., by standard washing steps. The bound proteins are then eluted and identified, e.g. by gel electrophoresis.

These and other aspects of the present invention will be further appreciated upon consideration of the following Examples, which are intended to illustrate certain particular embodiments of the invention but are not intended to limit its scope, as defined by the claims.

EXAMPLES

Example 1

Production of HCV E2 Proteins from Multiple Genotypes in Vaccinia Virus

To analyze the reactivity of HCV sera and test the breadth of HCV-HMAbs reactivity, the complete coding sequence of HCV were cloned from isolates of HCV genotypes 1a, 1b, 2a, and 2b, were PCR amplified from HCV positive sera and expressed with vaccinia virus using the pVOTE (Ward et al., 1995 *Proc. Natl. Acad. Sci. USA* 92:6773-6777; incorporated herein by reference) transfer vector (constructs Q1a, Q1b, Q2a, and Q2b for HCV genotypes 1a, 1b, 2a, and 2b, respectively). Genotype selection was based on its divergence and frequency among HCV infected individuals in the United States (Mahaney et al., 1994 *Hepatology* 20:1405-1411; incorporated herein by reference). Oligonucleotide primers were designed to amplify fragments that expressed the final 39 amino acids of E1, all of E2/p7, and the N-terminal 98 amino acids of NS2. See Table 2. SEQ ID NOS: 18-27).

Accordingly, aliquots of plasma from individuals PCR positive for HCV RNA were obtained and genotyped using the InnoLipa HCV genotyping assay performed according to manufacturer's instructions (Innogenetics, Ghent, Belgium). RNA was prepared from 125 µl of plasma from individuals infected with HCV genotypes 1a, 1b, 2a, and 2b using the Puerescript RNA kit, according to manufacturer's instructions (Gentra Systems, Minneapolis, Minn.). RNA pellets were re-suspended in 25 µl of RNAse free $H_2O$ and 10 µl was subjected to reverse transcriptase PCR. Reverse transcription reactions were performed using MMLV reverse transcriptase employing the reverse HCV specific primer HCV E2-R1 5'-CGC GCA CrA AGT AsG GyA CT-3' (SEQ ID NO: 16). Reverse transcription was for 60 minutes at 40° C. Reverse transcribed cDNA was denatured by a 5 minute incubation at 98° C. followed by cooling to 4° C. and the addition of PCR mix containing 0.15 mM dNTPs, 3 µl 10×PCR buffer, 3 units of Amplitaq polymerase, and the forward primer HCV E2-F1 5'-CGC ATG GCi TGG GAy ATG ATG-3' (SEQ ID NO: 17). Amplification was for 30 cycles of 94° C. for 1 minute, 55° C. for 3 minutes, and 72° C. for 3 minutes. Between 2 and 8 µl of amplified product was then subjected to a second round of PCR amplification with using the forward primer appropriate for cloning each genotype and an internal reverse primer INT-Reverse (Table 2, SEQ ID NOS: 18-27) or the reverse primer appropriate for each genotype and INT-Forward. PCR amplifications were for 30 cycles of 94° C. for 1 minute, 60° C. for 2.5 minutes, and 72° C. for 2 minutes. Appropriately sized bands (~820 nucleotides for the genotype specific forward primer and INT-Reverse and ~1080 nucleotides for INT forward and the genotype specific reverse primer) and were excised from ethidium-bromide stained agarose gels and purified using a commercially available resin (Qiagen, Valencia, Calif.). Approximately 50 ng of each band were combined and re-amplified with the forward and reverse primers appropriate for each genotype (Table 2). PCR amplifications were for 30 cycles of 94° C. for 1 minute, 55° C. for 2.5 minutes, and 72° C. for 2 minutes. The amplified products were then excised from ethidium bromide stained agarose gels, purified, and digested with the appropriate restriction enzymes. This three-step amplification procedure resulted in a much higher yield of full-length insert than standard two-step procedures. The digested DNAs were then ligated into a similarly digested pVOTE 1 or pVOTE 2 vector (Ward et al., 1995 *Proc. Natl. Acad. Sci. USA* 92:6773-6777; incorporated herein by reference). The ligated plasmids were transfected into competent *E. coli* and insert-containing clones were identified and propagated using standard methods (Sambrook J., Fritsch E. and Maniatis T. *Molecular Cloning: A Laboratory Manual*. Cold Spring Harbor Press, Cold Spring Harbor, N.Y., 1989; incorporated herein by reference). The clones obtained were designated Q1a, Q1b, Q2a, and Q2b for constructs expressing full length E2 and p7 of HCV genotypes 1a, 1b, 2a and 2b, respectively.

TABLE 2

Primers* employed in cloning HCV E2 protein

| Gtyp | Forward Primer | SEQ ID NO. | Reverse Primer | SEQ ID NO. |
|---|---|---|---|---|
| 1a | CG AGG CIT <u>CAT ATG</u> ATC GCT GGT GCT TGG<br>            Nde I | 18 | CG GAA TCC <u>CTG CAG</u> CTA CAA ACT GGC TTG AAG AAT CCA<br>             Pst I | 19 |
| 1b | CG CAT ATG <u>GAG CTC</u> GCG GGG GCC CAC TGG<br>            Sac I<br>GGA GT | 20 | GC TCT AGA <u>CTG CAG</u> CTA TAT GCC AGC CTG GAG CAC CAT<br>             Pst I | 21 |
| 2a | C GCT CGA <u>GCC ATG GTT</u> GGC GGG GCT CAT<br>          Nco I<br>TGG GGC | 22 | TC GAA TTC <u>GGA TCC</u> TAC AAA GCA CCT TTT AGG AGA TAA GC<br>            BamH I | 23 |
| 2b | C GCT CGA <u>GCC ATG GTT</u> TTC GGC GGC CAT<br>          Nco I<br>TGG GTG | 24 | TC GAA TTC <u>GGA TCC</u> TAC AGA GAC GCT TTA AGG AGG TAG GC<br>            BamH I | 25 |
| INT | TG GTT CGG BTG YWC ITG GAT GAA | 26 | TAA TGC CAi ARC CKR TAi GGG TAG TC | 27 |

*Inner nested primers employed in cloning of vaccinia virus E2 constructs. The restriction sites employed in the cloning are underlined. The primers contained additional restriction sites in their 5' ends. The primers contain other restriction sites. Gtyp = HCV genotype. The primers INT-F and INT-R contain degenerate nucleotides and were used for all genotypes. PCR amplification conditions are described in Example 1.

Expression of intact E2 protein by vaccinia virus constructs Q1a and Q2b was verified in a transient expression assay. CV-1 cells were infected with 5 plaque-forming units (pfu) of wild type vaccinia virus strain VWA (Ward et al. supra) and then transfected with pVOTE plasmid using Transfectam (Promega, Madison, Wis.), according to the manufacturer's instructions. Cells were cultured in media supplemented with 1 mM Isopropyl-B-D-thiogalactopyranoside (IPTG) to induce expression of HCV proteins (Ward et al. supra). Forty eight hours after transfection the cells were harvested by washing cultured cells with PBS and resuspending the cells in lysis buffer (150 mM NaCl, 20 mM Tris (pH 7.5), 0.5% deoxycholate, 1.0% Nonidet-P40, 1 mM EDTA) to which the protease inhibitors Pefbloc (Boehringer Mannheim, Indianapolis, Ind.), Aprotinin, Leupeptin, and Pepstatin were added to final concentrations of 0.5 mg/ml, 2 µg/ml, 2 µg/ml, and 1 µg/ml, respectively. One hundred microliters of lysis buffer was added for every $3 \times 10^6$ cells harvested. Nuclei were the pelleted by centrifugation at 18,000×g at 4° C. for 10 minutes and the supernatant was either used directly or stored at 4° C. for not more than two days prior to use.

For Western blot analysis, 10 µl of lysis buffer extract was combined with 10 µl of 2×SDS sample buffer (20% glycerol, 10% β-mercaptoethanol, 4.8% SDS, 0.125 mM Tris (pH 6.8), heated to 95° C. for 5 minutes, and fractionated by sodium dodecyl sulfate-polyacrylamide gel electrophoresis (SDS-PAGE) (Laemmli et al., 1970 Nature 227:680-685; incorporated herein by reference) employing 12% polyacrylamide gels. The fractionated proteins were then electrotransferred to nitrocellulose and incubated overnight with murine monoclonal antibody (mMab) 2C8 that recognizes Western blotted HCV E2 (available from Dr. H. Greenberg, Stanford University). mMAb 2C8 was diluted 1:500 in BLOTTO (2.5% non fat dry milk, 2.5% normal goat serum, 0.1% Tween-20 (Sigma, St. Louis, Mo.), 0.02% sodium azide in TBS: 150 mM NaCl, 20 mM Tris, pH 7.5). Purified HCV or control antibodies or HMAb-containing culture media diluted to an IgG concentration of 5 µl/ml in BLOTTO. The blots were washed 3 times with TBS, and bound antibody was detected with the ECL Western blot kit, according to manufacturer's instructions (Amersham, Arlington Heights, Ill.).

The constructs Q1a and Q2b produced an approximately 70 kdal protein that was immunoreactive with mMAb 2C8 (FIG. 1). As expected with the pVOTE system (Ward et al., 1995 Proc. Natl. Acad. Sci. USA 92:6773-6777; incorporated herein by reference) the expression of the HCV E2 proteins was highly dependent on the presence of the inducer IPTG. Expressed protein was also detected from all 4 constructs by IFA with a panel of 10 genotyped HCV sera (data not shown). None of the constructs were reactive with HCV-negative sera nor did any of the HCV antisera react with cells infected with wild type vaccinia virus.

The genotypes of the cloned E2 proteins were confirmed by DNA sequencing of either a 160 bp internal fragment (nts. 2009 to 2168 of HCV-1) from the center of HCV E2 from each of the four clones. See FIG. 2 (SEQ ID NOS: 9-12), or the entire insert (construct Q1b) employing dye terminator methodologies and an automated DNA sequencer (Applied Biosystems, Foster City Calif.). The inserts were highly homologous to the appropriate sequences of HCV E2 available in various databases with no frame shift or termination mutations. See FIG. 3 (SEQ ID NOS: 1-8). Thus, this is good evidence that HCV E2 of all 4 genotypes was accurately expressed by the pVOTE constructs. Plasmids that produced intact HCV were then used to generate recombinant vaccinia virus by homologous recombination into the hemaglutinin locus of the vaccinia virus strain VWA (Ward et al., supra as described Moss and Earl, In F. Ausubel and R Brent and R Kingston (ed.), Current Protocols in Molecular Biology*, Vol. 2, John Wiley & Sons, New York, N.Y., 1994; each of which is incorporated herein by reference). Recombinant vaccinia viruses were identified via infection of BSC-1 cells followed by selection for guanine phosphoribosyl transferase containing virus with media containing mycophenolic acid, xanthine, and hypoxanthine, using standard methods (Moss et al., supra). Purified viral stock was obtained for each recombinant virus and titers measured using BSC-1 cells ranged between $5–10\times10^8$ pfu/ml.

Example 2

Antibody Screening of Potential HCV E2 Positive B-Cell Donors

Since HCV cannot be reliably propagated in vitro, it is necessary to use recombinant envelope proteins expressed in eukaryotic cells to identify individuals with strong titers to HCV proteins. In such screening it is necessary to use methods that preserve the native structure of the envelope proteins thus allowing the detection of antibodies to conformational epitopes. In the identification of sera for the generation of HCV HMAbs an immunofluorescent assay (IFA) was employed. This assay uses acetone-fixed cells and is analogous to methods used in the production of neutralizing HMAbs to conformational epitopes on human T-lymphotropic virus envelope protein (Hadlock et al., 1997 *J. Virology* 71:5828-5840; incorporated herein by reference). For HCV, acetone-fixed cells expressing HCV E2 envelope proteins were used. At various points the E2 proteins were expressed using recombinant baculovirus in Sf9 cells, recombinant vaccinia virus in HeLa cells, as described above, or in Chinese hamster ovary (CHO) cells using a commercially available vector (pDisplay, In Vitrogen, Carlsbad, Calif.). Since insect derived cells may not express viral envelope proteins in a truly native conformation (Rosa et al. supra; Arp et al., 1996 *J. Virology,* 70:7349-7359; each of which is incorporated herein by reference) the use of vaccinia virus or mammalian cell expression systems is preferred. The fluorescence observed with a given serum was scored visually via fluorescence microscopy, and in some cases increasing dilutions of the sera were evaluated to obtain an end point dilution titer of the potential donor sera.

To confirm results obtained with immunofluorescence a microtiter plate assay for evaluating the reactivity of sera to HCV E2 was developed. Monolayers of HeLa cells were grown to 80% confluence and infected with 5 pfu/cell of VWA and 5 pfu/cell of recombinant vaccinia virus or 5 pfu of VWA only. HCV recombinant viruses were mixed with wild type vaccinia with an intact hemaglutinin gene to minimize the vaccinia virus induced cytopathic effect observed with hemaglutinin minus virus (Seki et al., 1990 *Virology* 175:372-384; incorporated herein by reference). Twenty-four hours after infection cells were harvested. Extracts were prepared by washing the cells with PBS and then resuspending $30\times10^6$ cells in 1 ml of lysis buffer (150 mM NaCl, 20 mM Tris (pH 7.5), 0.5% deoxycholate, 1.0% Nonidete-P40, 1 mM EDTA, 0.5 mg/ml Pefablock (Boehringer Mannheim, Indianapolis, Ind.), 2 μg/ml Aprotinin, 2 μg/ml Leupeptin, and 1 μg/ml Pepstatin). Nuclei were pelleted by centrifugation at 18,000×g at 4° C. for 10 minutes. Extracts were stored at 4° C. and used for ELISA within 24 hours of preparation. Microtiter plates (Maxisorp, Nalge Nunc International, Rochester, N.Y.) were prepared by coating individual wells with 500 ng of purified *Galanthus nivalis*, lectin (obtained from SIGMA, St. Louis, Mo.) in 100 μl of PBS for 1 hour at 37° C. Wells were then washed with TBS (150 mM NAC1, 20 mM Tris-HCL, pH 7.5), and blocked by incubation for 1 hour at room temperature with 150 μL BLOTTO (TBS plus 0.1% Tween-20, 2.5% normal goat sera, 2.5% non fat dry milk). Plates were washed two times with TBS followed by the addition of 20 μl of extract from vaccinia virus infected HeLa cells 1:5 with BLOTTO. After incubation for 1.5 hours at room temperature, plates were washed three times with TBS followed by addition of HCV sera at various dilutions in 95 μl of BLOTTO supplemented with 5 μL of soluble extract from HeLa cells infected with vaccinia virus VWA. The inclusion of the soluble extract served to suppress reactivity to vaccinia virus proteins that might also be captured by GNA lectin. Plates were incubated for 1.5 hours, wells were washed three times with TBS and 100 μl of anti-human alkaline-phosphatase conjugate (Promega, Madison, Wis.) diluted 1/5000 in BLOTTO was added. After incubation for 1 hour at RT, the plates were then washed four times with TBS followed by incubation with a 1 mg/ml solution of p-nitrophenyl phosphate (PNPP). Substrate development was allowed to proceed for 30 to 45 minutes, then the absorbance of the wells at 405 nm was determined using a multiwell plate reader (Du Pont Co., Wilmington, Del.).

Typical results are presented in FIG. 4. In this experiment five genotyped HCV sera and one serum from an HCV negative blood donor were titrated against HCV E2 proteins of genotypes 1a, 1b, 2a, and 2b, as well as proteins captured from extracts infected with non-recombinant vaccinia virus VWA. Minimal reactivity to the HCV E2 was observed with a serum from an uninfected individual (Graph labeled Negative Serum). Additionally all five sera from HCV infected individuals exhibited little or no reactivity to proteins captured from extracts infected with wild type vaccinia virus (thin black lines, all graphs). It can be appreciated that a wide variation in seroreactivity to HCV E2 proteins was obtained with the five sera tested, with the HCV 2a individual exhibiting the highest overall reactivity.

The results obtained with 12 sera from individuals infected with HCV genotype 2b are presented in FIG. 5. In this graph the dilution of sera that resulted in a specific OD of 0.5 for all four of the HCV E2 proteins is compared (Specific OD is the OD obtained from wells coated with extract of HCV E2 construct—OD of wells coated with extract of non-recombinant vaccinia virus). For all 12 sera, reactivity to HCV 2b or 2a E2 protein was significantly greater than that obtained with HCV 1a or 1b E2 protein. This indicates the superiority of HCV genotype 2 E2 proteins for the detection of antibodies recognizing the HCV envelope in individuals infected with HCV genotype 2a or 2b. Also, the individuals presented on the right side of the graph would be more promising donors for the isolation of HCV HMAbs specific for epitopes present in genotype 2a or 2b E2 proteins.

The donor employed to generate the HCV HMAbs was identified as HCV seropositive with the first generation HCV screening assay during a course of autologous donation. Alanine aminotransferase (ALT) testing of the donated units resulted in 6 out of 7 of the donations being within the normal range (<45 IU). One donation had an ALT value of 49, which is just over the normal cutoff. Otherwise the donor exhibited no outward symptoms of hepatitis. This individual was later confirmed to be HCV positive by PCR using the Roche amplicor HCV assay (Roche Diagnostics, Branchburg, N.J.) and was determined to be infected with HCV of the 1b genotype by the InnoLipa probe assay (Innogentics, Ghent, Belgium). This individual was found to have a high titer of antibodies capable of recognizing HCV E2 using IFA. Testing with the neutralization of binding assay (see below) also indicated this donor had a high titer of potentially neutralizing antibodies. Peripheral blood B-cells were isolated from this individual and successfully used to generate HCV antibody secreting human hybridomas (described below).

Example 3

Production of E2 Antigen-Specific Human Monoclonal Antibodies

Peripheral B-cells were purified from donor T-cells by T-cell rosetting as described (Foung et al., 1984 *J. Immunol. Methods* 134:35-42; incorporated herein by reference) which disclosure is incorporated by reference. Individual cultures of $1\times10^4$ B-cells were EBV-activated in microtiter plates. HCV specific antibodies were detected with an immunofluorescence assay (IFA). Cells infected with recombinant vaccinia virus expressing HCV E2 proteins, recombinant baculovirus expressing HCV E2, and/or mammalian cell lines that have been engineered to express HCV E2 from their DNA were fixed onto HTC supercured 24-spot slides. The cells were fixed with 100% acetone for 10 minutes at room temperature. Fixed cells were incubated with undiluted culture media from EBV activated B cells or hybridomas for 30 minutes at 37° C. and washed for 5 minutes with phosphate buffered saline (PBS), pH 7.4. Slides were then incubated for 30 minutes at 37° C. with 0.001% solution of Evan's blue counterstain and fluorescein isothiocyanate (FITC) conjugated goat-anti-human IgG (Zymed, South San Francisco, Calif.). Bound antibody was revealed by fluorescence microscopy.

Out of 540 cultures, 99 wells showing significant immunofluorescence to HCV E2 were identified (yield ~18%) and 30 of the EBV-activated cultures with different immunofluorescence patterns were selected for electrofusion to mouse-human heteromyelomas as described (Found et al., 1990 *J. Immunol. Methods* 134:35-42; Zimmerman, et al., 1990 *J. Immunol. Methods* 134:43-50; Perkins et al., 1991 *Hum. Antibod. Hybridomas* 2:155-159; each of which is incorporated herein by reference). Out of 12 fusions (some fusions contained more than one positive EBV activated culture), 182 out of 456 initial hybridoma cultures exhibited reactivity with HCV E2 by IFA (yield 40% overall). Six additional fusions were performed on two of the original EBV-activated cultures that showed reactivity to HCV-E2 by Western blot. Hybridomas secreting HCV E2 antibodies reactive by Western blot (in addition to being IFA reactive) were isolated from two of the fusions. Overall, 30 human hybridomas were frozen. Limiting dilution clones were isolated from 12 parent hybridomas and HCV-HMAbs from 11 of the hybridomas were produced in bulk for subsequent studies. eight of the HCV HMAbs were $IgG_1$ with kappa light chains and two were $IgG_1$ with lambda light chains. HMAb CBH-9 was $IgG_1$ but it is not known whether it uses a lambda or kappa light chain. PCR and DNA sequence analysis of 10 of the HMAbs (the lone exception was HMAb CBH-9) confirmed that all of the HMAbs expressed distinct heavy and light chains. The fusion partners, IgG subtypes, and results obtained in IFA with the hybridomas are described in Table 3.

Example 4

HCV E2 ELISA

Figure 6:
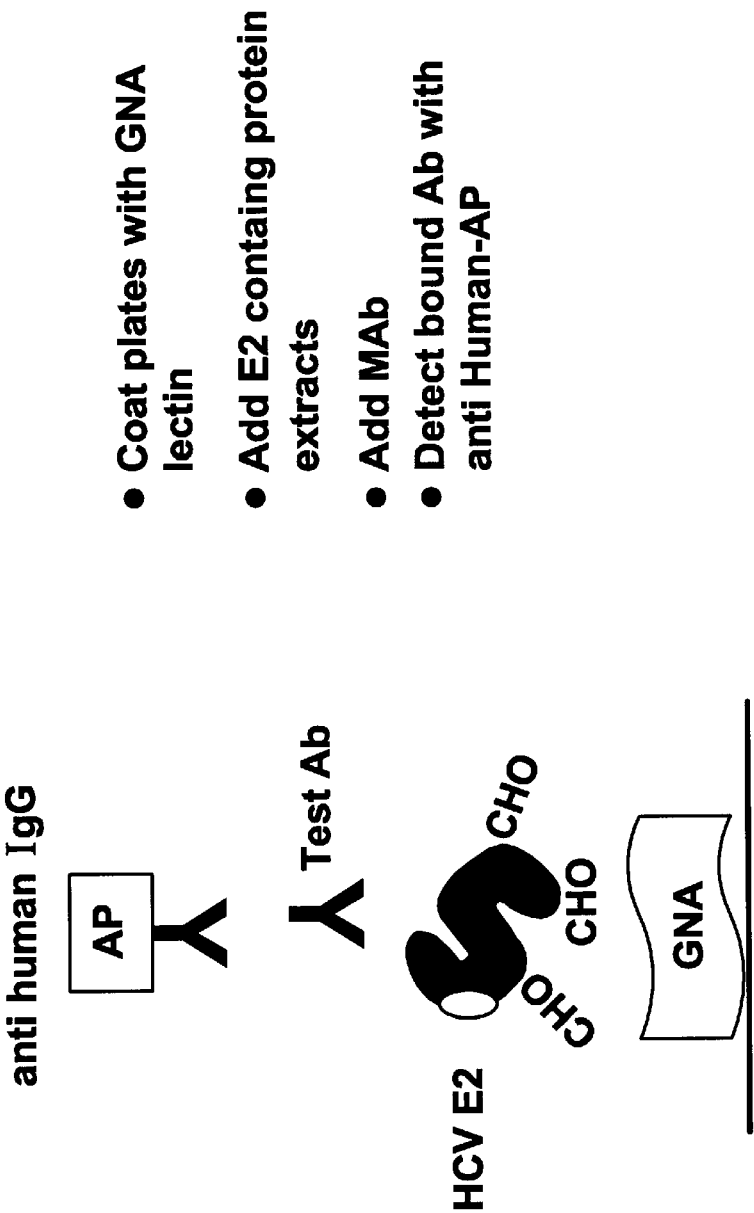

Previous studies indicated that the HCV E2 protein is highly glycosylated and can be bound by any one of several lectins including *Galanthus nivalis* (GNA), *Tiriticum vulgaris* (WGA), and *Ricinus communis* (Ralston et al., 1993, supra; da Silva Cardosa, 1998, supra; Sato et al., 1993 *Virology* 196:354-357; each of which is incorporate herein by reference). Therefore, the utility of the two lectins GNA and WGA as reagents was evaluated for capturing HCV E2 protein onto a microtiter plate. A schematic of this assay is depicted in FIG. 6.

Monolayers of HeLa cells were grown to 80% confluence and infected with 5 pfu/cell of VWA and 5 pfu/cell of recombinant vaccinia virus or 5 pfu of VWA only. HCV recombinant viruses were mixed with wild type vaccinia with an intact hemaglutinin gene to minimize the vaccinia virus induced cytopathic effect observed with hemaglutinin minus virus (Seki et al. 1990, *Virology* 175:372-384; incorporated herein by reference). Twenty-four hours after infection cells were harvested. Extracts were prepared by washing the cells with PBS and then resuspending $30 \times 10^6$ cells in 1 ml of lysis buffer (150 mM NaCl, 20 mM Tris pH 7.5, 0.5% deoxycholate, 1.0% Nonidet-P40, 1 mM EDTA, 0.5 mg/ml Pefabloc (Boehringer Mannheim, Indianapolis, Ind.), 2 µg/ml Aprotinin, 2 µg/ml Leupeptin, and 1 µg/ml Pepstatin). Nuclei were pelleted by centrifugation at 18,000×g at 4° C. for 10 minutes. Extracts were stored at 4° C. and used for ELISA within 24 hours of preparation.

TABLE 3

Characteristics and IFA reactivity of HCV HMAbs

| Antibody[a] | Hetero Myeloma | Subtype Heavy | Light | Immunofluorescence 1a | 1b | 2a | 2b |
|---|---|---|---|---|---|---|---|
| CBH-2 | $K_6H_6$/B5 | IgG1 | Kappa | ++ | ++ | ++ | ++ |
| CBH-4D | $K_6H_6$/B5 | IgG1 | Lambda | + | + | − | − |
| CBH-4B | $K_6H_6$/B5 | IgG1 | Kappa | ++ | ++ | +/− | − |
| CBH-4G | $K_6H_6$/B5 | IgG1 | Kappa | + | + | +/− | +/− |
| CBH-5 | H73C11 | IgG1 | Kappa | ++ | ++ | ++ | ++ |
| CBH-7 | $K_6H_6$/B5 | IgG1 | Kappa | ++ | ++ | ++ | ++ |
| CBH-8C | $K_6H_6$/B5 | IgG1 | Kappa | ++ | ++ | ++ | ++ |
| CBH-8E | $K_6H_6$/B5 | IgG1 | Kappa | ++ | ++ | ++ | ++ |
| CBH-9 | H73C11 | IgG1 | Unknown | + | + | +/− | +/− |
| CBH-11 | $K_6H_6$/B5 | IgG1 | Kappa | + | ++ | ++ | ++ |
| CBH-17 | $K_6H_6$/B5 | IgG1 | Lambda | + | ++ | − | − |
| R04 | | IgG1 | Lambda | − | − | − | − |

[a]Reactivity by IFA of HCV HMAbs with HeLa cells infected with recombinant vaccinia virus expressing HCV E2 of the indicated genotype.
Reactivity was scored ++ strongly positive;
+ positive;
+/− weakly positive;
− negative.
The heavy and light chain subtypes of the antibodies are provided.
R04 is an isotype matched control antibody.
Antibodies were tested at 10 µg/ml.

Microtiter plates (Maxisorp, Nalge Nunc International, Rochester, N.Y.) were prepared by coating individual wells with 500 ng of purified lectin in 100 µl of PBS for 1 hour at 37° C. Wells were then washed with TBS (150 mM NAC1, 20 mM Tris-HCL, pH 7.5), and blocked by incubation for 1 hour at room temperature with 150 µL BLOTTO (TBS plus 0.1% Tween-20, 2.5% normal goat sera, 2.5% non fat dry milk). Plates were washed two times with TBS followed by the addition of 20 µl of extract from vaccinia virus infected HeLa cells 1:5 with BLOTTO. After incubation for 1.5 hours at room temperature, plates were washed three times within TBS followed by addition of unlabeled antibodies at various concentrations in 100 µl of BLOTTO. Plates were incubated for 1.5 hours, wells were washed three times with TBS and 100 µl of anti-human alkaline phosphatase conjugate (Promega, Madison, Wis.) diluted 1/5000 in BLOTTO was added. After incubation for 1 hour at RT, the plates were then washed four times with TBS followed by incubation with a 1 mg/ml solution of p-nitrophenyl phosphate (PNPP). Substrate development was allowed to proceed for 30 to 45 minutes, then the absorbance of the wells at 405 nm was determined using a multiwell plate reader (Du Pont Co., Wilmington, Del.).

Figure 7:
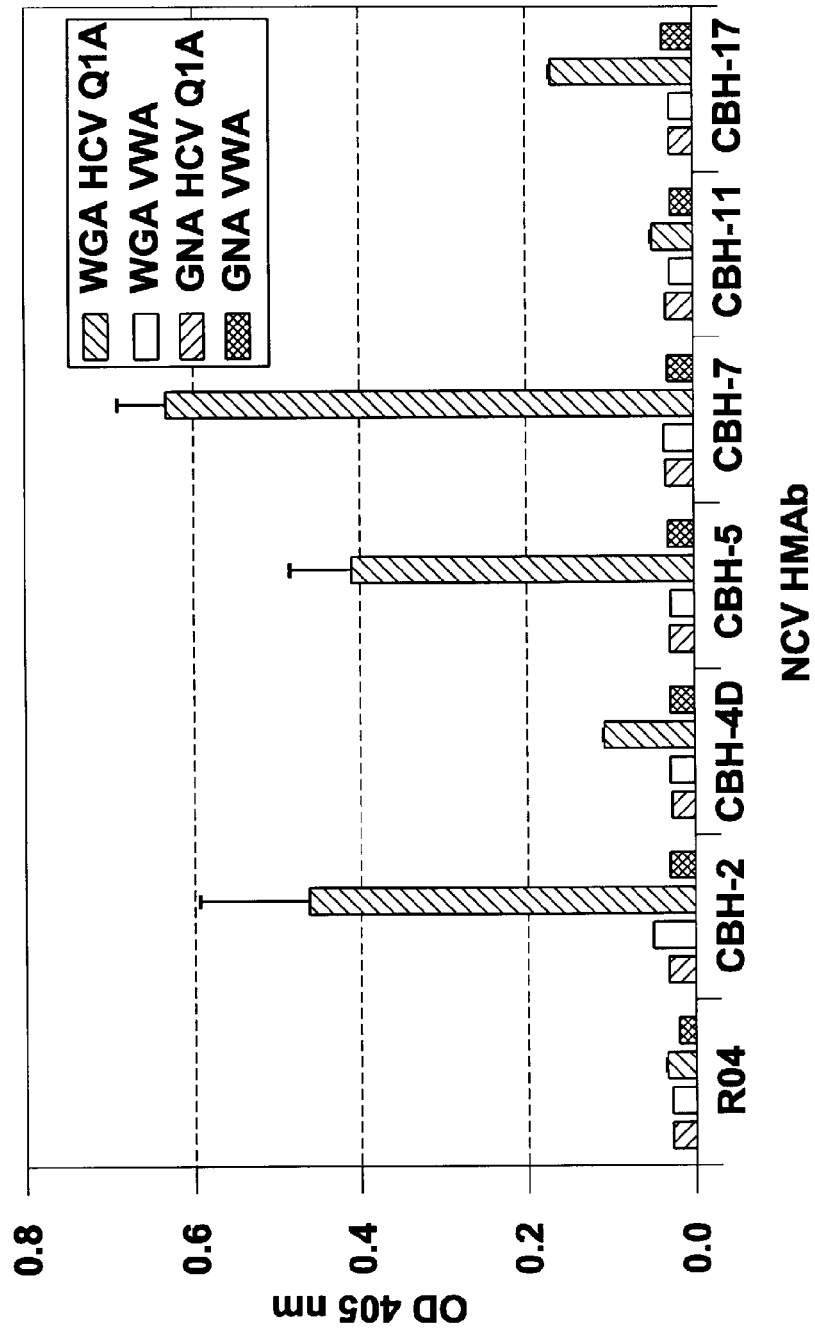

HCV 1a E2 produced by recombinant Q1a vaccinia virus was employed as a source of HCV E2 and six HCV HMAbs were employed as detection reagents (FIG. 7). No reactivity was observed to proteins captured with either lectin with a control monoclonal and only background levels of reactivity were observed for all HCV HMAbs with proteins captured by WGA. In contrast, HCV HMAbs CBH-2, CBH-5, CBH-7 all exhibited strong reactivity to proteins captured by GNA. Additionally HCV HMAbs CBH-17 and CBH-4D had lower levels of reactivity with GNA captured proteins. This suggests that HCV HMAb CBH-11 does not recognize this particular E2. However it is clear that the GNA capture ELISA is extremely useful for analyzing the reactivity of HMAbs with HCV E2.

Figure 8B:
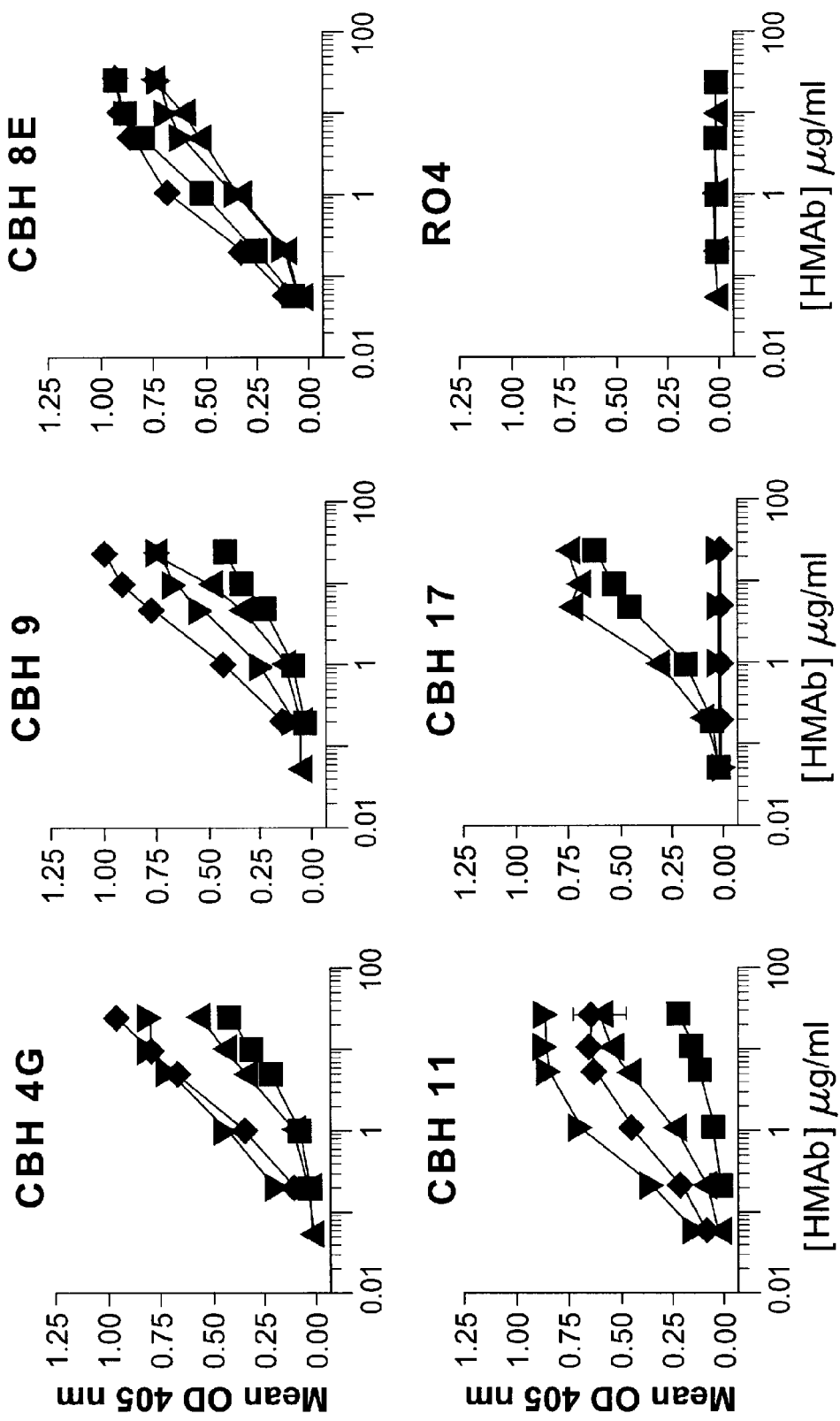

Therefore the reactivity of the HCV HMAbs was then evaluated with recombinant vaccinia virus expressing E2 proteins of divergent genotypes (FIG. 8). All 11 HCV HMAbs bound to two or more of the HCV E2 constructs and no specific signal was obtained with a control HMAb (Panel marked R04). The HMAbs with the highest relative affinity and levels of reactivity to E2 proteins of all four genotypes were CBH-7 and CBH-8C followed by HMAbs CBH-5, -2, and -8E. HMAbs CBH-4G and CBH-9 exhibited significantly greater reactivity to HCV E2 proteins of genotypes 2a and 2b, while HMAb CBH-11 was markedly less reactive with Q1a E2 protein. HMAb CBH-17, and to a lesser extent CBH-4D and CBH-4B, exhibited preferential binding to E2 proteins of genotype 1a and 1b relative to E2 proteins of genotypes 2a or 2b. These variations were not a result of varying efficiencies of capture of the different E2 proteins since the maximum signals obtained with the different E2 proteins since the maximum signals obtained with the different E2 proteins were very comparable in all experiments. These results were consistent with the results obtained in IFA with the same constructs (See Table 3, above). Seven antibodies, CBH-2, -4G, -5, -7, -8C, -8E, and -9, exhibited significant reactivity with all tested HCV E2 constructs and can be considered broadly reactive.

Figure 9:
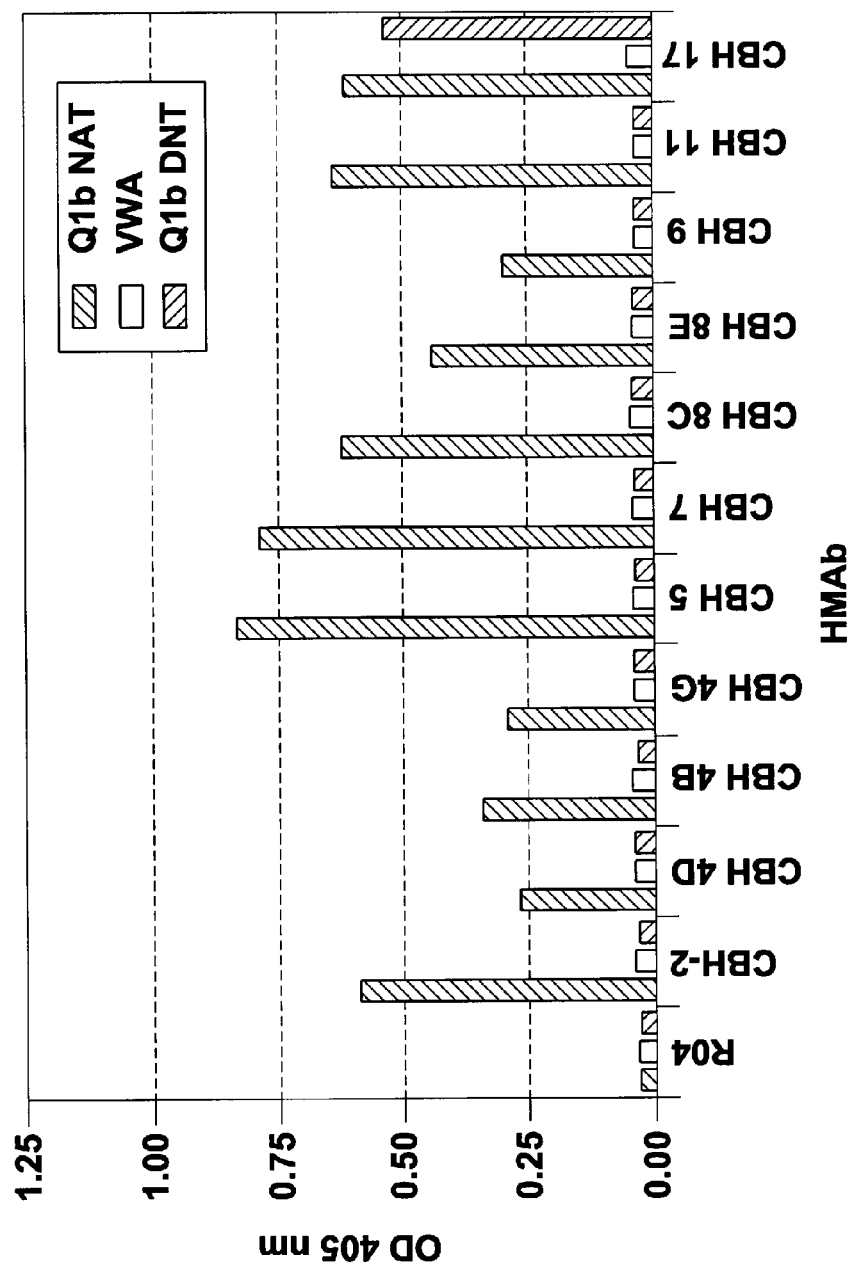

The reactivity of all tested HMAbs with at least two HCV genotypes suggested that the epitopes recognized by the HCV HMAbs would be highly conserved (See FIG. 9). It was of interest to determine whether the epitopes recognized by the HMAbs would be conformational or linear in nature. This was addressed directly by comparing the reactivity of the HCV HMAbs to both native and denatured HCV E2 proteins (See FIG. 9). As expected all 11 HCV HMAbs recognize HCV 1b E2. Treatment of HCV E2 by heating to 56° C. in the presence of 0.5% SDS and 5 mM dithiothreitol results in complete abrogation of reactivity for 10 of the 11 HCV HMAbs. The sole exception is HMAb CBH-17, which retains approximately 90% of its reactivity with the denatured E2 protein. Western Blot analysis of the HMAb CBH-17 confirmed it was weakly reactive with HCV envelope proteins expressed by vQ1a, or vQ1b (data not shown). No reactivity with Western blotted vQ1a was observed with any of the remaining 10 HMAbs (data not shown). Thus 10 of the 11 HCV HMAbs recognize conformational epitopes.

Figure 10:
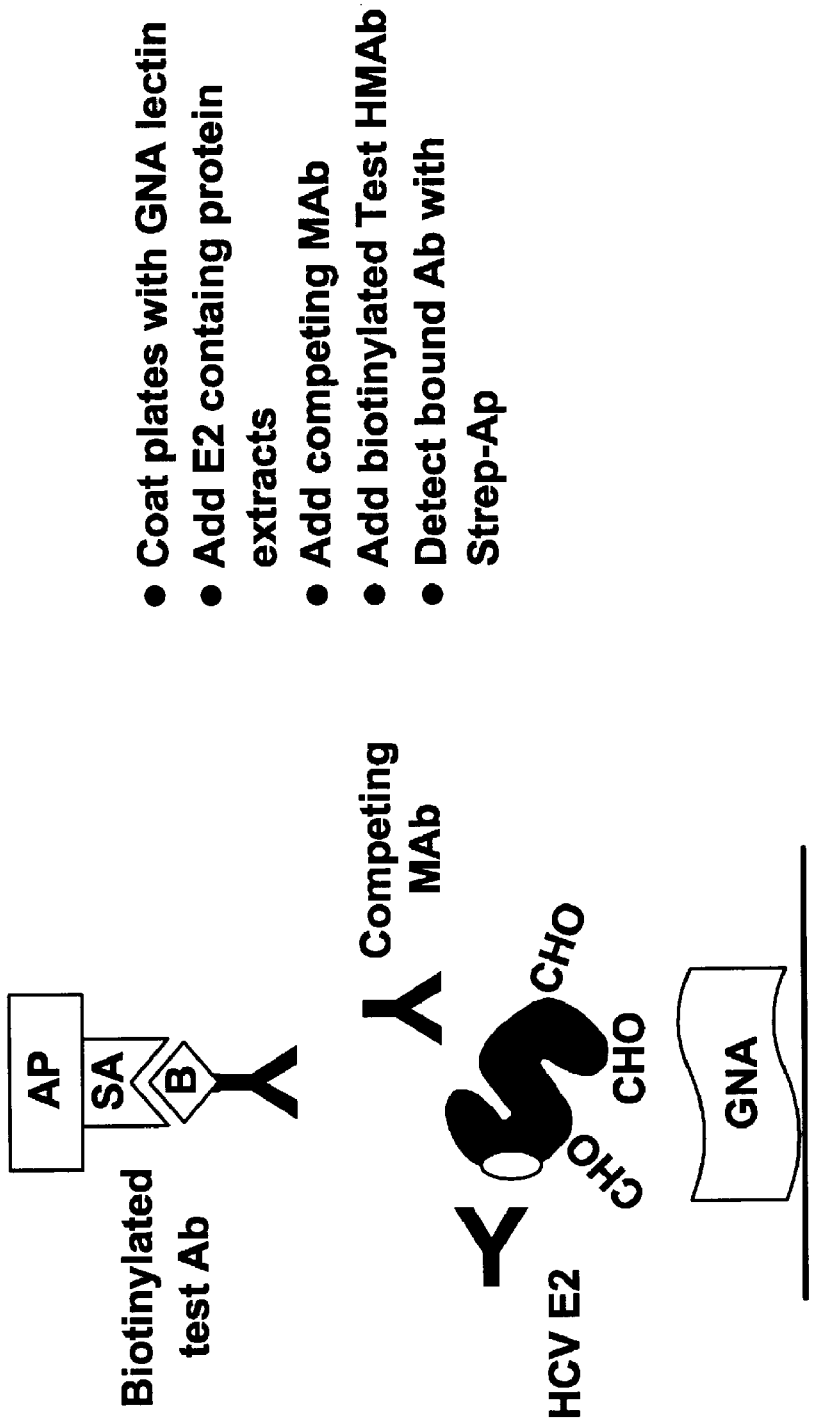
Figure 11:
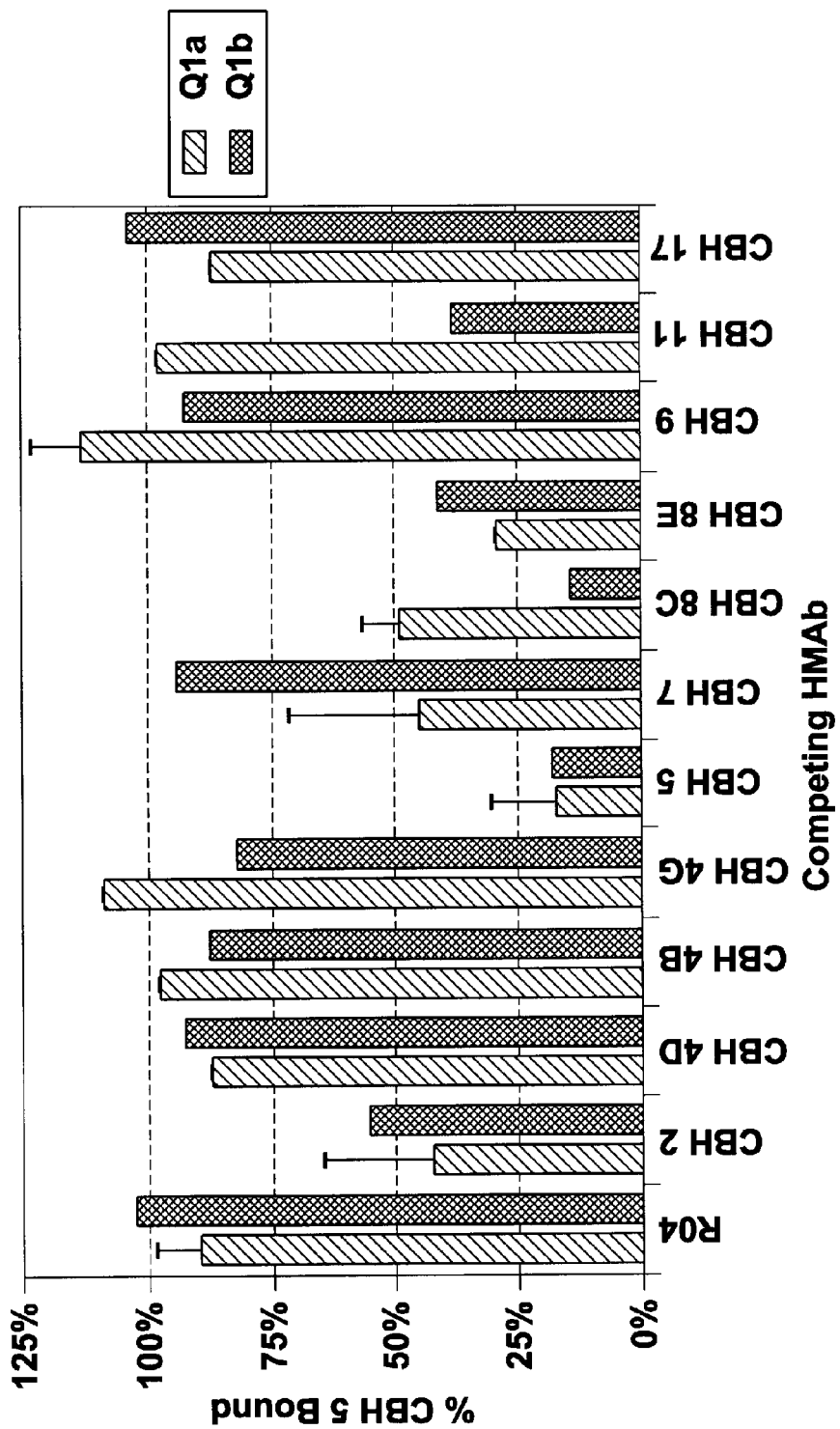

Lastly, competition analyses were employed to define which HCV HMAbs recognize the same (or very spatially close) epitopes. A schematic of this assay is depicted in FIG. 10. The HCV HMAbs CBH-5, CBH-2, and CBH-7 were biotinylated using standard methods and the reactivity of the biotinylated HMAbs to HCV type 1 or type 2 E2 in the presence of an excess of selected HMAbs was compared to those seen in samples without any added antibody. As seen in FIG. 11, the control HMAb R04 and the HCV HMAbs CBH-4D, -4B, -4G, -7, -9, and -17 all exhibited essentially no inhibition of HMAb CBH-5 binding. In contrast HMAb CBH-5 was inhibited 85% by an excess of itself and approximately 75% by HMAb CBH-8E. HMAb CBH-5 was inhibited more variably by HMAbs CBH-8C and CBH-11 and only inhibited to approximately 50% by HMAb CBH-2. In particular, the competition seen with HMAb CBH-2 is relatively equivocal, and it is not clear whether CBH-2 recognizes the same epitope as CBH-5 at a reduced affinity, or recognizes a separate spatially close epitope.

Figure 12:
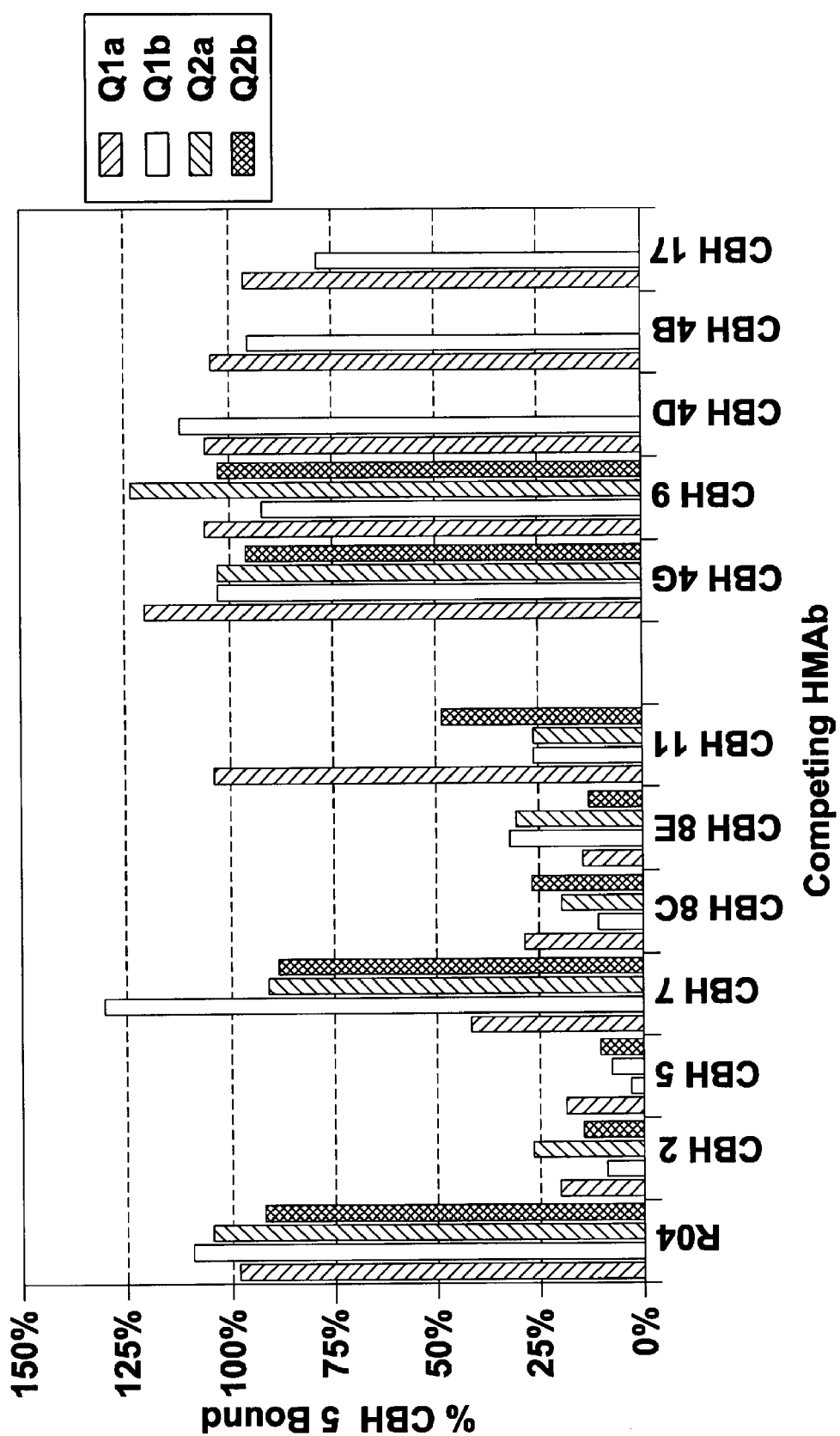
Figure 13:
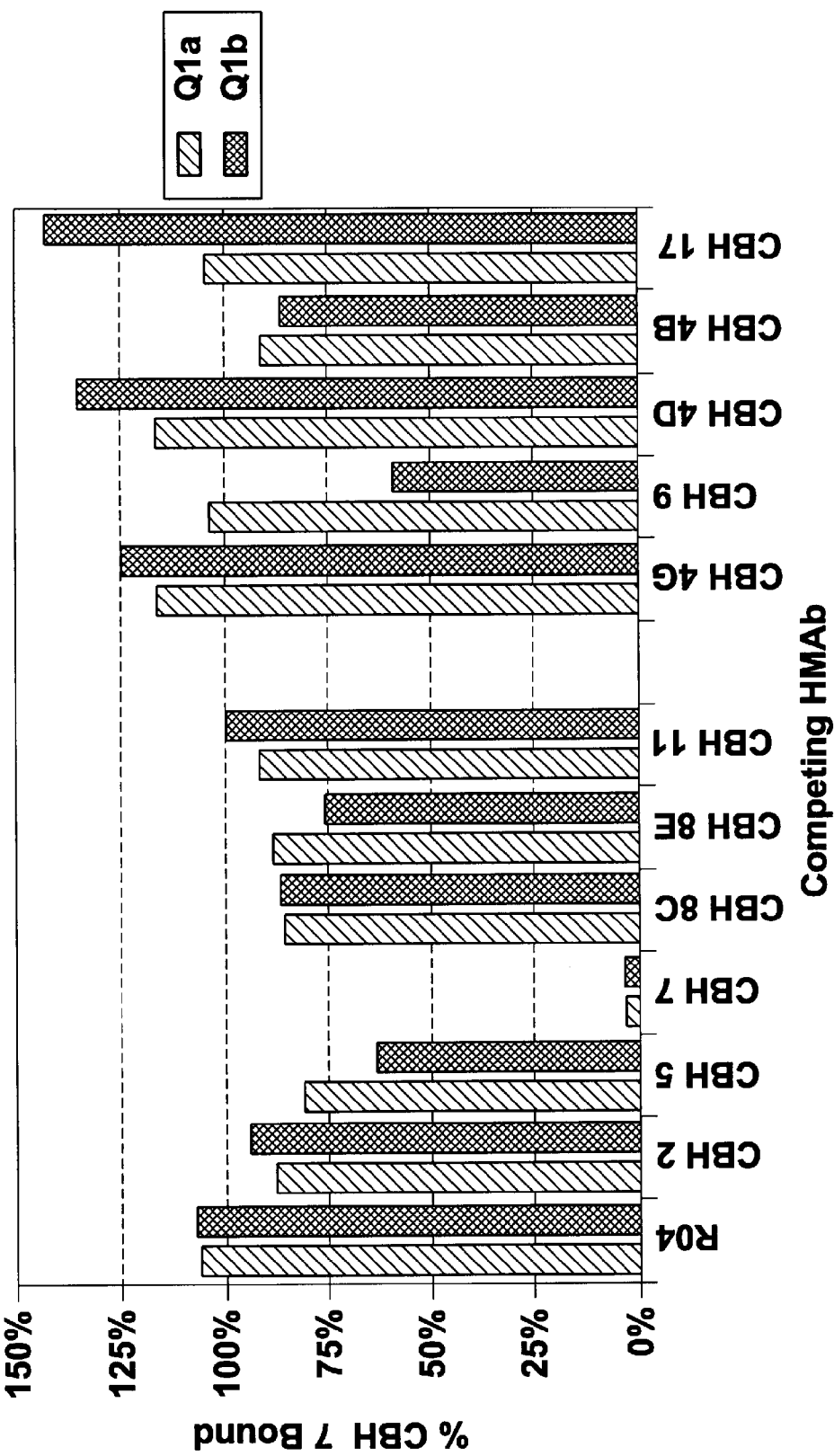
FIG. 13 is a competition analysis showing that HCV HMAb CBH-7 recognizes a unique epitope. HCV E2 protein from cytoplasmic extracts of HeLa cells infected with vaccinia virus Q1a (blue bars) or Q1b (red bars) was captured with 500 ng of GNA lectin. Bound HCV E2 was detected with 2 µg/ml of biotinylated CBH-7 in the presence of 20 µg/ml of the indicated HMAbs (x axis). The bars indicate the binding observed in the presence of the indicated antibody relative to binding of biotinylated CBH-7 to HCV E2 in the absence of any competing antibody (y axis). R04 is a control HMAb that recognizes a cytomegalovirus protein. Bars indicate the mean value obtained from replicate wells. Error bars indicate one standard deviation from the mean.

Analysis of the antibody competition with HMAb CBH-2 (FIG. 12), indicated that HMAb CBH-2 binding was inhibited to greater than 75% by itself and HMAbs CBH-5, -8C, and -8E. In contrast, CBH-7 inhibited binding to only Q1a proteins by 60%, and CBH-11 inhibited binding only to Q1b and Q2a proteins. As with HMAb CBH-5, no competition was observed with HMAbs CBH-4G, -4D, -4B, -9, or -17. Analysis of competition results with HMAb CBH-7 (FIG. 13) indicate that the only HMAb that significantly inhibited binding of CBH-7 was itself. These data demonstrate that among the broadly reactive HMAbs, CBH-2, -5, -11, and -7 all recognize distinct epitopes. The possibility remains that CBH-2, -8C, and -8E may recognize either the same epitope or two distinct epitopes. Additionally CBH-9, and CBH-4G may recognize the same epitope or two distinct epitopes, but their failure to compete with CBH-2, -5 etc. ensures that they do not recognize the same epitope(s) as the other broadly reactive HMAbs. Thus, minimally the broadly reactive HMAbs recognize five distinct epitopes.

Example 5

Assessment of E2-Specific HMAb Activity in the Neutralization of Binding Assay

The neutralization of binding (NOB) assays tests whether a given antibody or serum can prevent the binding of HCV E2 protein to a putative receptor, expressed on human T cell lines. The NOB assays were performed using methods and HCV E2 proteins previously described (Rosa et al., supra; Ishii et al., supra). Briefly, 1 µg of the HCV E2 1a protein produced in mammalian cells (Rosa et al., supra) was mixed with serial dilution of antibodies (from 0.1 to 300 µg/ml) and incubated for 30 min. at 37° C. Molt-4 cells ($10^5$) were added to the mixture and incubated on ice for 1 hour. After washing, the amount of HCV-E2 bound to Molt-4 cells was assessed by flow cytometry as described previously (Rosa et al., supra). The NOB titer is defined as the serum dilution that shows 50% neutralization of E2 binding.

The ability of HMAbs to inhibit binding of HCV 1a E2 to CD81 expressing target cells was assessed with the neutralization of binding (NOB) assay (Rosa et al., supra). HMAbs CBH-4D, 4B, 4G, and 17 did not block the binding of E2 to target cells at concentrations of less than 25 µg/ml. HMAbs CBH-2, -5, -7, -8C, -8E, and -11 achieved 50% inhibition at concentrations of 1 to 10 µg/ml in multiple experiments (Table 4).

Example 6

Effect of HCV HMAbs on E2 Binding to CD81: Microtiter Plate Assays

Figure 14:
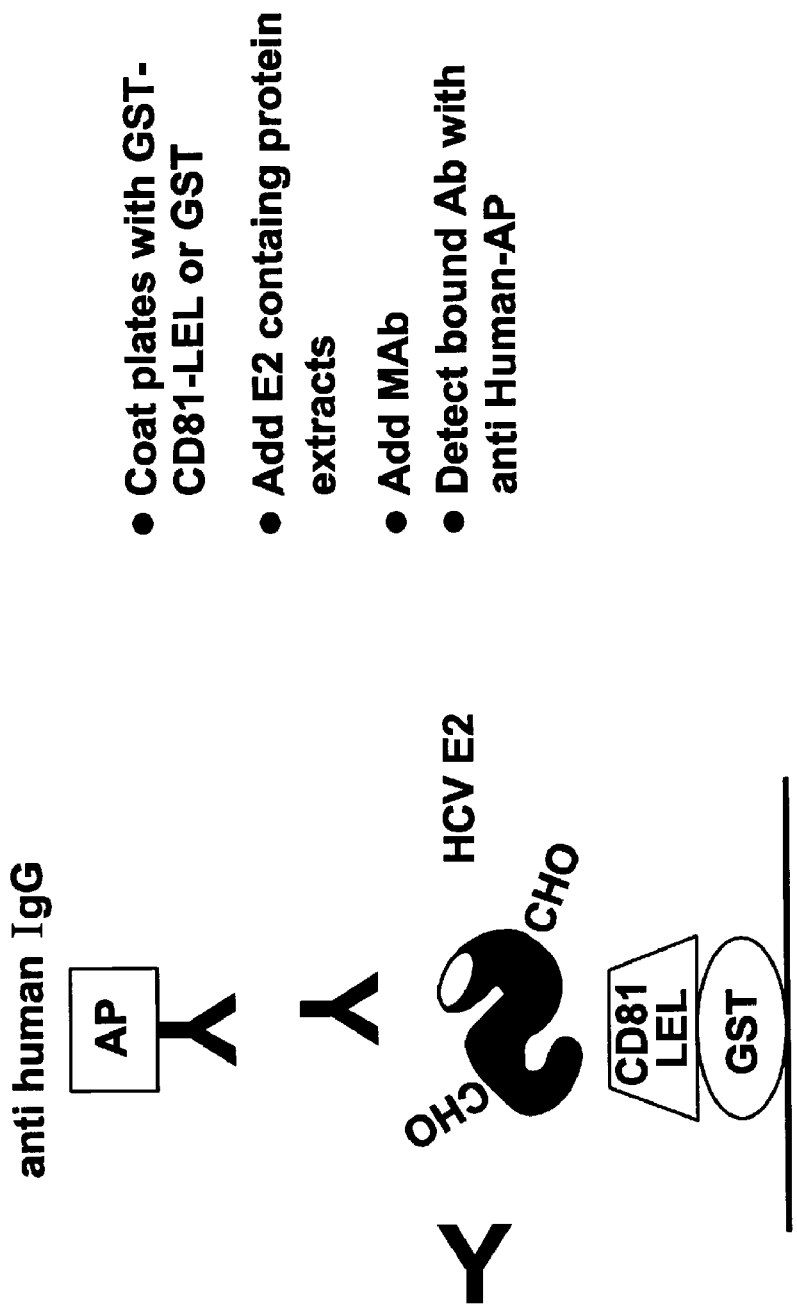
FIG. 14 depicts a schematic for assessing the ability of antibodies to block CD81 binding to E2 proteins as employed in the experiments described in FIG. 1. Recombinant CD81 is coated onto a solid surface. E2-containing protein extracts are then either added directly, or after preincubation with the test antibody. Bound test antibody-E2 complexes are detected using an appropriate labeled secondary antibody.

Recently, the human tetraspannin protein CD 81 has been identified as a potential receptor for HCV and the cellular target protein for HCV E2 in the NOB assay. The binding site for HCV E2 within CD81 has been localized to the large extracellular loop, CD81-LEL (Pileri et al., 1998 *Science* 282:938-941; incorporated herein by reference), previously referred to as extracellular loop 2 or LEL. To prevent confusion between E2 and LEL we have opted to refer to this region as the Large Extracellular Loop (LEL). The large extracellular loop of human CD81 (CD81-LEL) was expressed as a fusion protein with glutathione-S-transferase employing the pGEX vector (GST-2T). Construction and purification of the protein were as described (Flint et al., 1999 *J. Virology* 73:6235-6244; incorporated herein by reference). This CD81-LEL-GST fusion protein was used to determine which HMAbs could recognize CD81-HCV E2 complexes. A schematic of this assay is provided in FIG. 14. Microtiter plate wells were coated with 100 ng of purified CD81-LEL or non-recombinant GST diluted in PBS. After 2 hours at 37° C., wells were washed one time with TBS and blocked by incubation with 150 µl of BLOTTO for 1 hour at RT. Extract from BSC 1 cells infected with HCV E2 expressing vaccinia virus was combined with test antibody in 100 µl of BLOTTO in coated plates that were incubated overnight with gentle agitation at 4° C. Wells were then washed three times with TBS followed by adding appropriate alkaline-phosphate conjugated secondary antibody and PNPP substrate as described in Example 4.

To confirm the NOB results using E2 proteins of multiple genotypes, we assessed whether the HCV HMAbs could inhibit the interaction of HCV E2 with CD81. Microtiter plates were first coated with purified CD81-LEL glutathione-S-transferase fusion protein to which an excess HCV E2 was added in the presence of the HCV HMAbs. Because HCV E2 binds specifically to human CD81 but not CD81 proteins of most other primates (Rosa et al., supra), the E2 proteins were produced in the green monkey kidney cell line BSC-1 to minimize the effect of endogenous CD81. Both anti-HCV and control antibodies were not captured by purified non-recombinant glutathione-S-transferase. Nor were the HCV or control antibodies captured by CD81 when combined with extracts of BSC-1 cells infected with wild type vaccinia virus (data not shown).

Figure 15:
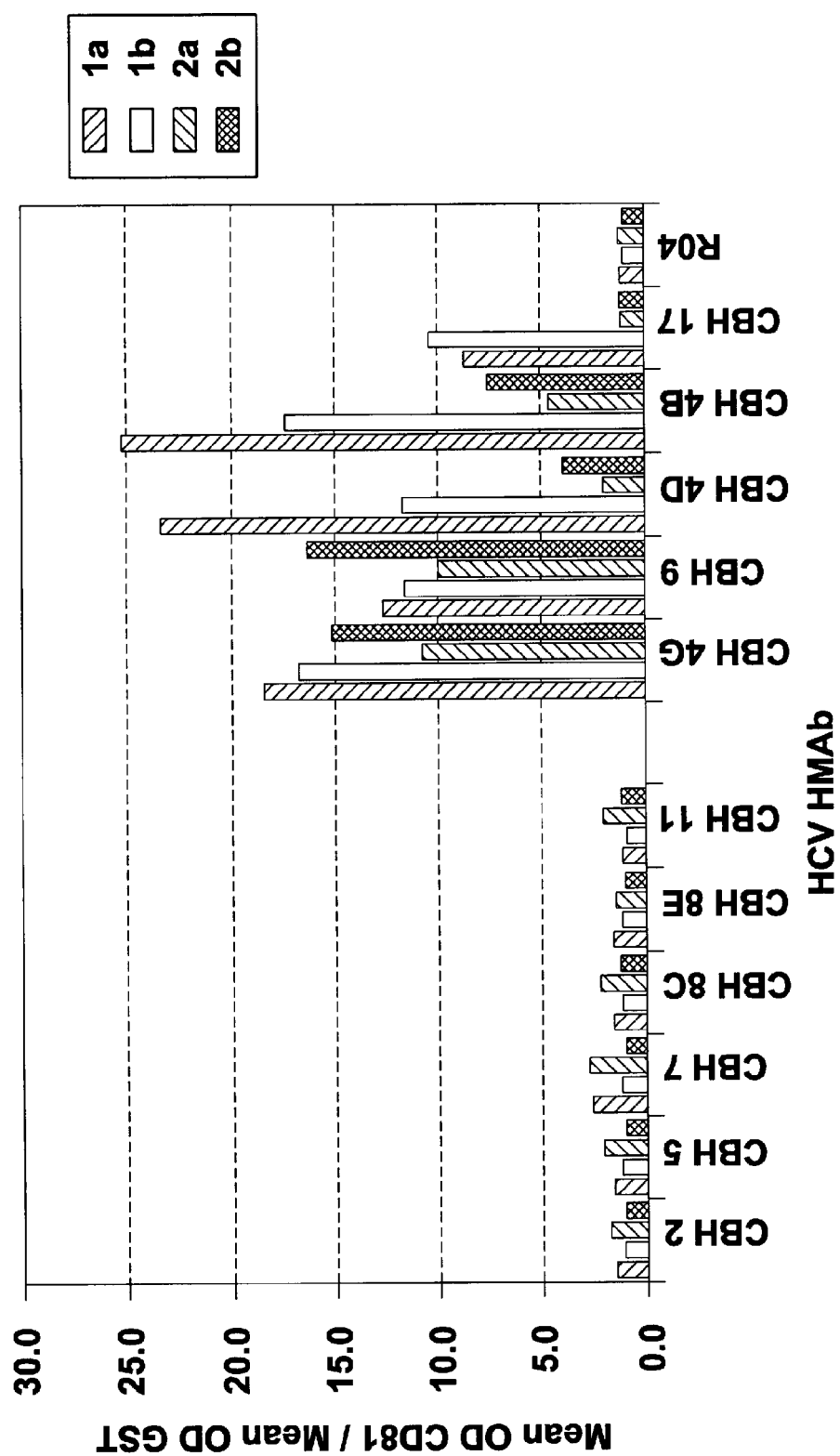
FIG. 15 is a bar graph that demonstrates that a subset of HCV HMAbs react with HCV E2 when bound to CD81-LEL. Extracts from BSC-1 cells infected with recombinant vaccinia virus expressing HCV E2 proteins were combined with 5 µg/ml of the indicated HMAbs (x axis) in a total volume of 100 µl and incubated in microtiter plate wells coated with 100 ng of a GST CD81-LEL fusion protein or non-recombinant GST overnight. Wells were washed and bound antibody was detected using an appropriate alkaline-phosphate conjugated secondary antibody and PNPP substrate as further described in Example 6. Values are the mean OD value of antibody captured by CD81 divided by the mean OD value for antibody captured by GST in the presence of 1a (purple bars), 1b (red bars), 2a (yellow bars), or 2b (green bars) E2 protein. OD values obtained from wells coated with GST ranged between 0.021 and 0.081.
Figure 16:
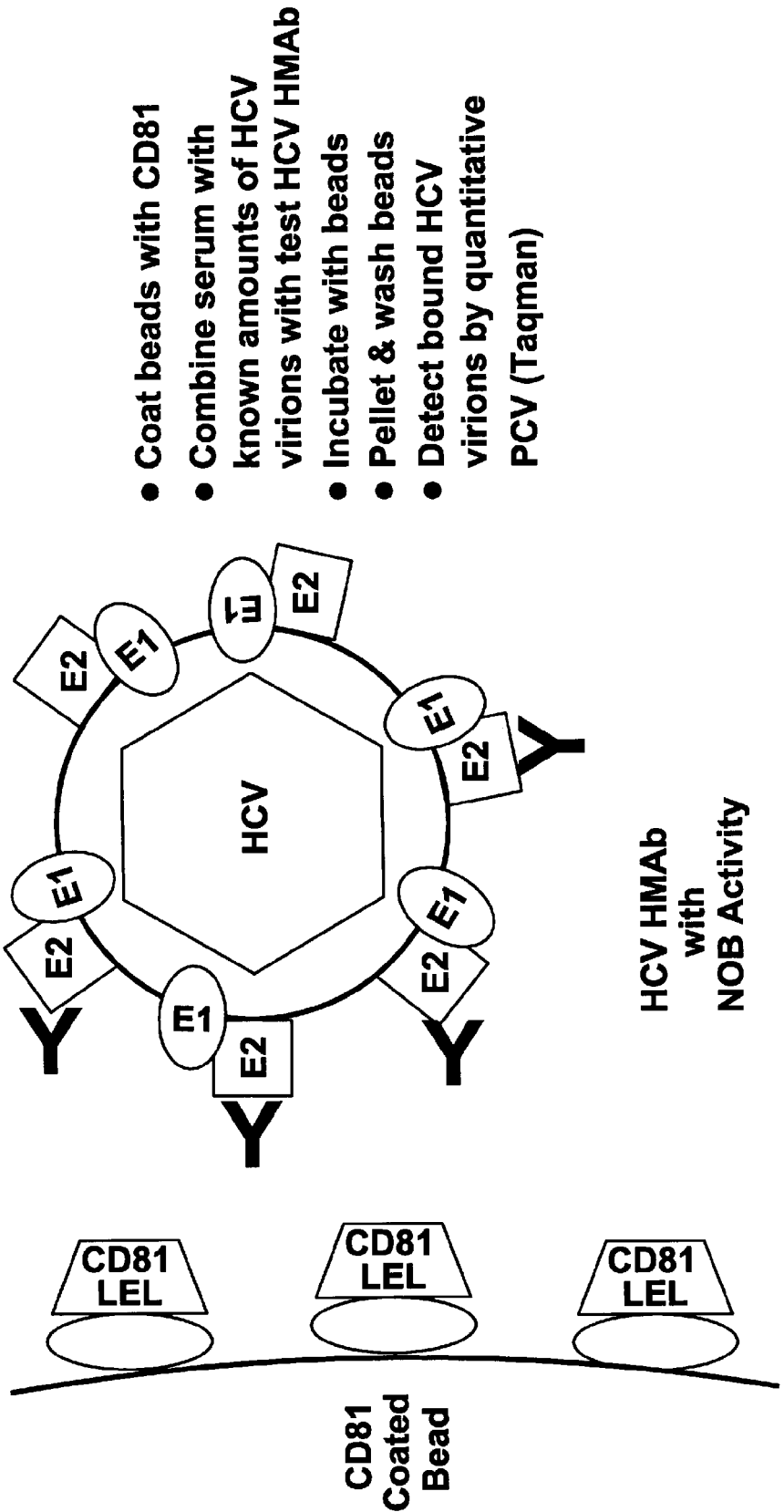
FIG. 16 depicts a schematic for assessing the ability of antibodies to block CD81 binding to HCV virions as employed in the experiments described in FIG. 17. Recombinant CD81 is coated onto a solid surface. HCV virions are preincubated with test antibodies, and then allowed to bind to immobilized CD81. Detection of bound HCV virions is measured by quantitative PCR.
Figure 17:
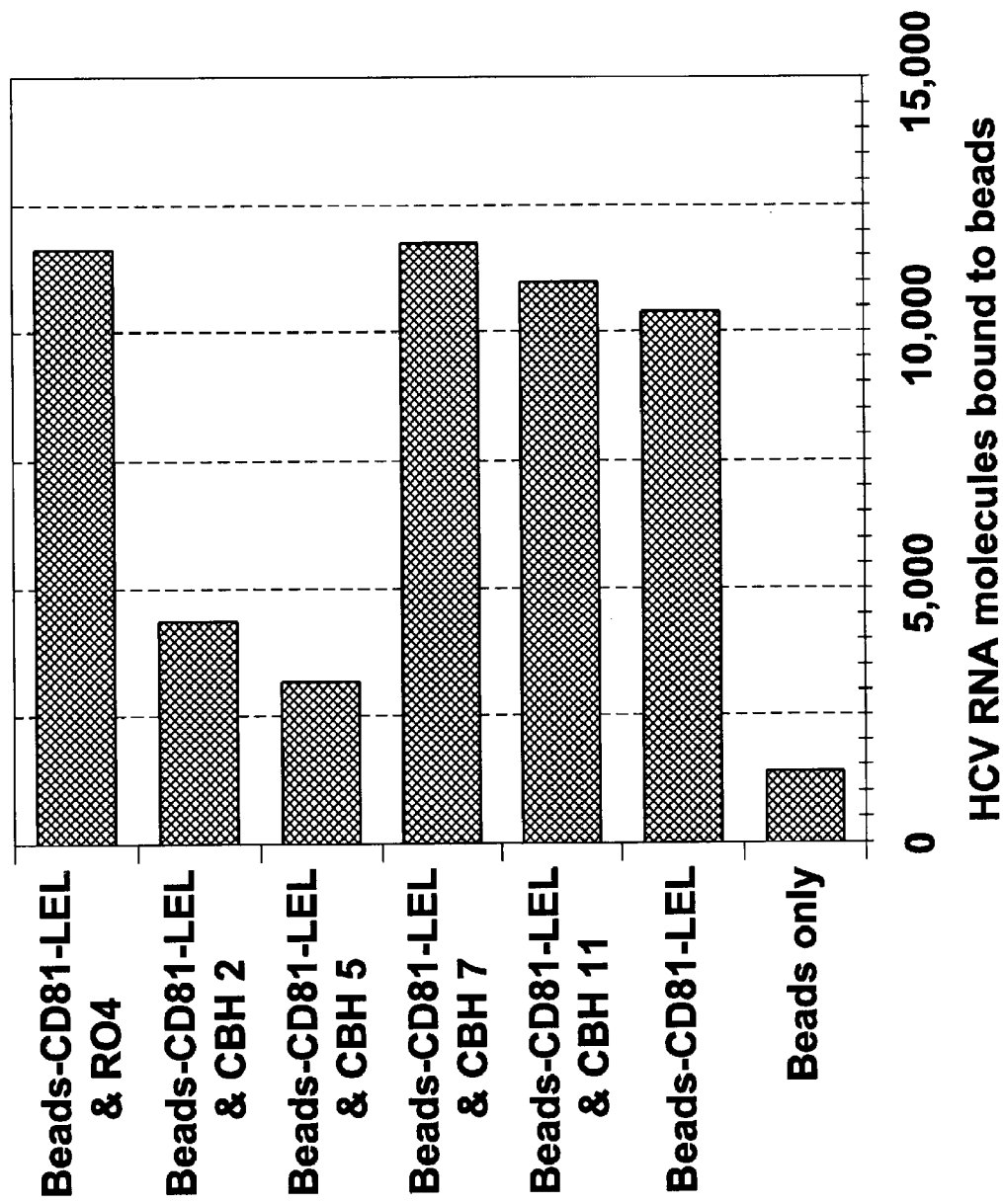
FIG. 17 shows a bar graph demonstrating that HMAbs CBH-2 and CBH-5 inhibit binding of HCV virions to CD81. The number of HCV RNA molecules bound to polystyrene beads (x axis) after HCV 1a chimpanzee serum was combined with 10 µg of the indicated antibodies (y axis) and then allowed to bind to beads coated with CD81-LEL.

The NOB negative HMAb CBH-4G was captured onto CD81 coated plates to equivalent extents with E2 proteins of all four genotypes tested. The HMAbs CBH-4B, -4D and -17, were captured to variable extents onto CD81 coated plates by HCV 1a or 1B E2 proteins but not HCV 2A or 2B E2 proteins, consistent with the reactivity of these HMAbs with GNA captured E2 protein (FIG. 15). Titration analysis of the four NOB negative HMAbs confirmed that they all bound to HCV 1b E2 protein with 50% of maximum binding is obtained at concentrations between 1 and 10 µg/ml (Table 4). None of the NOB positive antibodies, CBH-2, -5, -7, -8C, -8E, and -11 were captured by CD81 and E2 proteins of any of the our genotypes tested (FIG. 15). Similar results were obtained when the HCV antibodies were added to wells on which HCV 1b E2 protein was already bound to CD81-LEL (data not shown) indicating that the results obtained were independent of each other of addition of the E2 protein and the HCV HMAbs. Titration analysis of HMAbs CBH-2 and 7, which are strongly reactive with GNA captured E2 but negative with CD81 bound E2, confirmed that these antibodies did not bind to CD81-LEL E2 complex at concentrations of up to 25 µg/ml (data not shown). Thus, six HMAbs inhibited the binding of HCV E2 of multiple genotypes to CD81-LEL.

TABLE 4

Inhibition of HCV E2-CD81 Binding by Anti-HCV HMAbs

| HMAb | NOB 1a[a] | CD81 1b E2[b] |
|---|---|---|
| CBH 2 | 5 µg/ml | – |
| CBH 5 | 2 µg/ml | – |
| CBH 7 | 7 µg/ml | – |
| CBH 8C | 10 µg/ml | – |
| CBH 8E | 8 µg/ml | – |
| CBH 11 | 3 µg/ml | – |
| CBH 4G | – | 3 µg/ml |
| CBH 9 | – | 1 µg/ml |
| CBH 4B | – | 0.4 µg/ml |
| CBH 4D | – | 2 µg/ml |
| CBH 17 | – | 3 µg/ml |
| R04 | – | – |

[a] HMAb reactivity in representative NOB assays are presented as µg/ml of antibody that results in 50% inhibition of E2 binding to CD81 expressing T cells. Antibodies were tested at concentrations that ranged from 0.1 to 300 µg/ml. (–) = negative.
[b] HMAb reactivity is presented as the concentration of antibody (in µg/ml) that results in 50% of maximum binding to E2 captured by GNA or E2 captured by a CD81-LEL. (–) = negative.

Example 7

Microtiter Plate Assay for HCV Neutralizing Antibodies

To assist in the treatment and management of individuals with HCV infection, it would be desirable to know whether they have a potent anti-viral immune response. Although several assays that can measure neutralizing antibody titers have been described, including the neutralization of binding assay described above and ex vivo neutralization prior to inoculation of chimpanzees these assays are all cumbersome and are not suited to testing large numbers of samples. Therefore we employed HMAb CBH-4G, which is equivalently reactive to HCV E2-CD81 complexes with E2 proteins of multiple genotypes in an inhibition assay to determine the level of neutralizing of binding like antibodies in human sera. Individual wells of microtiter plates were coated with either 500 ng of purified GNA lectin or 100 ng of GST-CD81-LEL fusion protein for one hour at 37° C. Wells were then washed one time with TBS and blocked for one hour with 150 µl of BLOTTO at room temperature. The wells are then washed one time with TBS, and various dilutions of test sera or monoclonal antibodies were added to the appropriate wells in a total volume of 50 µl. At the same time 15 µl of HCV E2 protein containing extract was combined with 4 µg/ml of a biotinylated preparation of HMAb CBH-4G in a total volume of 50 µl of BLOTTO for each well. After incubation for 20 minutes at 4° C. the E2 CBH-4G mixture was added to microtiter plate wells already containing the test antibody. The entire plate was then incubated overnight at 4° C. with gentle agitation. The next morning the contents of the wells were discarded and the wells washed three times with TBS. This was followed by the addition of 100 µl of strepavidin conjugated alkaline phosphatase (Amersham-Pharmacia, Piscataway N.J.) diluted 1/1000 in PBS plus 0.1% Tween-20 (Sigma, St Louis Mo.). The plates were then incubated for one hour at room temperature after which time the wells were washed four times with TBS and bound biotinylated antibody detected by incubation with PNPP substrate as described in examples 2 and 4 above.

Figure 18:
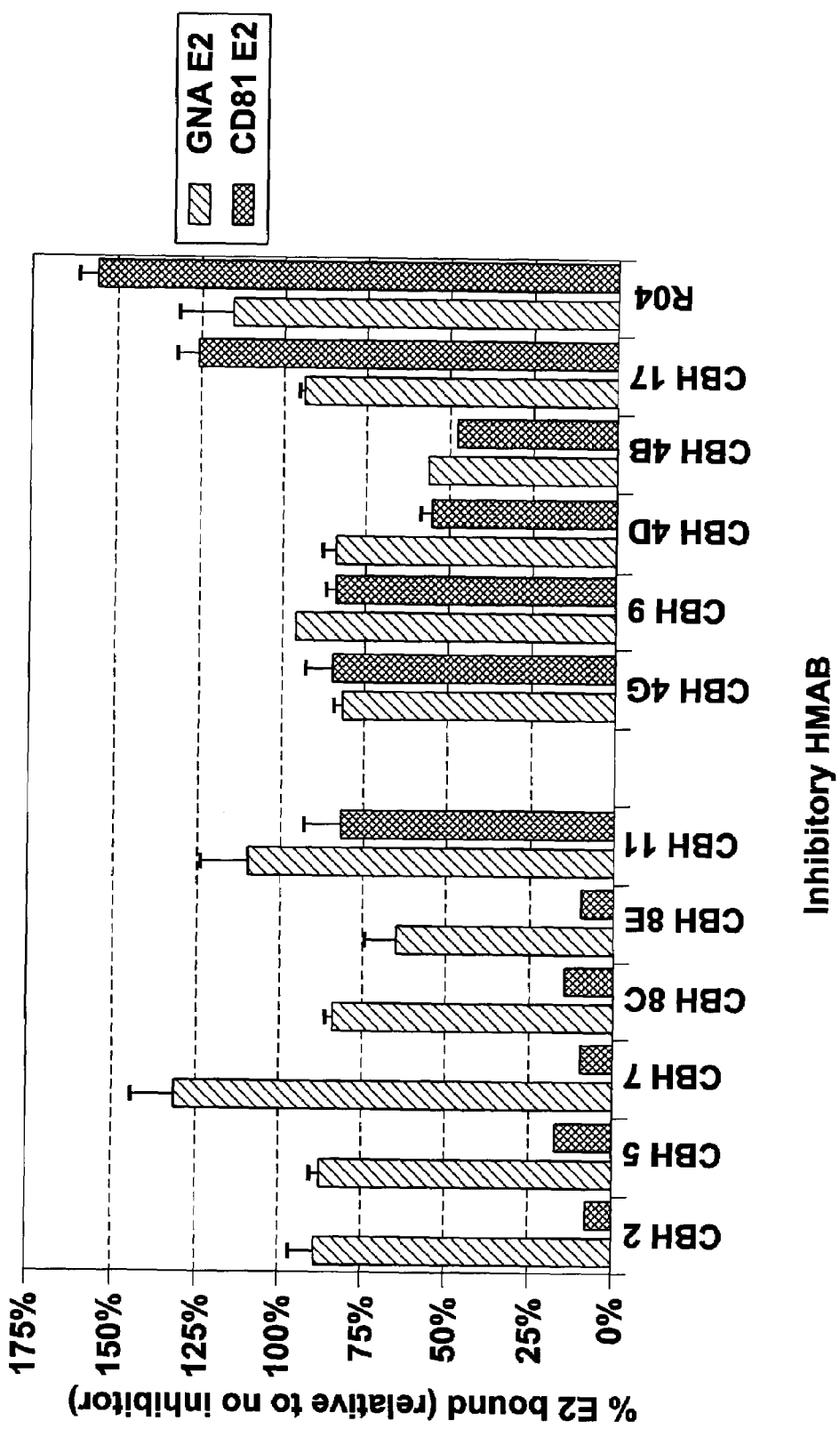
FIG. 18 is a bar graph that shows that HMAb CBH-4G can be employed to detect the presence of antibodies that inhibit binding of HCV E2 to CD81. HCV 1a E2 protein derived from extracts of BSC-1 cells infected with vaccinia virus Q1a was incubated with 4 µg/ml of a biotinylated preparation of HMAb CBH-4G for 20 minutes at 4° C. A 50 µl aliquot of the E2-CBH-4G complexes was then added to wells coated with either 500 ng of GNA (blue bars) or 100 ng of GST-CD81-LEL (red bars) to which 50 µl of a 40 µg/ml of the indicated antibodies (x axis) was added. R04 is a control HMAb that recognizes a cytomegalovirus protein. After an overnight incubation at 4° C. the wells were washed and bound biotinylated CBH-4G detected as described in Example 7. The bars indicate the mean signal obtained from duplicate wells in the presence of the indicated antibody relative to the signal obtained in the absence of any competing antibody. Error bars indicate one standard deviation from the mean.

The results obtained when the panel of 11 HCV HMAbs was used as test antibodies are presented in FIG. 18. In this experiment the ability of a 20 µg/ml concentration of the HCV HMAbs to inhibit the binding of HCV genotype 1a E2 protein to human CD81-LEL was evaluated. Inhibition of binding observed in CD81-LEL coated wells are compared to results obtained with the same antibody in GNA lectin coated wells. Inhibition observed of E2 binding in GNA coated wells reflects inhibition of the interaction between the CBH-4G detection antibody and the competing antibody. Inhibition observed specifically in the CD81-LEL coated wells reflects inhibition of the interaction between CD81 and E2. None of the 11 HCV HMAbs or the control antibody, R04 exhibited more than 50% inhibition of CBH-4G binding to E2 captured by GNA. In contrast five of the six HCV HMAbs previously shown to be neutralization of binding positive strongly inhibited binding of CBH-4G-E2 complex to CD81-LEL. The lone exception was HMAb CBH-11, which does not efficiently recognize the Q1a isolate of genotype 1a E2 protein. The HMAbs CBH-4-b, -4G, -4D, -9 and -17, which recognize CD81-LEL-E2 complexes all minimally effected binding of CBH-4G bound E2 to CD81-LEL. Thus HMAb CBH-4G can effectively discriminate between antibodies that can or cannot inhibit the interaction of HCV E2 with CD81.

TABLE 5

Preliminary epitope analysis of HCV HMAbs

| Epitope | Type[1] | HMAb | Inhibits E2-CD81[2] | Binds to HCV Virion | Comp w CBH 2 | 1a | 1b | 2a | 2b |
|---|---|---|---|---|---|---|---|---|---|
| 1 | CONF | CBH 2 | + | + | + | + | + | + | + |
|  |  | CBH 8Ec | + | ND | + | + | + | + | + |
| 2 | CONF | CBH 5 | + | + | +/−[3] | + | + | + | + |
| 3 | CONF | CBH 7 | + | − | − | + | + | + | + |
| 4 | CONF | CBH 11 | + | − | + | − | + | + | + |
| 5 | CONF | CBH 8C | + | NDn | + | + | + | + | + |
| 6 | CONF | CBH 4G | − | ND | − | + | + | + | + |
|  |  | CBH 9 | − | ND | − | + | + | + | + |
| 7 | CONF | CBH 4B | − | ND | − | + | + | − | − |
|  |  | CBH 4D | − | ND | − |  |  | − | − |
| 8 | LIN | CBH 17 | − | ND | − | + | + | − | − |

[1]CONF = recognizes a conformational epitope; LIN - = recognizes a linear epitope
[2]Summarizes results obtained in NOB assay and CD81-E2 binding assays described above
[3]Non-reciprocal partial competition is observed.
cBH-2 inhibits binding of CBH-5 to HCV 1a or 1b E2 protein at a level of ~50%.
CBH-5 inhibits binding of CBH-2 to HCV E2 of genotypes 1a, 1b, 2a, or 2b to ~80%.

Figure 19:
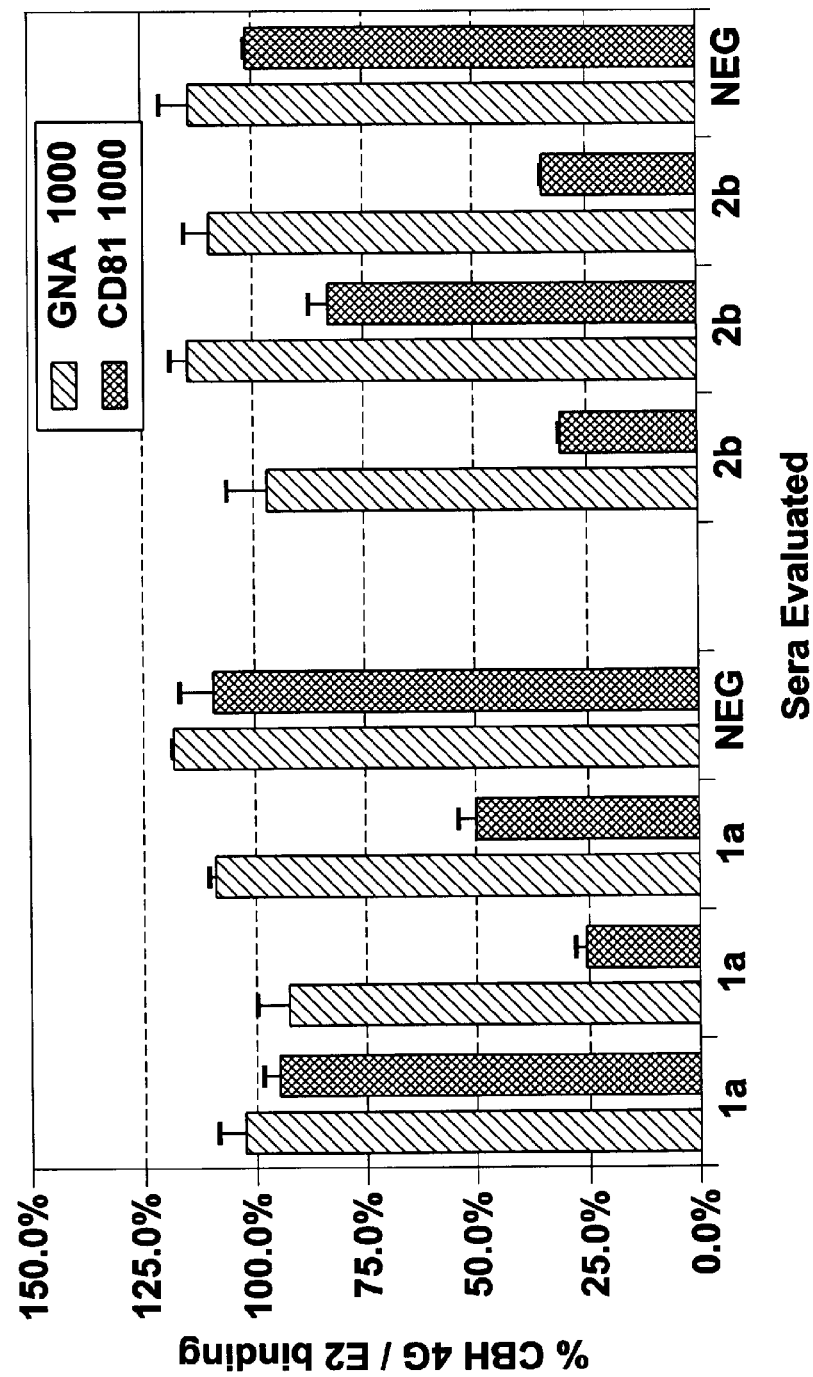
FIG. 19 is a bar graph that shows that HMAb CBH-4G can be employed to detect the presence of antibodies that inhibit binding of HCV E2 to CD81 in sera from HCV infected individuals. HCV 1a or 2b E2 protein derived from extracts of BSC-1 cells infected with vaccinia virus Q1a or Q2b was incubated with 4 µg/ml of a biotinylated preparation of HMAb CBH-4G for 20 minutes at 4° C. The four sera at left were tested with HCV 1a E2 protein; the four sera at right were tested with HCV 2b E2 protein. The E2-CBH-4G complexes were then added to wells coated with either 500 ng of GNA (blue bars) or 100 ng of GST-CD81-LEL (red bars) in the presence of a 1/500 dilution of the indicated sera from genotyped HCV infected (1a or 2b) or uninfected (NEG) individuals (x axis). After an overnight incubation at 4° C., the wells were washed, and bound biotinylated CBH-4G was detected as described in Example 7. The bars indicate the mean signal obtained from duplicate wells in the presence of the indicated serum (final dilution 1/1000) relative to the signal obtained in the absence of any competing serum. Error bars indicate one standard deviation from the mean.
Figure 20:
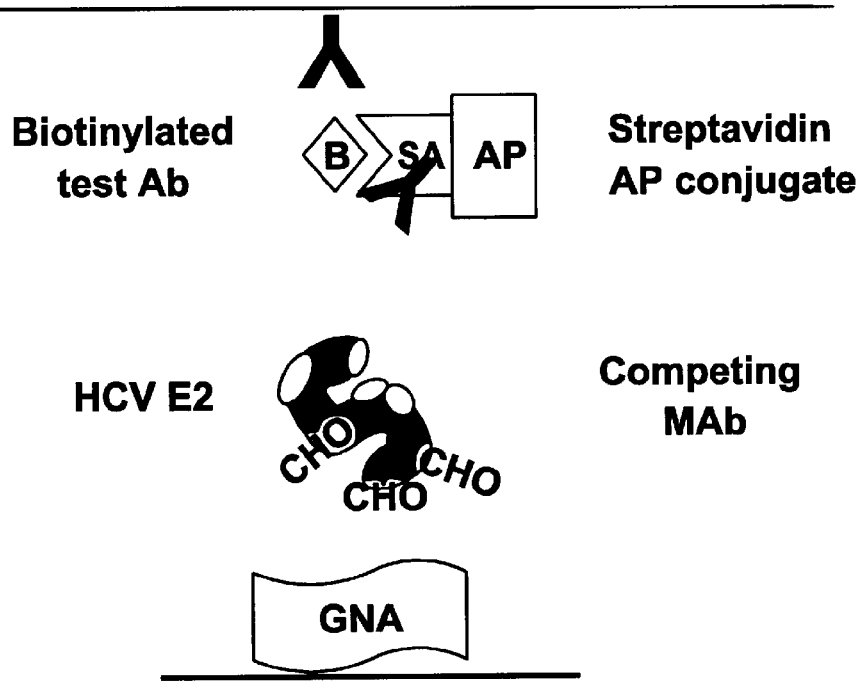
FIG. 20 is a cartoon of the competition assay. Plates are first coated with GNA lectin, which is used to capture full-length intracellular E2 onto microtiter plates by binding of CHO moieties to GNA lectin. Competing HMAb are contacted with the GNA-captured E2. Biotinylated test HMAb is added to the plates, and binding of the biotinylated test HMAb to E2 is detected using a streptavidin-AP conjugate. Inhibition of binding of test HMAb suggests epitopes within same antibody binding domain.

Accordingly this experiment was then repeated using HCV and control sera in place of the HCV HMAbs (FIG. 19). Six genotyped HCV sera (three genotype 1a sera and three genotype 2b sera) and two HCV negative sera were tested against the homologous E2 protein at a dilution of 1/1000. As seen with the HCV HMAbs little or no inhibition of HCV E2 binding to GNA was observed. Nor did either of the negative sera significantly affect binding of HCV E2 to CD81-LEL. In contrast a wide variation of inhibition of E2 binding to CD81-LEL was observed with the HCV sera. Thus HMAb CBH-4G binding to a putative receptor, CD81, in a microtiter plate format.

It is evident from the above results that the monoclonal antibodies are an important addition in the development of diagnostics and therapies for the treatment of patients having HCV. By virtue of recognizing genotypes 1 and type 2, HCV assays can be performed with a higher expectancy of fewer false negatives and fewer antibodies are required for performing the assays to identify HCV infection. The antibodies will find use in a wide variety of protocols. In addition, the antibodies may be used to identify genotypes, isolate virion particles, isolate HCV RNA, capture antigen from serum or other samples, and identify and isolate mimotopes (e.g., by screening random peptide phage libraries). By virtue of their being human, they may be used in therapy, either prophylactic, to protect a subject who may be exposed to the virus, or therapeutic, to reduce the effective viral load of a patient.

Example 8

Competition Analysis and Epitope Localization of Human Monoclonal Antibodies to HCV E2 that Inhibit HCV Replication in a Small Animal Model of HCV Infection Materials and Methods Cell lines and viruses. HeLa cells were grown in minimal essential media (MEM, Life Technologies, Bethesda, Md.) supplemented with 10% fetal calf serum (FCS) and 2 mM glutamine. Human embryonic kidney (HEK-293) cells were maintained in Dulbecco's modified minimal essential medium (DMEM, Life Technologies, Gaithersburg, Md.) supplemented with 10% fetal calf serum (GIBCO) and L-glutamine (2 mM) (GIBCO) in 5% $CO_2$. Recombinant vaccinia virus expressing HCV envelope proteins were constructed and grown as described (HCV JoV). Vaccinia virus 1488 expressing the structural proteins of HCV 1a strain H was obtained from Dr Charles Rice.

Monoclonal antibodies. The production, purification, and biotinylation of the HCV HMAbs were performed as described (HCV JoV). Rat monoclonal antibody 3/11 to HCV E2 was cultured as described previously and was obtained from Dr. Jane McKeating. Rat monoclonal antibody to the influenza hemaglutinin (HA) epitope was obtained from Roche Diagnostics (Indianapolis, Ind.). Murine monoclonal antibody to the c-myc epitope was obtained from Santa Cruz Biotechnology (Santa Cruz, Calif.).

Competition Assays. Monolayers of HeLa cells were grown to 80% confluence, infected with recombinant vaccinia virus expressing HCV E2, and cytoplasmic extracts prepared as described (HCV JoV). Microtiter plates were prepared by coating wells with 500 ng of purified *Galanthus nivalis* (GNA) lectin (SIGMA, St Louis, Mo.) in 100 µl of PBS for 1 hour at 37° C. Wells were washed with TBS (150 mM NaCl, 20 mM Tris-HCl, pH 7.5), and then blocked with 150 µl BLOTTO (TBS plus 0.1% Tween-20, 2.5% normal goat sera, 2.5% non fat dry milk) by incubation for 1 hour at room temperature. Plates were washed twice with TBS followed by the addition to each well of 15 µl of extract in 100 µl BLOTTO. After 1.5 hours at RT, plates were washed 3 times with TBS followed by the addition of competing antibodies at various concentrations in a total volume of 50 µl/well. Plates were incubated for 30 minutes at which point 50 µl/well of a 8 µg/ml (CBH-4G) or 4 µg/ml solution (all other HMAbs) of biotinylated test antibody was added. After incubation for 1.5 hours at room temperature, the plates were washed 3 times with TBS, and 100 µl of 1/1000 diluted alkaline-phosphatase conjugated streptavidin (Amersham-Pharmacia Biotech, Piscataway, N.J.) was added. After 1 hour at room temperature, the plates were washed 4 times with TBS followed by 30 minutes incubation with a 1 mg/ml solution of p-nitrophenyl phosphate (PNPP). Absorbance was measured at 405 nm with a multi-well plate reader (BioTek Instruments, Winooski Vt.). Signals obtained with biotinylated test antibody and E2 in the presence of competing antibody were compared to signals obtained from test antibody and E2 in the absence of any competing antibody.

Isolation and cloning of HCV E2 deletion constructs. HCV 1b RNA was isolated from serum from an individual infected with HCV genotype 1b using the PureScript (Gentra systems, Minneapolis, Minn.) according to the manufacturer's instruction. Both the vaccinia virus recombinant Q1b and all of the HCV 1b deletion constructs were derived from the same individual. HCV RNA was converted into cDNA using random primers and reverse transcriptase (Perkin-Elmer Applied Biosystems, Foster City, Calif.) according to manufacture's protocol at 42° C. for 30 min. Fragments of HCV E1 were amplified by polymerase chain reaction (PCR) using pfu taq polymerase (Stratagene, La Jolla, Calif.) from cDNA with appropriate oligonucleotide primers (obtained from Integrated DNA Technologies, Corlville, Iowa) that contained flanking Bgl II or Pst I restriction sites. HCV strain H constructs were amplified by PCR from viral stocks of vaccinia virus construct vv1488. Amplified DNAs were subsequently ligated into the Bgl II and Pst I digested pDisplay plasmid (Invitrogen, Carlsbad, Calif.). All plasmids were constructed using standard procedures (28). The presence of in-frame HCV inserts was confirmed by DNA sequencing using ABI PRISM Dye terminator cycle sequencing on an automated sequencer (PE-Applied Biosystems, Foster City Calif.).

Expression of HCV E2 deletion constructs. Human embryonic kidney (HEK) 293 cells were seeded to obtain 60-70% confluence by the following day. For transfection of a T-75 flask, a mixture of μg of the appropriate plasmid DNA and μg of PerFect Lipid Pfx-2 (InVitrogen, Carlsbad Calif.) were combined in ml of serum free media at a DNA:lipid ratio of 1:6 (w/w). After four hours incubation at 37° C. the transfection solution is replaced with 2.5 ml of complete medium and cells were grown for an additional 24 hours. Cell extracts were prepared by washing cells with PBS and resuspending them in 1 ml of lysis buffer (150 mM NaCl, 20 mM Tris pH 7.5, 0.5% deoxycholate, 1.0% Nonidet-P40, 1 mM EDTA, 0.5 mg/ml Pefabloc (Boehringer Mannheim, Indianapolis, Ind.), 2 μg/ml Aprotinin, 2 μg/ml Leupeptin, and 1 μg/ml Pepstatin). Nuclei were pelleted by centrifugation at 18,000×g at 4° C. for 10 minutes. For Western blot analysis, extracts were combined 1 to 1 with 2× sodium dodecyl sulfate polyacrylamide electrophoresis sample buffer (SDS-SB; 20% glycerol, 10% β-mercaptoethanol, 4.8% SDS, 0.125 mM Tris pH 6.8). Proteins were denatured via heating to 95° C. for five minutes followed by sodium dodecyl sulfate polyacrylamide electrophoresis (SDS-PAGE) in 12% polyacrylamide gels of 20 μl aliquots of the denatured extracts. SDS-PAGE and subsequent Western blotting were performed using standard methods.

For microtiter plate assays, microtiter plates were prepared by coating wells with 500 ng of purified *Galanthus nivalis* (GNA) lectin (SIGMA, St Louis, Mo.) in 100 μl of PBS for 1 hour at 37° C. Wells were washed with TBS (150 mM NaCl, 20 mM Tris-HCL, pH 7.5), and then blocked with 150 μl BLOTTO (TBS plus 0.1% Tween-20, 2.5% normal goat sera, 2.5% non fat dry milk) by incubation for 1 hour at room temperature. Wells were washed twice with TBS followed by the addition of 25 μl of extract from HEK-293 cells transfected with E2 deletion constructs diluted in 75 μl of BLOTTO. After 1.5 hours at room temperature, plates were washed 3 times with TBS followed by the addition of monoclonal antibodies at various concentrations. Plates were incubated for 1.5 hours, washed 3 times with TBS, and then 100 μl of appropriate alkaline-phosphatase conjugated secondary antibody, diluted in BLOTTO as recommended by the manufacturer, was added (for anti-human and anti-mouse, Promega, Madison, Wis., for anti-rat, Kirkegard and Perry, South San Francisco Calif.). After 1 hour at room temperature, the plates were washed 4 times with TBS followed by incubation for 30 minutes with a 1 mg/ml solution of p-nitrophenyl phosphate (PNPP). Absorbance was measured at 405 nm with a multi-well plate reader (Du Pont Co, Wilmington, Del.).

Flow cytometric analysis. Various dilutions of test antibody in a total volume of 100 μl of staining solution (PBS plus 1% FCS and 0.1% sodium azide) were combined with $10^6$ viable HCV E1 expressing or control HEK-293 cells, resuspended in 100 μl of staining solution, and incubated at 4° C. for 45 minutes. After adding an additional 3 ml of staining solution, the cells were pelleted by centrifugation for 10 minutes at 500×g at room temperature. The pellet was reserved and resuspended in 100 μl of FITC conjugated secondary antibody diluted as recommended by the manufacturer (Jackson Immunoresearch laboratories, West Grove, Pa.) in staining solution. After 45 minutes at 4° C., 900 μl of staining solution was added, and the cells were pelleted as above. The cells were then resuspended in 1 ml of fixative solution (3.8% formaldehyde in PBS), and the amount of HMAb bound to the surface of cells was analyzed on a FACScalibur (Becton-Dickinson, San Jose, Calif.). For two color staining secondary antibodies were conjugated to R-phycoerythrin and fluorescence monitored at 606 nm while EGFP fluorescence was monitored at 545 nm.

Results

Human monoclonal antibodies recognizing HCV E2 were obtained from two sources. Ten HMAbs (CBH-2, CBH-4B, CBH-4D, CBH-4G, CBH-5, CBH-7, CBH-8C, CBH-8E, CBH-11, and CBH-17) were obtained from an individual who had an asymptomatic infection with HCV of genotype 1b. The antibodies varied in the breadth of their reactivity with different genotypes of HCV E2 and in their ability to inhibit the interaction of HCV E2 with human CD81. The designations, reactivity, and properties of the HCV HMAbs are summarized in Table 6.

TABLE 6

HCV HMAbs

| HCV E2 Antibodies | | | E2 Reactivity[3] | | Functional Assays | | |
|---|---|---|---|---|---|---|---|
| | | | | | Inhibit | Bind | |
| HMAb[1] | Heavy[2] | Light | Gtyp 1 | Gtyp 2 | CD81[4] | Virions[5] | Trimera[6] |
| CBH-2 | VH5-51 | VκIII A27 | 7 (8) | 2 (2) | ++ | ++ | ++ |
| CBH-8E | VH1-69 | VκI O12 | 8 (8) | 2 (2) | ++ | ND | ND |
| CBH-5 | VH1-69 | VκI L12 | 8 (8) | 2 (2) | ++ | + | +/− |
| CHB-8C | VH4-59 | VκIII L6 | 5 (8) | 2 (2) | ++ | ND | ND |
| CBH-11 | VH1-69 | VκI L12 | 4 (8) | 2 (2) | ++ | − | ND |
| CBH-7 | VH1-69 | VκI O12 | 8 (8) | 2 (2) | ++ | − | ++ |
| CBH-4G | VH1-9 | VκI A20 | 8 (8) | 2 (2) | − | ND | ND |
| CBH-4B | VH1-9 | VκIII A27 | 8 (8) | 0 (2) | − | ND | ND |
| CBH-4D | VH1-9 | Vλ 2a2 | 8 (8) | 0 (2) | − | ND | ND |
| CBH-17 | VH3-73 | Vλ 3h | 7 (8) | 0 (2) | − | ND | ND |
| 3/11 | rat MAb | | 8 (8) | 2 (2) | ND | ND | ND |
| HA | rat MAb | | 2 (2) | 0 (0) | − | ND | ND |
| R04 | IgG1 | | 0 (8) | 0 (2) | − | − | ND |

[1]CBH Antibodies are further described in Hadlock et al. J. Virol. 74: 10407-10416, 2000; incorporated herein by reference. HA recognizes a synthetic epitope present in some HCV E2 constructs. rMAb 3/11 was generously provided by Jane McKeating, Ph.D.
[2]Antibody sequences are from Chan HC, et al. In Press Blood.
[3]The number of reactive E2s is followed by the total number tested (in parentheses).
[4]++ = inhibits binding of E2 to CD 81. − = no inhibition. ND = not done.
[5]++ = binds to HCV virions in immunoprecipitation and or CD 81 inhibition assays.
[6]++ = significantly inhibits serum HCV levels in Trimera mice. Test HMAb is pre-incubated with HCV inoculum prior to exposure to human liver and transplantation into Trimera mice. HCV serum viral loads are determined at 15-20 days post transplantation.

Sequence analysis of the IgG1 genes of 10 of the 11 HMAbs confirmed that they were derived from independent B cells. Of note, HMAb CBH-4B, CBH-4G, CBH-4D, and CBH-17 all failed to inhibit the binding of E2 to CD81-LEL (Table 6).

Figure 21A:
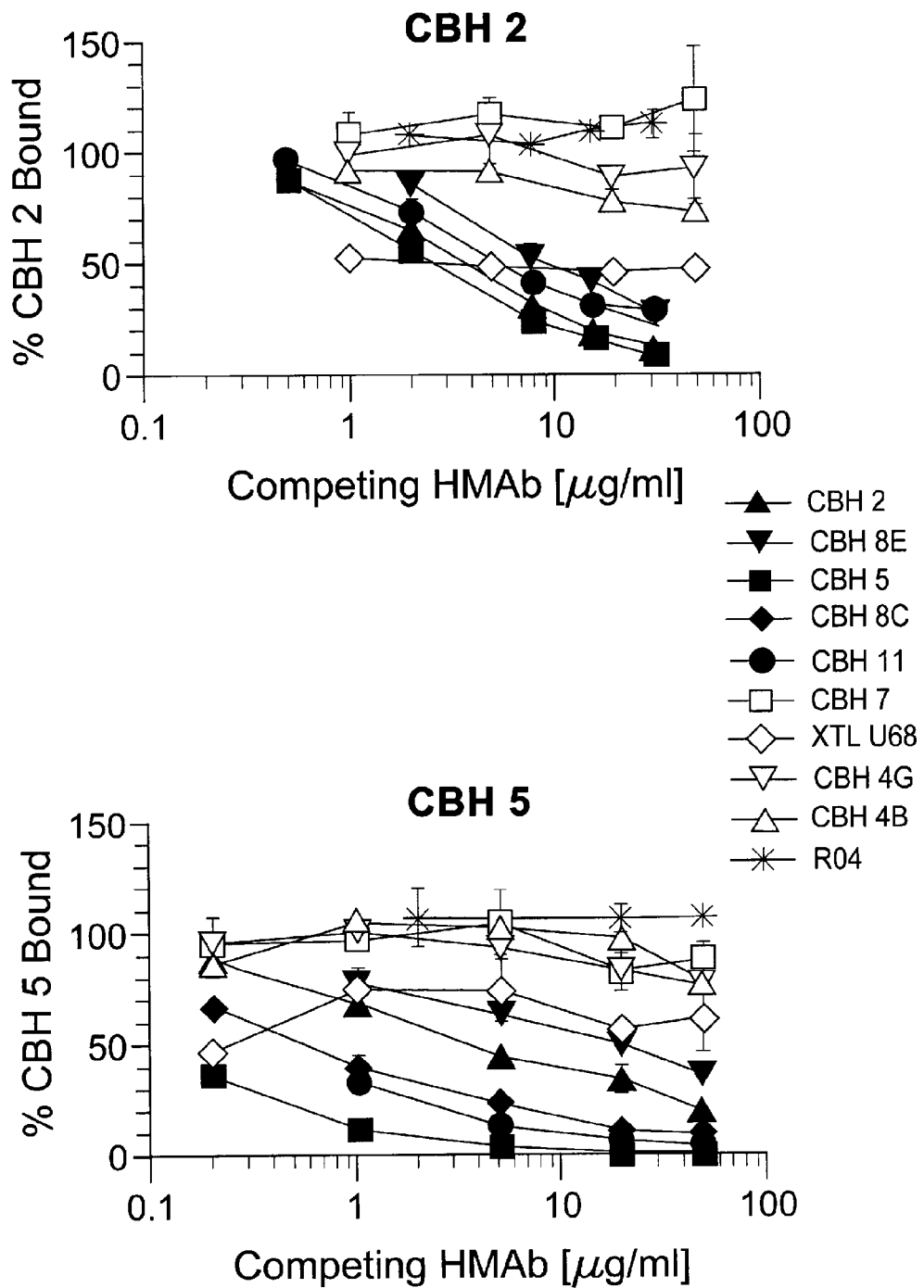
FIG. 21 shows competition analysis of four HCV human monoclonal antibodies. HCV Q1b E2 protein was captured onto GNA lectin coated microtiter plates. Biotinylated test antibody (indicated above each panel) at 2 µg/ml was added to wells containing the indicated concentration (x-axis) of competing human monoclonal antibody. Bound biotinylated test antibody was detected using streptavidin alkaline phosphatase conjugate. Signal obtained in the presence of competing antibody was expressed as the percent of signal obtained by the biotinylated test antibody relative to the signal obtained in the absence of competing antibody (y-axis). The points indicate the mean value obtained from two replicate wells. The bars indicate one standard deviation from the mean. Competing antibodies are identified in the key at left.
Figure 21B:
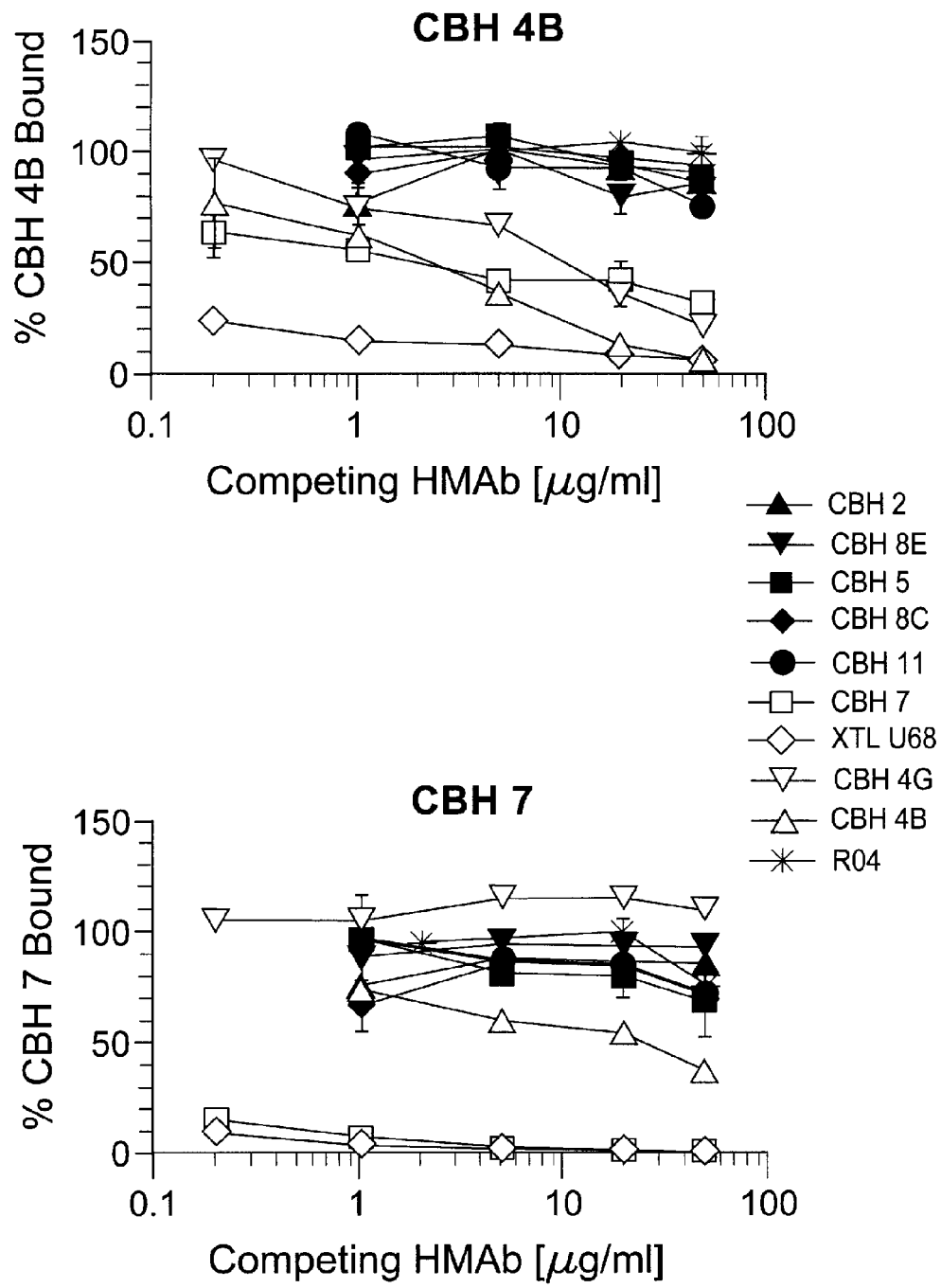
Figure 24:
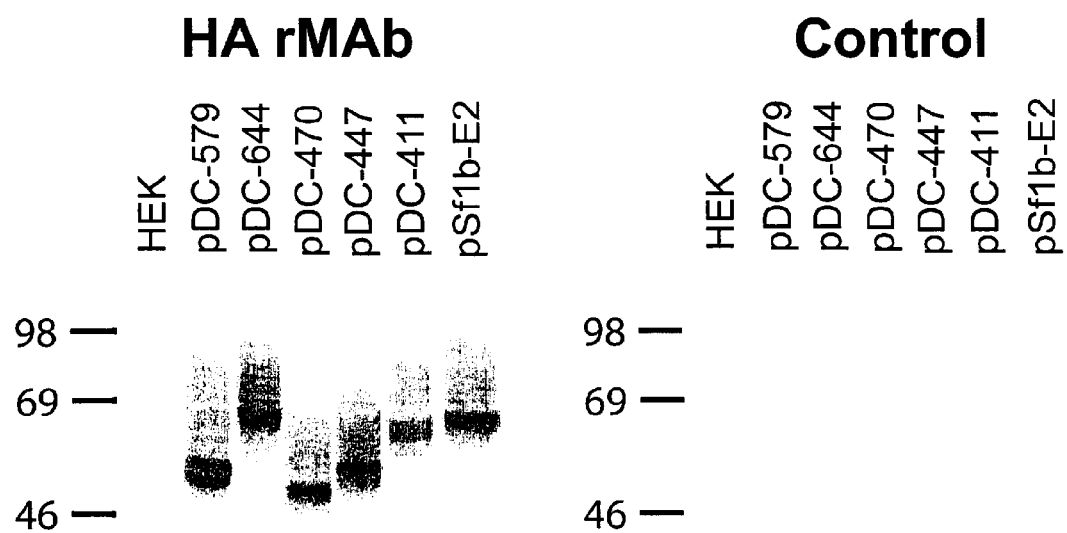
FIG. 24 shows Western blot analysis of HCV E2 deletion constructs indicating that the constructs are efficiently expressed. The indicated HCV E2 constructs (above lanes) were transfected into HEK-293 cells. Twenty-four hours after transfection cytoplasmic extracts were prepared and fractionated via SDS-PAGE. The fractionated proteins were transferred to nitrocellulose membranes and incubated with either rat monoclonal antibody to the HA epitope (HA rMAb) or a control HMAb to a CMV protein (control). Bound antibody was detected with the appropriate AP conjugated antisera. HEK=mock-transfected HEK-293 cells. The migration of molecular weight markers is indicated at left.
Figure 27:
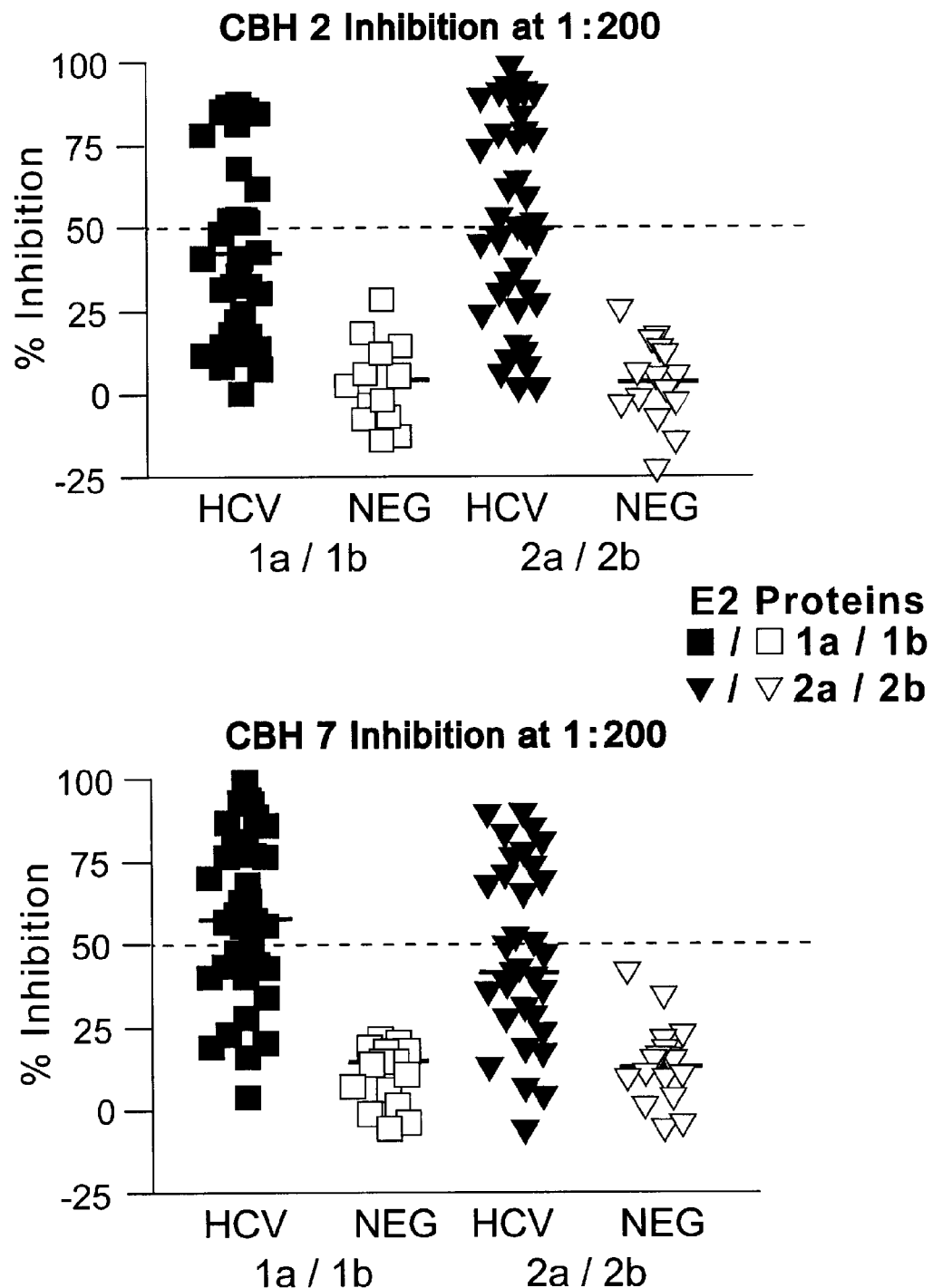
FIG. 27 shows scatterograms demonstrating that sera from HCV infected individuals have variable levels of antibodies that inhibit CBH-2 and CBH-7. Scattergram showing percentages of test HMAb inhibition. HCV sera of the indicated genotype (x-axis) or control sera (NEG) were diluted 1:200 and incubated with biotinylated test HMAb (indicated above graph) in wells coated with genotyped matched E2 proteins. Binding of test HMAb was detected using streptavidin-conjugated-AP. Results obtained were compared to binding of test HMAb in absence of competitor. Each symbol indicates results obtained with an individual serum. The line indicates the median percent inhibition. The dotted line indicates the cutoff for calling a serum positive for the presence of the test HMAb.
Figure 28:
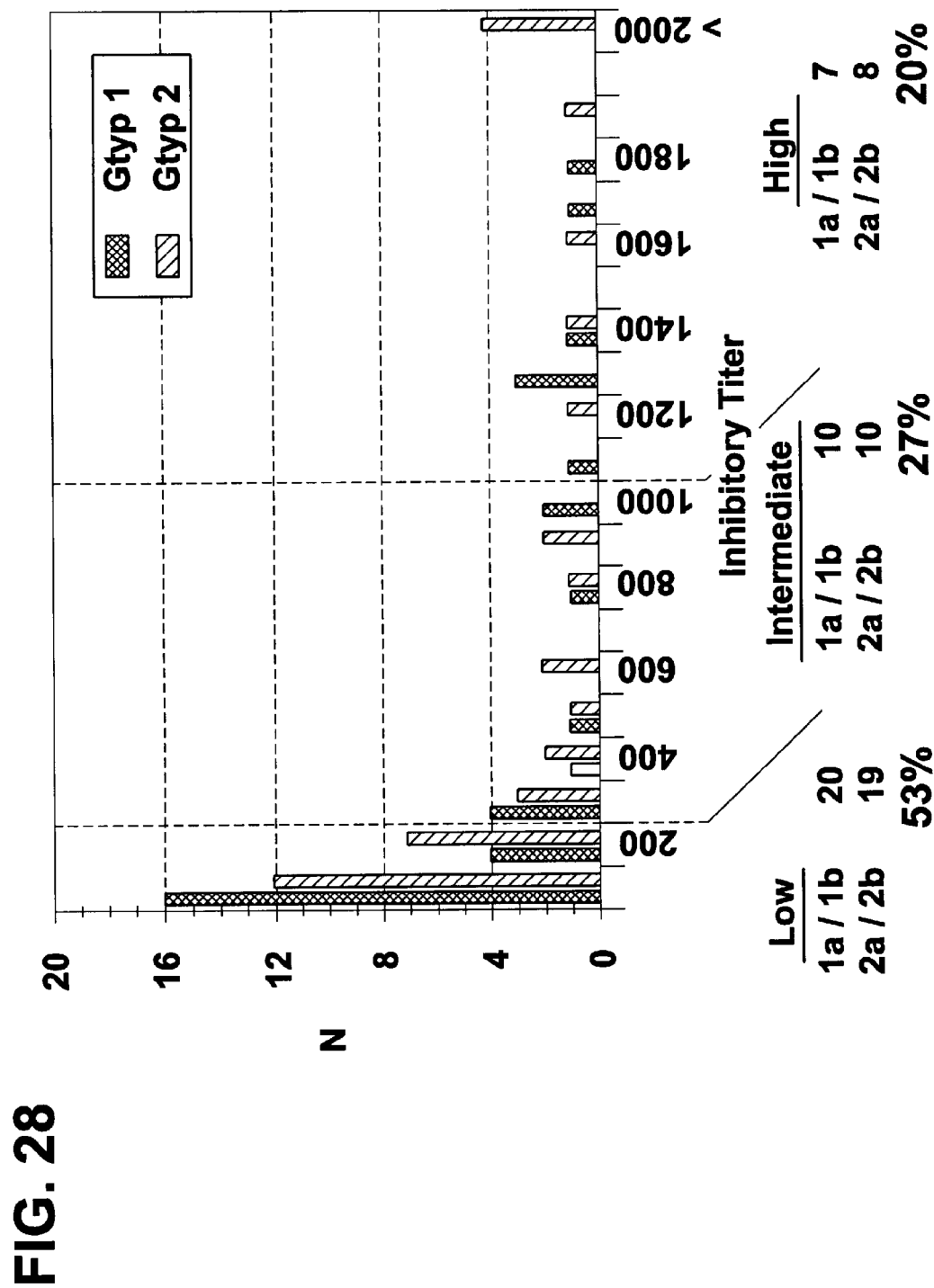
FIG. 28 is a histogram of CBH-2 inhibitory titers obtained from a panel of 74 individuals with chronic hepatitis. The CBH-2 inhibitory titers obtained with individual serum were segregated into 20 bins of 100 and 1 bind for all titers >2000. The bars indicate the number of sera having a CBH-2 inhibitory titer within a given bin. Numbers of HCV 1a/1b sera are indicated in black. Number of HCV 2a/2b sera is indicated in gray. The number of sera with low (<200), intermediate (200-1000), and high (>1000) inhibitory titers is indicated below the graph.
Figure 29:
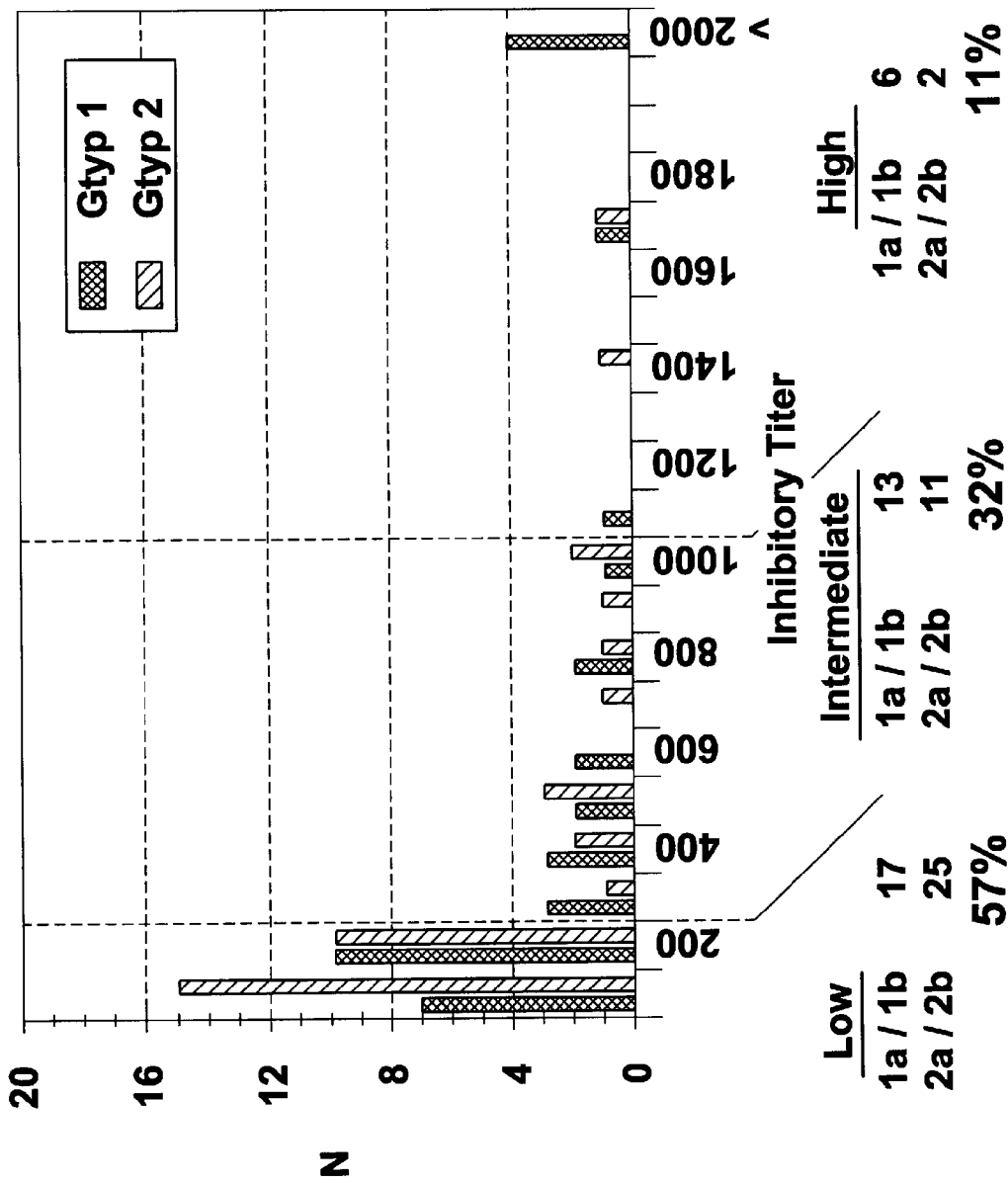
FIG. 29 is a histogram of CBH-7 inhibitory titers obtained from a panel of 74 individuals with chronic hepatitis. The CBH-7 inhibitory titers obtained with individual serum were segregated into 20 bins of 100 and 1 bin for all titers >2000. The bars indicate the number of sera having a CBH-7 inhibitory titer within a given bin. Numbers of HCV 1a/1b sera are indicated in black. Number of HCV 2a/2b sera is indicated in gray. The number of sera with low (<200), intermediate (200-1000), and high (>1000) inhibitory titers is indicated below the graph.

Competition assays were employed to determine the number of distinct sites within E2 that were reactive with the HMAbs. Individual HMAbs were purified, biotinylated, and the binding of the antibodies in the presence of increasing concentrations of competing antibody was determined. Representative binding curves are presented in FIG. 21. Binding of HMAbs CBH-2, CBH-5, CBH-8C, and CBH-11 to HCV 1b E2 were all significantly inhibited by an excess of HMAbs CBH-2, -8E, -5, -8C, and -11. In general HMAb CBH-5 exhibited the highest level of inhibition, and CBH-2 and CBH-8E exhibited the weakest inhibition. For HMAbs CBH-2, -5, -8C, and -11 and no significant inhibition was observed with a control HMAb, R04, or HCV HMAbs CBH-7, CBH-4B, and CBH-4G. In contrast, HMAb CBH-7 was strongly inhibited by itself, very weakly inhibited by HMAb CBH-4B, and unaffected by the presence of HMAbs CBH-2, -5, -8E, -11, -4G, or the control antibody. Similarly HMAb CBH-4B showed intermediate levels of inhibition with HMAbs CBH-7, CBH-4B, and CBH-4G. HMAbs CBH-2, -5, -8C, -11, and 8E recognized epitopes that were in close proximity to each other and potential define an antibody-binding site within HCV E2

The results from the full series of inhibition experiments are presented in FIG. 22. Five antibodies CBH-2, -8E, -5, -8C, and -11 that recognize conformational epitopes and can inhibit the binding of E2 with CD81-LEL all significantly cross competed and formed one competition group (Group I). A second competition group (Group II) contains HMAb CBH-7. A third competition group is formed by HMAbs CBH-4G, CBH-4B, and CBH-4D, and a fourth competition group is formed by CBH-17, the only antibody in the panel to recognize a linear epitope. The binding of antibodies from group I was only marginally affected by antibodies from group II and not affected at all by antibodies from groups III or IV. The binding of antibodies from group II to E2 was not affected by the presence of antibodies from any other group. Antibodies from group III were unaffected by the presence of antibodies from group I and either strongly inhibited, or in the case of CBH-4G binding in the presence of CBH-7, stimulated by the presence of antibodies from group III. HMAb CBH-17 did not influence the binding of any of the other antibodies. Thus the eleven HCV HMAbs defined four relatively distinct antibody binding sites within HCV E2.

Currently there is no efficient culture system for the propagation of HCV. When HCV structural proteins are expressed in mammalian derived cells the proteins are usually retained intracellularly. Recently, however several groups have reported the successful expression of HCV E2 on the surface of mammalian cells. Since HCV E2 expressed on the surface of cells might more closely mirror the structure of HCV E2 on the surface of infectious virions, we expressed the extracellular domain of HCV 1b E2 (amino acids 384-661) in a the pDisplay vector. The HCV E2 sequences were expressed in-frame with the transmembrane domain of platelet derived growth factor receptor (PDGFR). The signal sequence at the carboxy terminal of the HCV E1 protein was replaced with the murine IgK leader sequence. Strong linear epitopes from influenza virus hemaglutinin (HA) and c-myc are located immediately in front and behind the HCV sequences, respectively. The expected molecular weight of the HCV 1b construct sf1b (expressing amino acids 384-661 of HCV 1b E2) was 42 KD, prior to glycosylation. Two different immunoreactive proteins were produced by the sf1b-E2 cell line when protein expression was analyzed by Western blot. The first is a relatively discreet band migrating at 68-70 kdal. This species was efficiently purified by affinity chromatography with GNA lectin and is an intracellular form of E2 with mannose-rich carbohydrate chains. The second immunoreactive protein is a heterogeneous smear, which ranged in size from 70 to 98 kD. This species was not efficiently purified by GNA lectin chromatography and is assumed to have complex carbohydrate chains and be the major species present on the surface of the cells. DNA sequencing confirmed cloning of the expected insert with no frame shifts or terminations.

The HCV E2 construct sf1b-E2 was introduced into CHO cells and a cell line expressing the protein was obtained. The sf1b-E2 expressing cells were then combined with the HCV HMAbs or control antibodies, and the ability of the HMAbs to bind to cell-surface expressed HCV E2 was determined. When stained with the monoclonal antibody to the HA epitope, a strong signal was obtained from greater than 95% of the cells. No specific signal was obtained from the parent CHO cells nor was any signal obtained with the sf1b-E2 expressing cell line and control antibody. The HCV HMAbs CBH-2, CBH-7, and CBH-4B all exhibited staining of the sf1b-E2 cell line that was equivalent to that observed with the HA epitope. In contrast the HMAbs CBH-11 and CBH-17, although also reactive with the cell surface expressed E2 protein, exhibited 10 fold reduced staining relative to the other HMAbs (Table 7). Thus 9 of the 11 HCV HMAbs reacted strongly with cell-surface expressed E2 protein, and two of the HMAbs exhibited significant reductions in reactivity when E2 was expressed on the cell surface.

not shown). DNA sequencing confirmed that each of the constructs expressed the expected sequences with no frame shifts or terminations.

Therefore, the HCV E2 deletion constructs were transfected into HEK-293 cells, cytoplasmic extracts prepared, and intracellular forms of E2 captured onto microtiter plates using GNA lectin. The reactivity of the HCV HMAbs with the GNA captured E2 was then determined. As expected, all of the HCV HMAbs reacted with sf1b E2 protein and none reacted with proteins captured from extracts of mock-transfected HEK-293 cells (FIG. 25). Also all of the HCV HMAbs were strongly reactive with E2 produced by pDN-411, indicating that the epitopes recognized by the HMAbs did not include HVR-1. Next, the same panel of antibodies was tested against the extracellular domain of HCV E2 derived from strain H both with (sfH1a-E2) (SEQ ID NO: 29) or without (pDNH-411) HVR1 (SEQ ID NO: 30). HCV HMAbs CBH-8C and CBH-11 did not recognize either sfH1a-E2 or pDNH-411, suggesting that the epitopes recognized by these two HMAbs were mutated in strain H derived E2 protein. Significant reductions in the reactivity of HMAbs CBH-2, CBH-8E,

TABLE 7

Reactivity of HCV HMAbs with intra & extracellular E2 proteins

| HMAb | Sf-1b | | pDN-411 | | PDN-447 | | PDN-470 | | PDC-644 | | PDC-579 | |
|---|---|---|---|---|---|---|---|---|---|---|---|---|
| | GNA[1] | Flow[2] | GNA | Flow[3] | GNA | Flow | GNA | Flow | GNA | Flow | GNA | Flow |
| CBH 2 | ++ | 338 | + | | − | | − | | + | | − | |
| CBH 8E | ++ | 408 | + | | − | | − | | + | | − | |
| CBH 5 | ++ | 546 | ++ | 17 | − | 2 | − | 2 | ++ | 28 | − | 2 |
| CBH 8C | ++ | 282 | ++ | | − | | − | | ++ | | − | |
| CBH 11 | ++ | 43 | ++ | | − | | − | | ++ | | − | |
| CBH 7 | ++ | 303 | ++ | 19 | ++ | 26 | ++ | 14 | ++ | 27 | − | 2 |
| CBH 4G | ++ | 175 | ++ | | ++ | | ++ | | ++ | | − | |
| CBH 4B | ++ | 241 | ++ | 17 | ++ | 21 | ++ | 9 | ++ | 18 | − | 2 |
| CBH 4D | ++ | 173 | ++ | | ++ | | + | | ++ | | − | |
| CBH 17 | ++ | 23 | + | | ++ | | ++ | | − | | − | |
| HA | ++ | 375 | ++ | 42 | ++ | 36 | ++ | 19 | ++ | 75 | ++ | 40 |
| c-myc | ++ | 68 | ++ | | ++ | | ++ | | ++ | | ++ | |
| R04 | − | 3 | − | 2 | − | 2 | − | 2 | − | 2 | − | 2 |

[1]Results in GNA capture assays are expressed as ++ strongly positive (OD > 0.5), + positive (~OD 0.1 to 0.5), − negative.

[2]Mean Fluorescence obtained with 10 ug/ml of indicated HMAb staining CHO cells permanently expressing the sflb-E2 construct.

[3]Mean Fluorescence obtained with 10 ug/ml of indicated HMAb staining HEK-293 cells transiently transfected with the indicated HCV E2 constructs. A blank cell indicates the HMAb was not tested by flow cytometry.

Next we were interested in localizing the regions of HCV E2 that contained the binding sites recognized by antibodies from the four different groups. To that end deletions were made from the amino terminal and carboxy terminal ends of sf1b-E2. One of the deletions pDN411 removed the hypervariable region of HCV sf1b-E2. The other deletions removed larger portions from the amino or carboxy terminals of sf1b-E2. The deleted E2s were then re-cloned into the vector pDisplay, which allows for the cell surface expression of inserts. HCV E2 deletion constructs expressing sequences from genotype 1b and the H isolate of HCV 1a were constructed (SEQ ID NO: 28-35) (FIG. 23). The expression of the E2 deletion constructs was verified by transfection into HEK-293 cells followed by Western blot analysis of cytoplasmic extracts using a monoclonal antibody to the HA epitope (FIG. 24). No reactivity was observed with a control antibody to a CMV protein (data not shown). As seen with sf1b-E2, both a faster migrating discreet band and a slower migrating heterogenous smear were observed with all constructs. Similar results were obtained with sfH1a-E2 and pDNH-411 (data and CBH-5 with strain H E2 protein were also noted. These HMAbs retained reactivity with the HVR1 construct pDNH-411, confirming that the epitope recognized by these HMAbs was outside of HVR1. The other HCV HMAbs and control antibodies exhibited equivalent reactivity with the strain H derived E2 proteins and the genotype 1b E2 proteins. Thus nine of the 11 HCV HMAbs recognized an epitope conserved between sf1b-E2 and sfH1a-E2.

Further deletion of amino acids 384-446 (pDN-447) (SEQ ID NO: 31) or 384-469 (pDN-470) (SEQ ID NO: 32) from the sequences of sf1b-E2 abrogated the reactivity of all Group I HMAbs (CBH-2, -8E, -5, -8C, and -11). Also rat MAb 3/11 which was previously determined to recognize a linear epitope consisting of amino acids 384 to 445 of HCV E2 was non-reactive with pDN-447 and pDN-470. In contrast, HCV HMAbs of group II, III, and IV retained their reactivity with both constructs. PDN-447 and pDN-470, indicating that the epitopes recognized by HMAbs from these groups were located in the central to carboxy terminal regions of HCV E2. Finally, E2 proteins with deletions in the carboxy terminal region were evaluated with the HCV HMAbs. All of the HCV HMAbs, except for CBH-17, were reactive with E2 proteins expressing amino acids 384-644 of HCV E2 (pDC-644) (SEQ ID NO: 33). In contrast, none of the HCV HMAbs were reactive with constructs expressing amino acids 384-579 of HCV E2 (pDC-579) (SEQ ID NO: 34). The rat MAb 3/11 retained reactivity with both carboxy terminal deleted E2 proteins as did MAbs to the HA or c-myc epitopes. Thus deletion of HCV E2 sequences between amino acids 644 to 579 is sufficient to abrogate reactivity of all 10 HCV HMAbs that recognize conformational epitopes.

Use of the GNA assay confirmed reactivity of the HCV HMAbs with the intracellular forms of the deletions. To verify the reactivity of the HCV HMAbs with the cell surface expressed E2 of the same deletion constructs the binding of the HMAbs with cells expressing the E2 deletion constructs was evaluated by flow cytometry. Constructs were evaluated with CBH-5 from HMAb group I, CBH-7 of HMAb Group III, and HMAb CBH-4B of HMAb group III. Control antibodies included rat MAb 3/11 and HA. Representative results with E2 deletion constructs pDN411 and pDN447 are presented in FIG. 25. Results with all of the E2 deletions are included in Table 7. Because the E2 deletions were introduced into the HEK-293 cells via transient transfection only about 50-60% of the cells took up plasmid and expressed E2 proteins. Thus the geometric means of the fluorescence observed are notably reduced relative to those obtained with the cloned CHO cell line. Nevertheless, results obtained with HMAbs CBH-5, CBH-7, and CBH-4B by flow cytometry were in complete concordance with the results of the GNA capture assay (Table 7). Thus HMAbs from groups II and III recognize epitopes located between amino acids 470 to 644 of HCV E2. HMAbs from group I recognize an epitope located between amino acids 411-644 of HCV E2.

Example 9

High Levels of Antibodies that can Neutralize HCV Infection are Rare in HCV Infected Individuals Patients and Methods Patients. Sera evaluated were from individuals undergoing nucleic acid testing to confirm or follow up a diagnosis of hepatitis C infection between 1991 and 1999. All individuals were being seen for their hepatitis at clinics in the San Francisco bay area. The subjects were positive for HCV RNA by polymerase chain reaction, negative for the presence of hepatitis B virus surface antigen, genotyped, and not receiving antiviral therapy at the time the sample was obtained. Demographic information was obtained from medical records and included age, sex, date of diagnosis, previous interferon therapy, alanine transaminase (ALT) value, and potential route of exposure. The majority of the subjects reported at least one risk-factor for HCV infection. Not all information was available from all subjects. Liver biopsies, when performed, were scored using the histologic activity index (HAI). Genotype analysis was performed using the InnoLIPA assay according to manufacturer's instructions (Innogenetics, Leuven, Belgium). HCV viral load determinations were performed with the COBAS Amplicor HCV monitor kit (Roche molecular systems, Alameda, Calif.). HCV negative control sera were obtained from plasma of blood donors to the Stanford Medical School blood center, and were negative for the presence of transfusion-transmitted viruses by standard antibody-based screening assays.

E2 Antibody Screening of HCV sera. Monolayers of HeLa cells were grown to 80% confluence and infected with HCV E2 expressing vaccinia virus. Twenty-four hours after infection cells were harvested and extracts were prepared as described (Hadlock et al., 2000). ELISA assay for HCV E2 reactivity were performed as outlined below. Microtiter plate wells were coated with 500 ng of purified *Galanthus nivalis*, lectin in 100 ml of PBS for 1 hour at 37° C. Wells were then washed with TBS and blocked by incubation with BLOTTO (TBS plus 0.1% Tween-20, 2.5% normal goat sera, 2.5% non fat dry milk). Plates were washed and each well received 15 ml HCV E2 containing extract diluted in BLOTTO. After incubation for 1.5 hours at 25° C., wells were washed with TBS followed by addition of increasing dilutions of sera from HCV infected or uninfected individuals diluted in BLOTTO. After incubation for 30 minutes biotinylated test HMAb was added to a final concentration of 2 mg/ml. The plates were incubated for 1.5 hours at 25° C., wells were washed three times with TBS and 100 ml of streptavidin-AP conjugate added for 1 hour at 25° C. Wells were washed 4 times with TBS followed by incubation with PNPP. Substrate development was allowed to proceed for 30 minutes, then the absorbence of the wells at 405 nm was determined using a multiwell plate reader.

For each dilution of competing serum the optical density (OD) reading obtained was compared to the OD obtained from wells without competing antibody. The resulting percentages of bound antibody were plotted versus the dilution and employed to calculate the dilution of sera that resulted in 50% inhibition of test HMAb binding. Sera that did not achieve 50% inhibition were assigned a titer of 40, which was less than the lowest dilution tested. Individuals evaluating sample seroreactivity were blinded to the viral load and clinical status of the samples they were testing. Statistical analysis was performed using InStat and Prism software packages (Graph Pad Software Inc, San Diego, Calif.).

Results

In this study, sera from HCV-infected individuals were evaluated for the presence of antibodies capable of inhibiting the binding of CBH-2 and CBH-7 to HCV E2. Human monoclonal antibodies CBH-2 and CBH-7 were purified and biotinylated, and the dilution of serum that resulted in 50% inhibition of CBH-2 or CBH-7 binding to a genotype-matched E2 protein was determined. Sera from HCV-negative individuals were used to measure nonspecific binding and to establish a cutoff value. Sera from HCV-infected individuals were considered positive for the presence of competing antibody if 50% or greater inhibition of E2 binding was obtained at a dilution of 1/200 or greater (FIGS. 26 and 27). Among 74 sera from HCV-infected individuals positive for viral RNA, 35 (47%) were positive for antibodies inhibiting CBH-2 binding, and 32 (43%) were positive for antibodies inhibiting CBH-7 binding (FIGS. 28 and 29). Fifteen sera (20%) were negative for the presence of antibodies that inhibited both CBH-2 and CBH-7. Nineteen (27%) individuals has high titers (>1/1000) of antibodies that inhibited binding of CBH-2 or CBH-7 (see Table 8). These individuals had a significantly reduced median viral load ($2.4\times10^6$ vs. $4.7\times10^6$, p=0.035), but were not otherwise different than other HCV infected individuals. Thus, most HCV infected individuals are characterized by low levels of serum antibodies with putative neutralization activity. Individuals with low levels of CBH-2 or CBH-7 like HMAbs can be identified using a simple inhibition assay. Therapeutic use of HCV-neutralizing human monoclonal antibodies, such as CBH-2 and CBH-7, has the potential to be of value in these individuals.

TABLE 8

Distribution of CBH-7 inhibitory titers in HCV Sera

| Characteristic | N/Value | CBH 2/CBH 7 Inhibitory Titer <1000 | CBH 2/CBH 7 Inhibitory Titer >1000 |
|---|---|---|---|
| HCV Sera | 74 | 55 (73%) | 19 (27%) |
| Genotype 1a/1b | 36 | 26 (72%) | 10 (28%) |
| Genotype 2a/2b | 38 | 29 (76%) | 9 (24%) |
| Male/Female | 47/26 | 35/19 | 12/7 |
| Age Median (N) | | 45 (54) | 48 (20) |
| Range | | 31-70 | 40-73 |
| Years HCV + Median (N) | | 5.0 (31) | 5.0 (13) |
| estimated Range | | 0.5-28 | 1-32 |
| Previous Interferon | 18 | 14 (78%) | 4 (22%) |
| Viral Load Median (N) | | $4.7 \times 10^6$ (36) | $2.4 \times 10^6$ (16)* |
| (GEq/ml) Range | | $1.8 \times 10^4$-$2.5 \times 10^7$ | $1.1 \times 10^5$-$6.7 \times 10^6$ |
| ALT Median (N) | | 97 (43) | 124 (15) |
| Range | | 19-4480 | 26-301 |
| Disease Median (N) | | 7.5 (31) | 7.0 (11) |
| Severity (HAI) Range | | 1-11 | 3-13 |
| Cirrhosis | 9 | 8 (86%) | 1 (14%) |

*Significantly different than <1000 group, p = 0.035. Significance testing was performed using the Mann Whitney test.

Example 10

Preparation of HCV E1 and E2 Antigens as Screening Targets and Generation of Human Monoclonal Antibodies Targeting HCV E1 Protein Material and Methods Cell lines and Reagents. HEK-293 cells were maintained in Dulbecco's modified minimal essential medium (DMEM) (GIBCO, Grand Island, N.Y.) supplemented with 10% fetal calf serum (GIBCO) and L-glutamine (2 mM) (GIBCO) in 5% $CO_2$. CHO-K1 cells were maintained in Ham's F12 medium supplemented with 10% fetal calf serum and L-glutamine (2 mM) Clinical serum samples containing HCV viruses in different genotypes were collected by Dr. Gish. Oligonucleotide primers were synthesized by IDT (Corlville, Iowa).

Antibodies and Patient sera. Monoclonal antibody to the influenza hemagglutinin (HA) epitope was raised in rat and obtained from Roche Diagnostics (Indianapolis, Ind.). Monoclonal antibody to HCV E1 (HCM-E1) was obtained from Austral Biologicals (San Ramon, Calif.). Monoclonal antibody to the c-myc epitope was obtained from Santa Cruz Biotechnology (Santa Cruz, Calif.). Eight HCV plasma samples were obtained from blood donors who tested positive for the presence of HCV using standard antibody-based screening assays. Genotype analysis was performed using the InnoLIPA assay according to manufacturer's instructions (Innogenetics, Leuven, Belgium). Sixteen additional HCV 1b plasma samples were obtained from individuals undergoing nucleic acid testing to confirm or follow up a diagnosis of hepatitis C infection between 1996 and 1998. The subjects were positive for HCV RNA by polymerase chain reaction, negative for the presence of hepatitis B virus surface antigen, HCV genotyped, and not receiving antiviral therapy at the time the sample was obtained. Genotype analysis was performed using the InnoLIPA assay according to manufacturer's instructions (Innogenetics, Leuven, Belgium). HCV negative samples consisted of plasma from blood donors to the Stanford Medical School Blood Center, and were negative for the presence of HCV, hepatitis B virus, human immunodeficiency virus and human T-cell lymphotropic virus type1 by standard antibody-based screening assays.

HCV RNA isolation, amplification, and plasmid construction. HCV RNA was isolated from human serum (genotype 1b) using the PureScript (Gentra systems, Minneapolis, Minn.) according to manufacture's instruction. The reverse transcription of HCV RNA was performed with random primers and RT (Perkin-Elmer, Norwalk, Conn.) according to manufacture's protocol at 42° C. for 30 min. Fragments of HCV E1 or E2 were amplified by PCR (pfu, Stratagene) from cDNA with appropriate oligos flanked with Bgl II or Pst I restriction sites. All plasmids were constructed using standard procedures (Maniates et al., 1982). The parent plasmid pDisplay (Invitrogen, Carlsbad, Calif.) contains sequences encoding the murine Ig kappa chain V-J2-C signal peptide and the platelet-derived growth factor receptor transmenbrane domain (PDGFR-TM) with multiple cloning sites in between with transcription driven by the CMV promoter. Bgl II and Pst I cloning sites were used to generate HCV E1 and E2 plasmids where the ORFs are inframe with sequences encoding hemagglutinin A and myc epitopes. Plasmid #38 containing the HCV E2 sequence was constructed by inserting E2 fragments corresponding to amino acids 384-661 into Bgl II and Pst I (New England Nuclear, Boston, Mass.) cloning sites. Plasmids 46, 115, 113, 107, 102 and 98 containing HCV E1 of various lengths were generated by introducing E1 fragments corresponding to amino acids 192-383, 192-370, 192-366, 192-352, 192-340 and 192-321 into Bgl II and Pst I cloning sites. Sequences were confirmed using ABI PRISM Dye terminators cycle sequencing kit (Beckman center, Stanford).

CD81 construct was made using the same method as described above except total RNA was isolated from HEK293. Fragment of CD81 was amplified by PCR (pfu, Stratagene) from cDNA with oligos flanked with Xho I and EcoR I restriction sites. Plasmid CD81 was constructed by inserting the fragment corresponding to nucleotides 239-950 into Bgl II and Pst I (New England Nuclear, Boston, Mass.) cloning sites.

Transfection. HEK 293 cells were seeded prior to transfection to reach a cell density of 50-60% confluence by the following day. Transient transfection was performed using PerFect Lipids™ (Invitrogen) according to manufacture's protocol. For 6-well plate transfection, a mixture of 5 ug DNA and lipid (Pfx-2) at 1:6 ratio (w/w) in serum-free medium was used. Cells were switched to complete medium after 4 hours transfection. Assays for cell surface expression was performed between 24 to 48 hours post-transfection. EGFP (Clontech, Palo Alto, Calif.) was used as an internal control for transfection efficiency.

Creation of Stable Cell Line (Drug Selection). CHO-K1 cells at 50-60% confluence one day after plating were transfected with PerFect Lipid Pfx-8™ (Invitrogen) according to manufacturer's protocol. For 100 mm plate transfections, 29 ug DNA was mixed with Lipid Pfx-8 at 1:6 ratio (w/w) in serum-free Ham's F12-K medium and added to cells. After 5 hours, the cells were switched to complete medium. After incubation overnight at 37° C. in 5% $CO_2$, selection medium consisting of complete medium plus G418 (Gibco BRL, Rockville, Md.) at 450 ug/ml was used to replace the complete medium. After 2 weeks in selection medium, the numerous selected clones were harvested as one population. Subsequently, cells were replated in 100 mm plates with selection medium at various cell densities to enhance the growth of well isolated clones. Ten days later, isolated clones were transferred to 24-well plates by standard technique (Ausubel, Current Protocols in Molecular Biology 2000, John Wiley & Sons INc.) Sterile, $1/8^{th}$ inch cloning disks (PGC Scientific, Gaithersburg, Md.) saturated with equal parts 0.2% trypsin and Versene 1:5000 (Gibco BRL) were placed on top of clones chosen for transfer. After several minutes at room temperature, each trypsin/Versene soaked filter with harvested cells was transferred to a well containing selection medium in a 24-well plate. When cells were nearly confluent, they were harvested, transferred to 12-well plates, and again harvested when nearly confluent. Harvested cells were put onto slides and IFA was performed as described elsewhere. The strongest IFA positive clones were expanded and carried in culture. It was noted that over time the level of protein expression dropped and therefore, cloning by limiting dilution was done by standard method. Briefly, cells were plated at 5, 2, 0.5 and 0.1 cells/well in multiple 96-well, flat-bottom plates in selection medium. Cells from wells containing single clones were transferred to 24-well plates, grown to near confluence and harvested for IFA staining as above. The strongest IFA positive clones were also tested by flow cytometric analysis using standard methods as described below. In summary, cells were stained with CBH-5 and CBH-4G at 10 ug/ml, two anti-E2 HCV human monoclonal antibodies as primary antibodies and with FITC goat anti-human IgG (H & L chain) (Jackson Immunoresearch Laboratories, Inc., West Grove, Pa.) as secondary antibody. One of the strongest positive clones, designated 38-19/5G3, was expanded for assays and has continued to express high levels of HCV E2 protein for several months.

Western blotting. HEK-293 cells were grown on six well tissue culture plates and transfected with various HCV E1 constructs as described above. Twenty-four hours later the cells were washed with PBS and resuspended in 0.5 ml of lysis buffer (150 mM NaCl, 20 mM Tris pH 7.5, 0.5% deoxycholate, 1.0% Nonidet-P40, 1 mM EDTA, 0.5 mg/ml Pefabloc (Boehringer Mannheim, Indianapolis, Ind.), 2 µg/ml Aprotinin, 2 µg/ml Leupeptin, and 1 µg/ml Pepstatin). Nuclei were pelleted by centrifugation at 18,000×g at 4° C. for 10 minutes and resulting cytoplasmic extracts were combined 1 to 1 with 2× sodium dodecyl sulfate polyacrylamide electrophoresis sample buffer (SDS-SB; 20% glycerol, 10% β-mercaptoethanol, 4.8% SDS, 0.125 mM Tris pH 6.8). Alternatively, 24 hours after transfections cells were washed with PBS, resuspended in 100 µl of PBS to which 100 µl of 2×SDS-SB was added. Proteins were denatured via heating to 95° C. for five minutes followed by sodium dodecyl sulfate polyacrylamide electrophoresis (SDS-PAGE) in 12% polyacrylamide gels of 20 µl aliquots of the denatured extracts.

Flow Cytometry. Transient transfected cells were removed from the wells or flasks with Versene 1:5000 (Gibco BRL), washed with staining solution (PBS with 1% FCS and 0.1% sodium azide) and suspended at about $10(10^6)$ cells/ml. Various dilutions of test antibody in a total volume of 100 µl of staining solution were combined with $10^6$ viable transfected or control cells resuspended in 100 µl of staining solution, and incubated at 4° C. for 45 minutes. All dilutions and washes were done in staining solution. Primary test antibodies utilized were anti-HA (Boehringer-Mannheim), anti-E2 (Austral Biologicals) all at 5 ug/ml plus control antibodies anti-T7 RNA polymerase (Novagen, Madison, Wis.) and purified whole rat IgG (Jackson ImmunoResearch Laboratories, Inc.) both at 10 ug/ml. After adding an additional 3 ml of staining solution, the cells were pelleted by centrifugation for 10 minutes at 500×g at room temperature. The pellet was reserved and resuspended in 100 µl of FITC conjugated goat-anti human IgG diluted 1 to 50 in staining solution. After 45 minutes at 4° C., 3 ml of staining solution was added and the cells were pelleted as above. Second step antibodies included R-phycoerythrin (R-PE) conjugated anti-rat, anti-mouse, and anti-human IgG (H+L) (all from Jackson ImmunoResearch Laboratories). Surface expression of target antigens was analyzed on a FACSCalibur flow cytometer (Becton-Dickinson, San Jose, Calif.). The cells were then resuspended in 1 ml of fixative solution (3.8% formaldehyde in PBS) and the amount of HMAb bound to the surface of cells was analyzed on a Becton-Dickinson FACS Vantage flow cytometer (Becton-Dickinson, San Jose Calif.).

Immunofluorescence assay. HEK-293 cells were transfected with various HCV E1 constructs, as described above and were fixed onto HTC Super Cured 24-spot slides (Cel-Line Associates, Newfield, N.J.) with 100% acetone for 10 minutes at room temperature. Fixed cells were incubated with between 3 to 5 µg/ml purified monoclonal antibodies or human serum diluted 1 to 40 in PBS for 30 minutes at 37° C. Slides were then washed for 5-10 minutes with phosphate buffered saline (PBS), pH 7.4 and incubated for 30 minutes at 37° C. with 0.001% solution of Evan's blue counterstain and appropriate fluorescein isothiocyanate (FITC) conjugated secondary antibody (Jackson Immunoresearch laboratories, West Grove, Pa.). Bound antibody was detected by fluorescence microscopy employing a Zeiss Universal microscope.

Results

Figure 30:
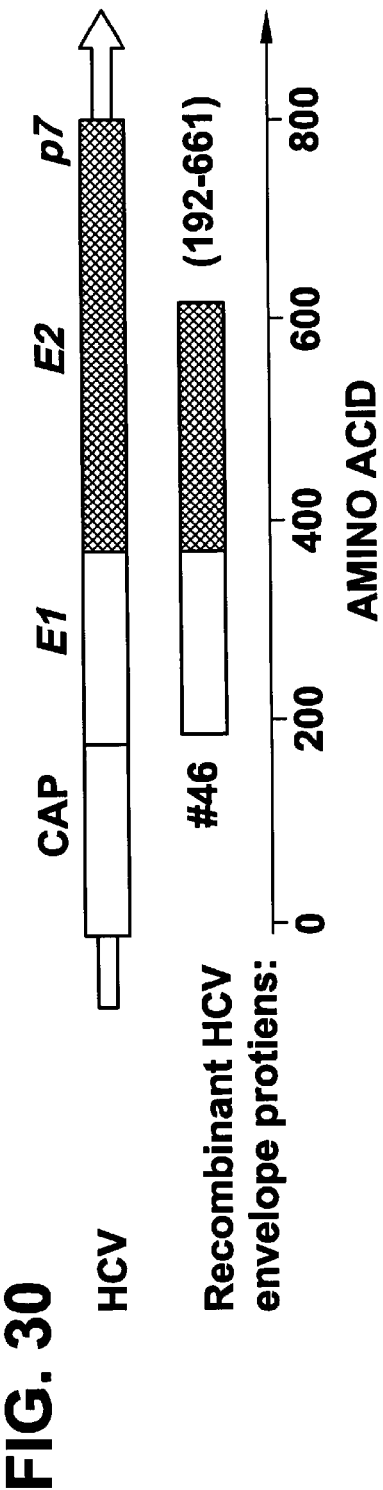
FIG. 30 is a schematic representation of HCV E1 and E1E2 constructs.

Construction of HCVE1 and E1E2 recombinant proteins. Since HCV cannot be reliably propagated in vitro, we used differential binding of antibodies to mammalian cells expressing HCV E1 and E2 envelope proteins to screen antiE1 antibodies from donor plasma. Typically, mammalian cells expressed HCV E1 proteins are in a more native conformation when they expressed on the cell surface. A map of the structural proteins of the HCV genome indicating protein sequences expressed by the HCV constructs employed in these studies is presented in FIG. 30. A series of amino and carboxyl-terminal deletion mutations of the E1& E2 gene were synthesized by PCR and fused to the 3' end of the sequence encoding hemagglutinin A and the 5' end of the sequence encoding myc epitopes. Sequences were confirmed by sequencing. The plasmid vector pDisplay (Invitrogen, Carlsbad, Calif.) contains sequences encoding the murine Ig kappachain V-J2-C signal peptide and the platelet-derived growth factor receptor transmembrane domain (PDGFR-TM). Expression of the constructs were confirmed by Western blot and cell surface expression of the constructs were conformed by flow cytometric analysis after each plasmid was transient transfected into HEK 293 cells.

HCV sequences were amplified from plasma obtained from an individual infected with HCV genotype 1b. DNA sequencing of the E1 region (FIG. 31) revealed 92% identity at the amino acid level with the sequence of the HPCJ491 isolate of HCV 1b (2) and 81% identity with the sequence reported for the HCV 1a strain H (Ogata et al., Proc. Natl. Acad. Sci. USA (1991) 88:3392-3396), on which a majority of previous studies of HCV E1/E2 expression and processing have been performed (Cocquerelet al., J. Virol. (1999) 73:2641-2649; Deleersnyderet al. J. Virol. (1997) 71: 697-704; Dubuisson et al., J. Virol. (1994) 68:6147-6160; Duvet et al., J. Biol. Chem. (1998) 273: 32088-32095; Flint et al., J. Virol. (1999) 73:6782-6790; Flint et al., J. Gen. Virol. (1999) 80:1943-1947; Meunie et al., J. Gen. Virol. (1999) 80: 887-896). The E1 sequence contained five potential N-linked glycosylation sites and a sixth site with the sequence NWSP, which has been previously demonstrated to not be glycosylated (Meunie et al., J. Gen. Virol. (1999) 80: 887-896). The internal hydrophobic domain (amino acids 265-287) and the carboxy terminal hydrophobic domain (amino acids 354-377) can clearly be identified.

The vector pDisplay was employed to express six constructs E1-321, E1-340, E1-352, E1-366, E1-370, and E1-383 that expressed HCV amino acids 192-321, 192-340, 192-352, 192-366, 192-370, and 192-383, respectively. All HCV sequences were expressed in-frame with the transmembrane domain of platelet derived growth factor receptor (PDGFR, see Table 9). Constructs E1-321, E1-340, and E1-352 excluded the carboxy terminal hydrophobic domain of E1; the other constructs included all or part of it (Table 9). The signal sequence at the carboxy terminal of the HCV capsid was replaced with the murine IgK leader sequence. Strong linear epitopes from influenza virus hemaglutinin HA epitope and c-myc epitope are located immediately at N-terminus and C-terminus of the HCV sequences, respectively. All of the constructs were DNA sequenced and contained the expected inserts with no frame shifts or terminations.

ogy (1994) 205: 141-150; Ralston et al. *J. Virol.* (1993) 67:6753-6761; Spaete et al. *Virology* (1992) 188: 819-830).

Glycosylation of HCV E1 constructs. To confirm the presence of glycosyl moieties, HEK-293 cells were transfected with the E1 constructs and cultured for 24 hours in the presence or absence of tunicamycin, which inhibits the initial step of N-linked glycosylation (Kornfield and Kornfield *Ann. Rev. Biochem.* (1985) 54:631-664). HEK-293 cells were transfected with pDisplay vector or the indicated HCV E1 construct and grown in the absence or presence of 2 µg/ml tunicamycin. Twenty-four hours post transfection whole cell extracts were prepared and aliquots were fractionated by SDS-PAGE and blotted onto nitrocellulose. HCV E1 protein

TABLE 9

Characteristics of HCV E1 constructs

| | Leader[1] | | | | HCV E1[2] | | | TM Domain[3] | | | Protein[4] | |
|---|---|---|---|---|---|---|---|---|---|---|---|---|
| Construct | IgK | HA | Link | Fus Pep | Gly (N) | TM (AA) | E1 (AA) | Link | Myc | PDGFR TM | Total AA | Calc MW |
| E1 321 | 21 | 9 | 7 | + | 5 | — | 130 | 4 | 10 | 53 | 234 | 25 |
| E1 340 | 21 | 9 | 7 | + | 5 | — | 149 | 4 | 10 | 53 | 253 | 28 |
| E1 352 | 21 | 9 | 7 | + | 5 | — | 161 | 4 | 10 | 53 | 265 | 29 |
| E1 366 | 21 | 9 | 7 | + | 5 | 14 | 175 | 4 | 10 | 53 | 279 | 30 |
| E1 370 | 21 | 9 | 7 | + | 5 | 18 | 179 | 4 | 10 | 53 | 283 | 31 |
| E1 383 | 21 | 9 | 7 | + | 5 | 31 | 192 | 4 | 10 | 53 | 296 | 32 |

[1]Indicates presence and size (in amino acids) of IgK signal peptide (METDTLLLWVLLLWVPGSTGD), hemaglutinnin (HA) epitope (YPYDVPDYA), and linker amino acids
[2]Indicates presence of putative E1 fusion peptide (Fus. Pep., (Flint, M., Thomas, J. M., Maidens, C. M., Shotton, C., Levy, S., Barclay, W. S., and McKeating, J. A. (1999). Functional analysis of cell surface-expressed hepatitis C virus E2 glycoprotein. J. Virol. 73: 6782-6790), number of N-linked glycosylation sites (Gly), size of the carboxy terminal transmembrane domain (— = not present or number of amino acids), and total size (in amino acids) of E1 portion of construct.
[3]Indicates presence and size (in amino acids) of linker sequence, c-myc epitope (EQKLISEEDL), and PDGFR transmembrane domain (AVGQDTQEVIVVPHSLPFKVVVISAILALVVLTIISLIILIMLWQKKPR).
Indicates total size of protein produced by construct and calculated molecular weight (in kdal) of non-glycosylated protein.

Characterization of HCVE1 and E1E2 Recombinant Proteins.

Figure 32A:
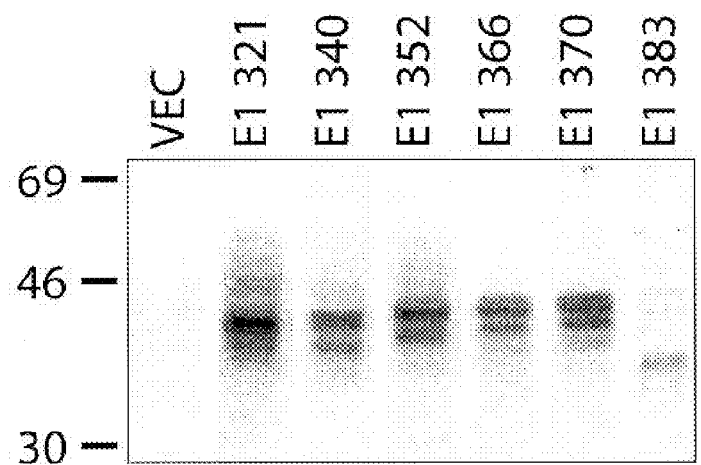
FIG. 32 shows photocopies of Western blots of glycosylated and non-glycosylated E1 constructs. A. HEK-293 cells transfected with pDisplay vector (VEC) or the indicated HCV E1 construct. B. HEK-293 cells were transfected with pDisplay vectors (VEC) or the indicated HCV E1 construct in the presence (+) or absence (−) of tunicamycin.
Figure 32B:
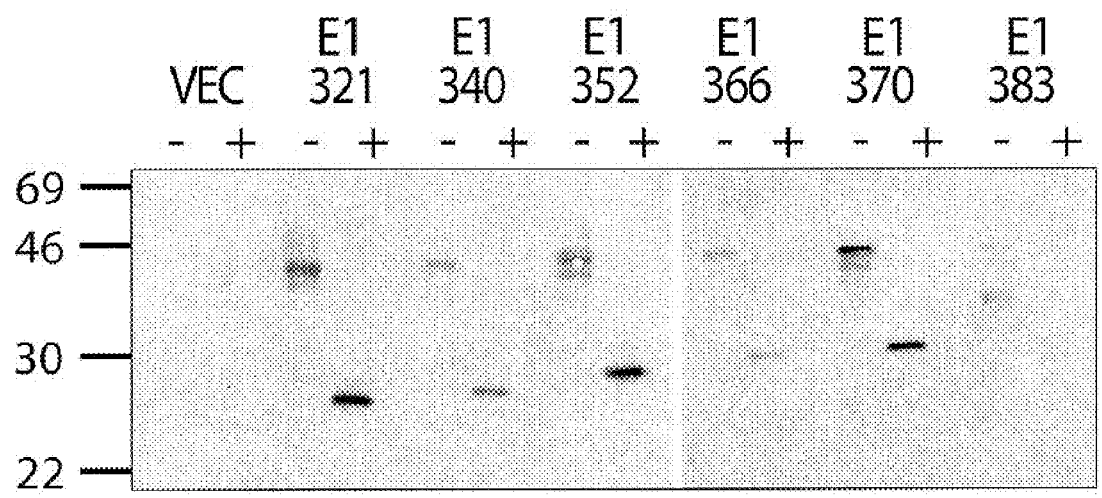

Protein expression analysis. Human embryonic kidney (HEK-293) cells were transfected with each of the HCV E1 pDisplay constructs or HCV E1 vector alone as negative control. After 24 hours, cytoplasmic extracts were prepared and equivalent aliquots were fractionated by SDS PAGE and blotted onto nitrocellulose and Western blotted analyzed upon overnight incubation with 1 µg/ml of the HCM-E1 murine monoclonal antibody to HCV 1a E1 protein (FIG. 32, panel A). Similar results were obtained with a rat monoclonal antibody to the influenza hemagglutinin (HA) epitope. All of the E1 constructs produced multiple immunoreactive bands that migrated with an apparent molecular weight of between 40 to 46 kd. No reactive proteins were observed in cells transfected with the vector alone. Nor were any of the constructs reactive with a control monoclonal antibody that recognized a CMV protein (data not shown). The observed sizes were approximately 12-15 kd larger than the sizes predicted from the amino acid composition of the protein suggesting that the proteins were heavily glycosylated. Surprisingly, the largest of the constructs, E1-383 had the smallest apparent molecular weight of approximately 38 kd. A previous report also indicated that HCV E1 constructs ending at amino acid 384 could migrate faster than shorter constructs (Fournillier-Jacob et al., *J. Gen. Virol.* (1996) 77: 1055-1064). Alternatively, the E1-383 construct may have undergone proteolytic cleavage at or near glycine 383, the site of cleavage between HCV E1 and E2 when the two proteins are expressed co-linearly (Dubuisson et al. *J. Virol.* (1994) 68:6147-6160; Lanford et al. *Virology* (1993) 197:225-235; Matsuura et al. *Virol-* was detected by Western blot analysis after overnight incubation with 1 µg/ml HA rMAb to the HA epitope. (FIG. 33, panel B).

E1 constructs produced in the absence of tunicamycin had molecular weights of 40 to 46 kd, as above, although the expression of multiple immunoreactive bands was less noticeable with the HA monoclonal antibody. Inhibition of glycosylation resulted in the appearance of reactive proteins with molecular weights of 25 to 32 kd for E1-321, E1-340, E1-352, E1-366, and E1-370, which were in good agreement with the predicted molecular weights of the predicted unglycosylated forms of 25, 28, 29, 30 and 31 kd of the five constructs respectively (Table 9). In the absence of tunicamycin, E1-383 was poorly expressed and had an apparent molecular weight of approximately 38 kd. In the presence of tunicamycin, no unglycosylated protein was detectable for construct E1-383. This result indicates that the non-glycosylated E1-383 might be unstable.

Cell surface expression of HCV E1 constructs. The ability of the HCV E1 and E1E2 constructs to be expressed on the cell surface was determined by FACScan analysis. HEK-293 cells were transfected with the HCV E1 or E1E2 constructs. Twenty-four hours post-transfection the cells were harvested, incubated with various monoclonal antibodies and the amount of cell surface staining determined by flow cytometry. Transfection efficiency was monitored by co-transfection of cells with a plasmid expressing green fluorescent protein (data not shown).

Figure 33:
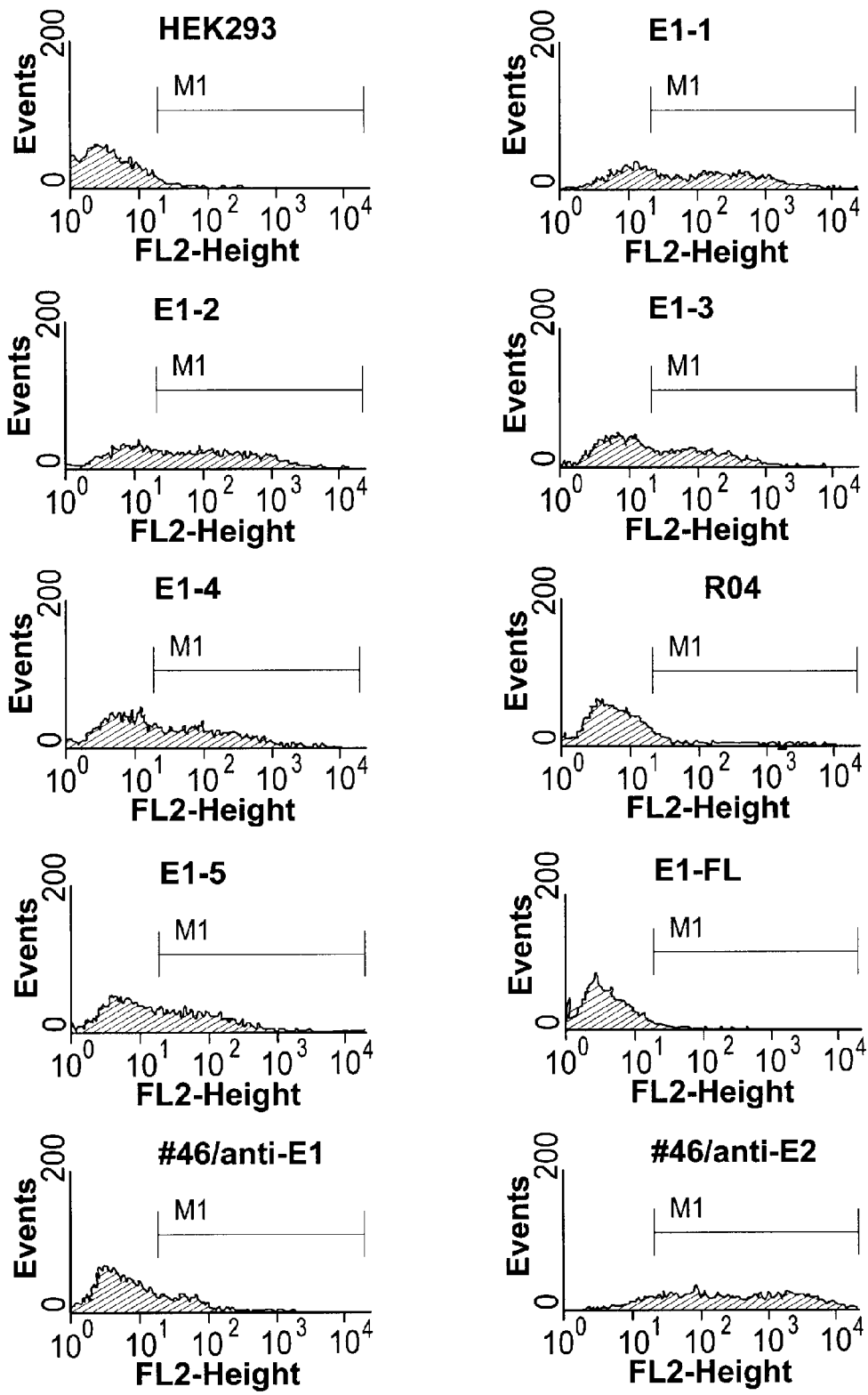
FIG. 33 is a graph representing a FACScan analysis of E1 recombinant proteins expressed in HKE293 cells transfected with E1 deletion constructs.

FIG. 33 shows a FACScan analysis of E1 recombinant proteins expressed in HKE293 cells transfected with E1 deletion constructs. The x axis shows fluorescence intensity and the y axis shows the number of fluorescing cells. HKE293 and R04 (anti-CMV) represent fluorescence obtained in the absence of specific primary antibody. A shift of the area to the right side indicates protein expression on the cell surface. The marker (M1) was used to indicate the range (0-100%) of fluorescence considered above background. The recombinant peaks were detected with HCM-E1 murine MAb.

As shown in FIG. 33, only background levels of staining were observed with a control antibody R04 (anti-CMV). With the mouse HCV E1 antibody (HCM-E1 mMAb) to the recombinant E1 proteins, high levels of cell surface expression were obtained with the constructs E1-321, E1-340, E1-352 and E1-366. An intermediate level of surface expression was seen with the constructs E1-370, no cell surface expression was observed with E1-383. The transfection efficiency obtained with all constructs was similar (~40%) thus suggesting that the reduced levels of cell surface expression seen with E1-370 and E1-383 were not due to variations in transfection efficiency. In addition, intracellular expression of the constructs as measured by fixed cell immunofluorescence was comparable (FIG. 34).

Immunoreactivity to E1 human antibodies in HCV positive serum. Having achieved significant cell surface expression with 5 of 6 E1 constructs, the immunoreactivity of the E1 constructs with a panel of sera from individuals infected with genotype 1 HCV was evaluated (Table 10). HEK-293 cells were transfected with each of the E1 constructs and fixed onto glass slides for IFA. The approximate transfection efficiency was determined by incubating the fixed cells with HA monoclonal antibody.

Figure 34:
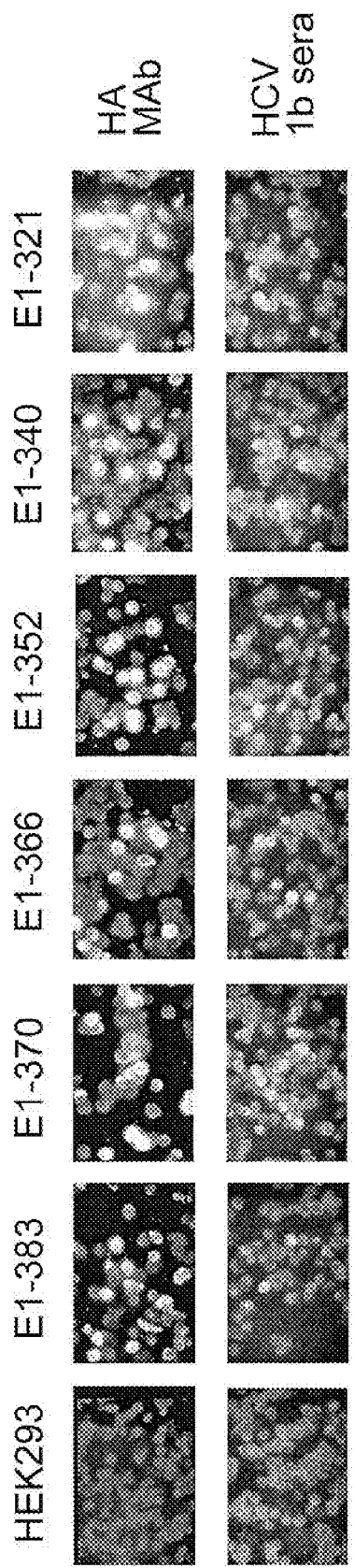
FIG. 34 shows a panel of photographs representative of IFA data suing HCV serum.

FIG. 34 shows representative IFA data with HCV serum. HEK293 cells transfected with the indicated constructs or untransfected HEK293 cells were fixed onto slides with acetone and stained with rat monoclonal antibody to HA at 5 mg/ml or an HCV serum at dilution 1:50. Slides were counterstained with 0.001% solution of Evan's blue counterstain and bound antibody was detected with fluorescein isothiocyanate (FITC) conjugated goat-anti-human or anti-rat IgG. Strong staining was observed in approximately 50% of the transfected cells for each of the constructs. No staining was observed with eight sera from HCV negative blood donors with any of the E1 constructs (Table 10). When cells transfected with the E1 constructs were tested with sera from HCV 1b infected individuals at a dilution of 1 to 40, a moderate level of positive staining was observed. Staining obtained with a representative serum is presented in FIG. 34.

One of the sera had strong reactivity to non-transfected HEK-293 cells (Table 10). Five of the six HCV E2 constructs were reactive with 54 to 71% of the HCV 1b sera tested (FIG. 35 ADDED). Construct E1-383 was the least reactive at 33% (8 of 24 sera). Excluding E1-383, reactivities of the E1 constructs with HCV genotype 1 antisera are comparable to the reactivity observed in a study using secreted E1 protein (Gane et al. *Transplantation*. (1999) 67: 78-84.). E1-352 was selected as an antigen for E1 HMAbs screening since it showed highest reactivity (71%) to HCV positive sera.

Selection of the blood donor for HCV E1 HMAbs screen. Among the 17 HCV 1b positive sera tested (Table 10), donor HC29 showed high titer serum antibodies to HCV E1 constructs. Peripheral blood B-cells were isolated from this individual and successfully used to generate HCV E1 antibody secreting human hybridomas.

TABLE 10

Summary. Reactivity of HCV Sera with E1 constructs

| Sera | N | HEK 293[a] | E1-321 | E1-340 | E1 352 | E1 366 | E1 370 | E1 383 |
|---|---|---|---|---|---|---|---|---|
| HCV 1b | 17 | 1 | 12 | 13 | 14 | 12 | 13 | 8 |
| HCV 1a | 7 | 0 | 2 | 2 | 3 | 1 | 2 | 0 |
| Total HCV | 24 | 1 (4%) | 14 (58%) | 15 (63%) | 17 (71%) | 13 (54%) | 15 (63%) | 8 (33%) |
| HCV Neg | 8 | 0 | 0 | 0 | 0 | 0 | 0 | 0 |

Indicates number of positive sera (%). A serum was considered positive if greater than 5% of the transfected cells were judged to exhibit clear immunofluorescence, similar to that exhibited by the HCV 1b serum of FIG. 34.

Production of antigen-specific human monoclonal antibodies. Having achieved significant cell surface expression with two of the E1 constructs, the larger protein, E1-352, was employed to evaluate the seroreactivity of HCV infected individuals to E1. Accordingly, the plasmid expressing E1-352 was introduced into HEK-293 cells and a cell line expressing E1-352 was obtained. The E1-352 expressing cells were then fixed onto glass slides for Indirect Fluorescence Assay (IFA). The reactivity of the cells with a panel of sera from blood donors, which were found to be PCR positive for HCV genotype 1, was determined. Eleven out of 23 (48%) blood donors with HCV genotype 1 infection were reactive with the E1-352 protein. This contrasted with zero out of eight HCV negative blood donors and six out of nine (67%) patients with HCV hepatitis. The donor with the strongest antibody response to E1-352 (FIG. 34, panel HCV 1b) was used as the source of peripheral B cells for hybridoma isolation. Accordingly, a second aliquot of blood was obtained from this individual and both plasma and mononuclear cells were isolated. The donor was an asymptomatic, 51 year old, Hispanic male who was not aware of his HCV status prior to the donation. Testing of a second sample drawn 11 months later confirmed that the donor retained a strong antibody response to E1-352.

Figure 36:
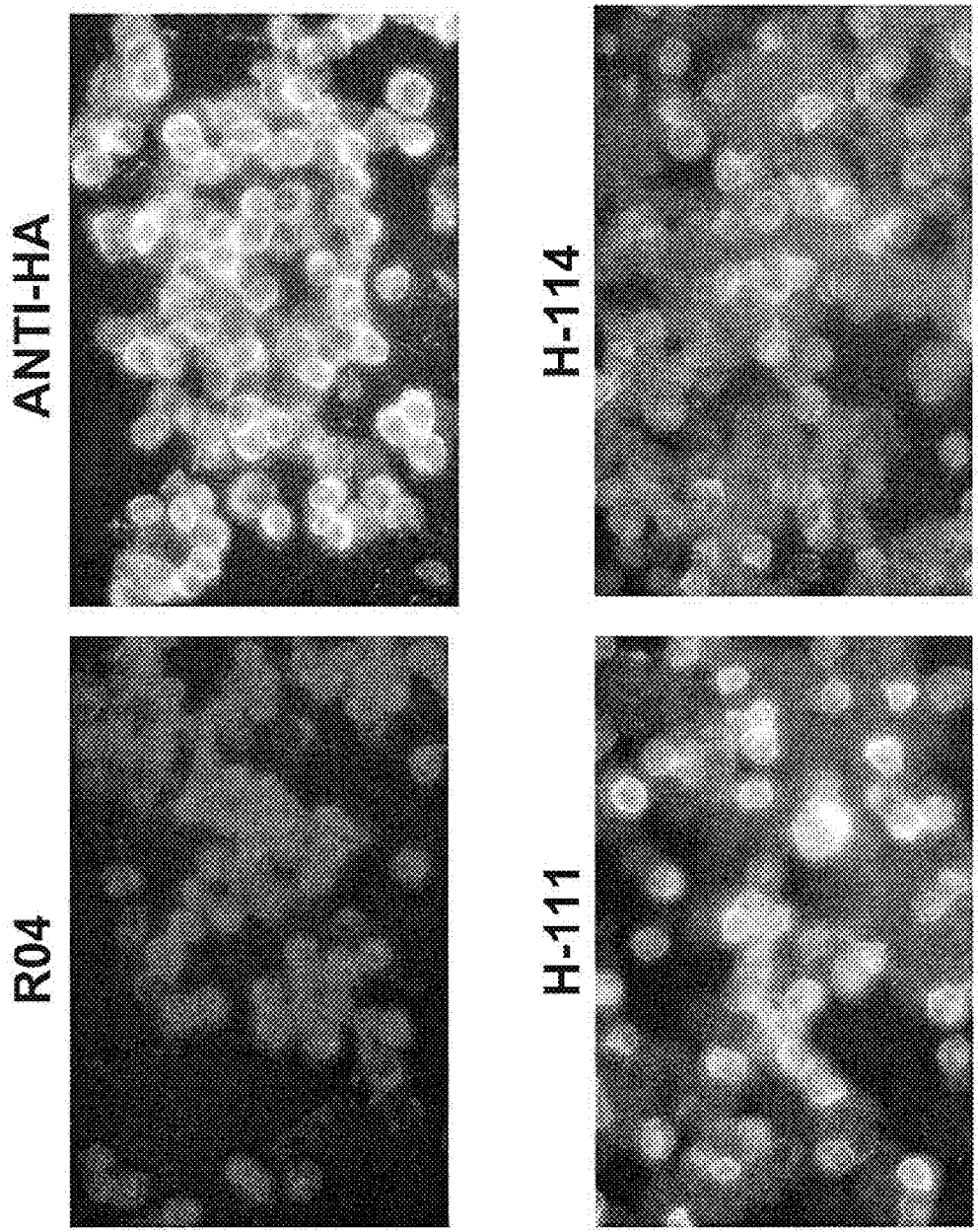
FIG. 36 shows photographs of IFA data with HCV anti-E1 HMAbs H-111 and H-114.

Peripheral B cells were then isolated, activated with Epstein Barr virus, and cultured for 16 to 30 days. IFA with E1-352 expressing cells resulted in the identification of 7 out of 417 wells (~2%) with antibodies to E1-352. EBV activated cells ($2-13 \times 10^5$) from the 7 E1-reactive wells were then fused to $K_6H_6$/D5, a mouse-human heteromyeloma fusion partner, at a ratio of 1 EBV-activated cell: 2 $K_6H_6$/D5 cells in hypo-osmolar (125 L3 or 180 L3), or iso-osmolar (300 L3) fusion medium. Two hybridomas were isolated that, after cloning, secreted 1 to 80 ug human IgG per ml. Both antibodies were strongly reactive with E1-352 by IFA (FIG. 36). In the experiments shown in FIG. 36, HEK293 cells transfected with E1-3 construct or CD4 construct in the same parent vector were fixed onto slides at a ratio of 1 to 2 with acetone and stained with H-111, H-114, R04 (anti-CMV HMAb) at 10 ug/ml or rat monoclonal antibody to HA at 5 ug/ml. Slides were conterstained with 0.001% solution of Evan's blue counterstain and bound antibody was detected with fluorescein isothiocyanate (FITC) conjugated goat-anti-human or anti-rat IgG. Hybridoma H-111 expressed an IgG1 (K1) with heavy chain sequencing revealing greatest homology to the VH3-30 germline sequence. Hybridoma 114 (H-114) expressed an IgG1 (K2) whose heavy chain was most homologous with the VH1-3 germline sequence.

Figure 37:
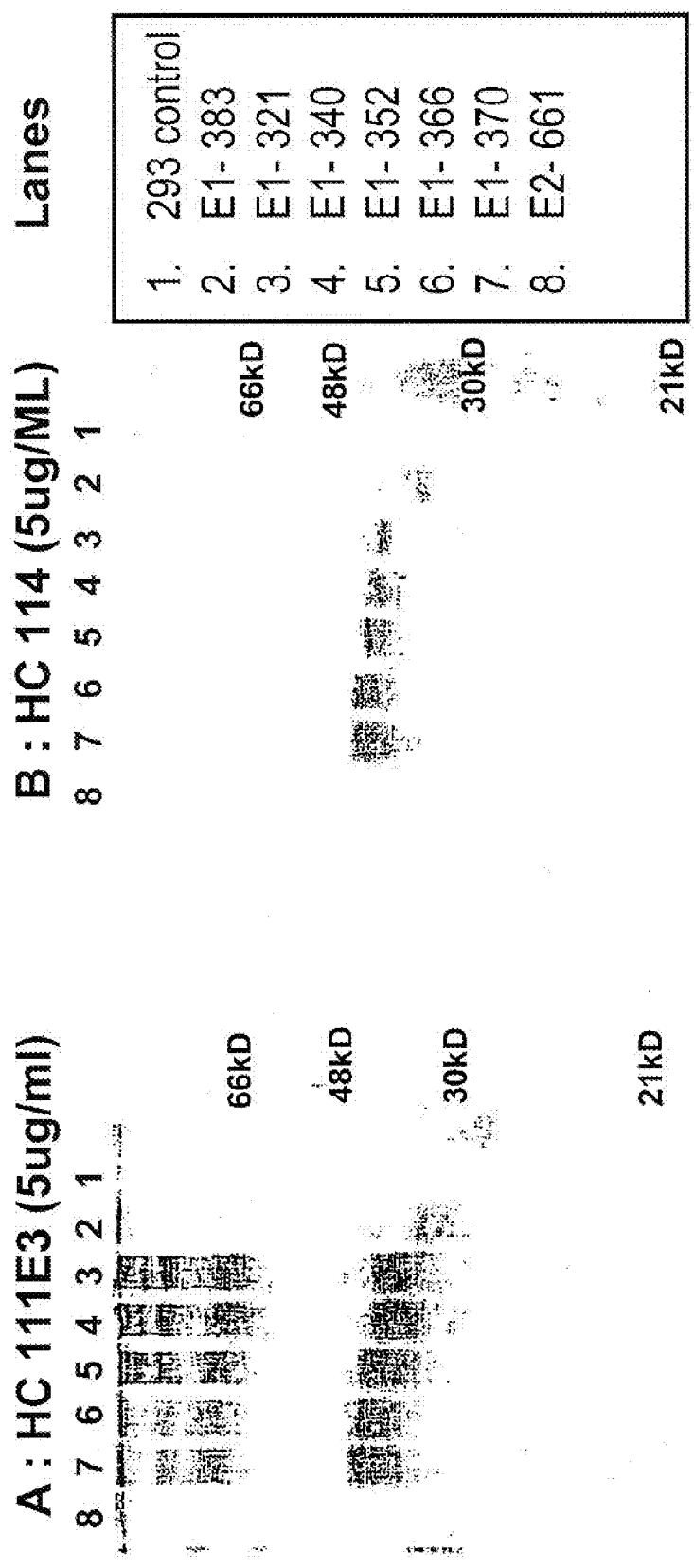
FIG. 37 shows Western blots of E1 proteins with HMAbs H-111 and H-114. A. Immunoprecipitation. B. Western Blot.

Reactivity of E1 HMAbs with HCV envelope proteins. To confirm the results obtained by IFA with fixed cells, the HMAbs H-111 and H-114 were tested for reactivity with various E1 proteins/E1-352 by Western blot and immunoprecipitation assay (FIG. 37). HEK-293 cells were mock transfected (0) or transfected with the indicated HCV E1 constructs or pDisplay E2 (optional) and 24 hours post transfection cytoplasmic extracts were prepared. Aliquots of the extracts were then subjected to immunoprecipitation with 5 ug of the H-111 or H-114 HMAb, as described in the Materials and Methods. Bound protein was then eluted with SDS sample buffer and subjected to SDS-PAGE and Western blot. Blotted E1 protein was detected with 2 ug/ml of the ECM E1 murine antibody. For the Western Blot, HEK-293 cells were transfected with the indicated HCV E1 construct or mock transfected. Twenty-four hours post transfection, cytoplasmic extracts were prepared and equivalent aliquots were fractionated by SDS PAGE and blotted onto nitrocellulose. HCV E1 protein was detected by overnight incubation with 5 μg/ml of HMAb H-111 or H-114.

As shown in FIG. 37, HMAb H-111 was strongly reactive with E1-352, E1-340, and E1-321 by both Western blot and immunoprecipitation. HMAb H-114 was strongly reactive with the E1 proteins by Immunoprecipitation but was weakly positive by Western blot. No reactivity was observed with an isotype control HMAb with any of the E1 constructs by Western blot or immunoprecipitation. Thus, HMAb H-111 recognizes a denaturation insensitive epitope within E1-321. HMAb H-114 recognized an epitope within E1-321 that appeared to be partially susceptible to denaturation.

The E1 HMAbs were isolated using an E1 construct that exhibited a significant level of expression on the surface of cells. However, IFA was used to identify the HMAbs; raising the possibility that the HMAbs were specific for intercellular forms of the E1-352 protein. To confirm that the HCV HMAbs also recognized E1-352 on the surface of cells the reactivity of the E1 HMAbs with HEK-293 cells expressing E1-352 was determined by flow cytometry. FIG. 38 shows a FACScan analysis of HCV HMAbs H-111 and H-114 with E1-1 recombinant protein transient expressed in HEK293 cells. The x axis shows fluorescence intensity and they axis shows the number of fluorescent cells. R04 (anti-CMV) represents fluorescence obtained in the absence of specific primary antibody. A shift of the area to the right side indicates antibody binding and anti-HA represents HA tag expression as fusion protein. The marker (M1) was used to indicated the range (0-100%) of fluorescence considered above background. The data in FIG. 38 indicates that both H-111 and H-114 recognized cell surface expressing E1-352.

Reactivity of HCV HMAbs with HCV Envelope Protein Isolates from Multiple Genotypes. To test conservation of HMAb epitopes, HCV RNA isolated from various HCV genotypes was reverse transcribed and amino acids 192-352 region was amplified and cloned into the pDisplay vector. Recombinant plasmids were transfected into HEK-293 cells and the reactivity of the HMAbs with the constructs was assessed by IFA and confirmed by Western blot analysis. HEK293 cells were transfected with HCV E1 constructs comprising E1 genes cloned from indicated HCV genotypes and analyzed by an immunofluorescence assay (IFA). The protein extracts of the transfected cells prepared twenty-four hours post-transfection were fixed onto slides with acetone and stained with rat monoclonal antibody to HA at 2 ug/ml, HMAbs at 5 ug/ml or an human monoclonal antibody to CMV at 5 ug/ml. Slides were counterstained with 0.001% solution of Evan's blue counter stain and bound antibody was detected with fluorescein isothiocyanate (FITC) conjugated goat-anti-human or anti-rat IgG. Results obtained with the entire panel of E1 proteins are presented in Table 11 and Table 12.

TABLE 11

Summary Reactivity of HMAbs with HCV E1 protein isolates from multiple genotypes

| HCV E1 Protein | anti-HA (positive control) | HC-111 (HMAb) | HC-114 (HMAb) | anti-CMV (negative control) |
|---|---|---|---|---|
| HCV 1b | +++ | +++ | +++ | − |
| HCV 1a | +++ | +++ | − | − |
| HCV 2b | +++ | +++ | − | − |
| HCV 2a | +++ | − | − | − |
| HCV 3a | +++ | ++ | − | − |
| HCV 4 | +++ | − | − | − |
| HCV 1b | +++ | +++ | +++ | − |
| HCV 1a | +++ | +++ | − | − |
| HCV 2b | +++ | +++ | − | − |
| HCV 2a | +++ | − | − | − |
| HCV 3a | +++ | ++ | − | − |
| HCV 4 | +++ | − | − | − |

TABLE 12

HCV positive sera employed in genotype study

| Genotype | Serum |
|---|---|
| HCV 1b | HC-29 |
| HCV 1a | HC-03 |
|  | HC-06 |
|  | HC-16 |
| HCV 2b | V5704 |
|  | V6674 |
|  | V3551 |
| HCV 2a | 189 |
|  | V3402 |
|  | V2238 |
|  | S0208 |
|  | S0223 |
| HCV-3a | 2180 |
|  | 1966 |
|  | 2255 |
|  | S0126 |
|  | S0236 |
| HCV-4a | S0159 |
|  | S0652 |

The presence of transfected proteins was verified with the HA MAb. Typically between 20 to 40 percent of the cells were positive with the HA MAb. Both HMAbs were reactive with E1 protein isolated from the B cell donor (HC-29). HMAb H-111 was reactive with 17 of the 19 E1 proteins from different infected individuals, including all proteins of genotypes 1a, 1b, 2b, and 3a. HMAb H-111 was not reactive with 10 E1 proteins represent genotype 2a isolated from 5 different infected individuals. Thus the epitope recognized by HMAb H-111 might be mutated in genotype 2a. HMAb H-111 was also non reactive with an E1 protein of genotype 4. HMAb H-114 did not react with any E1 protein except that it was isolated against (E1-352) and that of the B cell donor (HC-29). Thus HMAb H-114 expresses an HCV 1b specific epitope.

Figure 39:
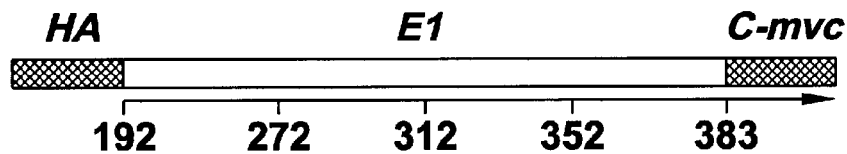
FIG. 39 is a chart showing epitope mapping experiments of E1 HMAbs.

Epitope localization of E1 HMAbs. A series of deletions were introduced into the carboxyl and amino terminals of E1-352 to localize the epitopes recognized by the two HMAbs. The E1 deletion constructs were then transfected into HEK-293 cells and extracts containing the proteins were subjected to Western blot and IFA with HMAbs H-111 and H-114. Expression of the proteins was verified using the HA MAb. The results obtained are summarized in FIG. 39. HMAb H-111 was reactive all of the carboxy terminal deletion constructs including a construct limited to the amino terminal 20 amino acids of E1-352. In contrast HMAb H-114 was reactive with E1-321 and a construct expressing amino acids 192-313 but not any of the other carboxy terminal constructs. Deletion of as little as five amino acids from the amino terminal of E1-352 was sufficient to abrogate reactivity of HMAb H-111. Thus the epitope of HMAb H-111 was located proximal to the amino terminal of E1-352. In contrast HMAb H-114 was reactive with constructs expressing amino acids 192-313, 199-321, and 206-321, but not constructs expressing amino acids 212-313, 244-313, and 262-313. Thus the epitope of HMAb H-114 is located between amino acids 206-313 of E1-352 but could not be further defined.

Peptide competition analysis of HMAb H-111 epitope. The HCV E1 epitope bound by HMAb H-111 (amino acids 192-211) contains two glycosylation sequences. This epitope is also conserved in many of the HCV subtypes, despite a comparatively high degree of variation in the amino acid sequences of the E1 amino terminal. This raised the possibility that the glycosyl moieties of the E1 amino terminal might be involved in the epitope recognized by HMAb H-111. To address this possibility synthetic peptides comprising the amino terminal 7 and 14 amino acids of HCV E1 were synthesized (Table 13).

TABLE 13

Amino acid sequence of the synthetic peptides for epitope binding competition.

| Peptide code | Peptide | Amino Acids Sequence |
|---|---|---|
| H-111-7 | 192-198 | YEVRNVS |
| H-111-14 | 192-205 | YEVRNVSGVYHVTN |
| H-114-12 | 304-315 | CNCSIYPGHVYG |
| H-114-6 N | 206-211 | DCSNSS |

Since the synthetic peptides would not be glycosylated, successful competition for HMAb binding would indicate that glycosylation was not required for antibody binding. E1-352 produced from transfected HEK-293 cells was captured onto microtiter plates using GNA lectin. Then binding of HMAb H-111 was assessed in the presence of increasing amounts of the various synthetic peptides. HEK-293 cells were transfected with E1-352 and E1 glycoproteins were captured onto microtiter plates coated with 500 ng of GNA lectin. Wells were washed and blocked and bound protein was incubated with 10 ug/ml of HMAb H-111 in the presence of increasing amounts (x axis) of control synthetic peptides. μ control HTLV peptide; σ E1 peptide YEVRNVS; υ E1 peptide YEVRNVSGVYHVTN). The y axis indicates the mean OD values derived from replicate wells. The error bars indicate one standard deviation from the mean.

Figure 40:
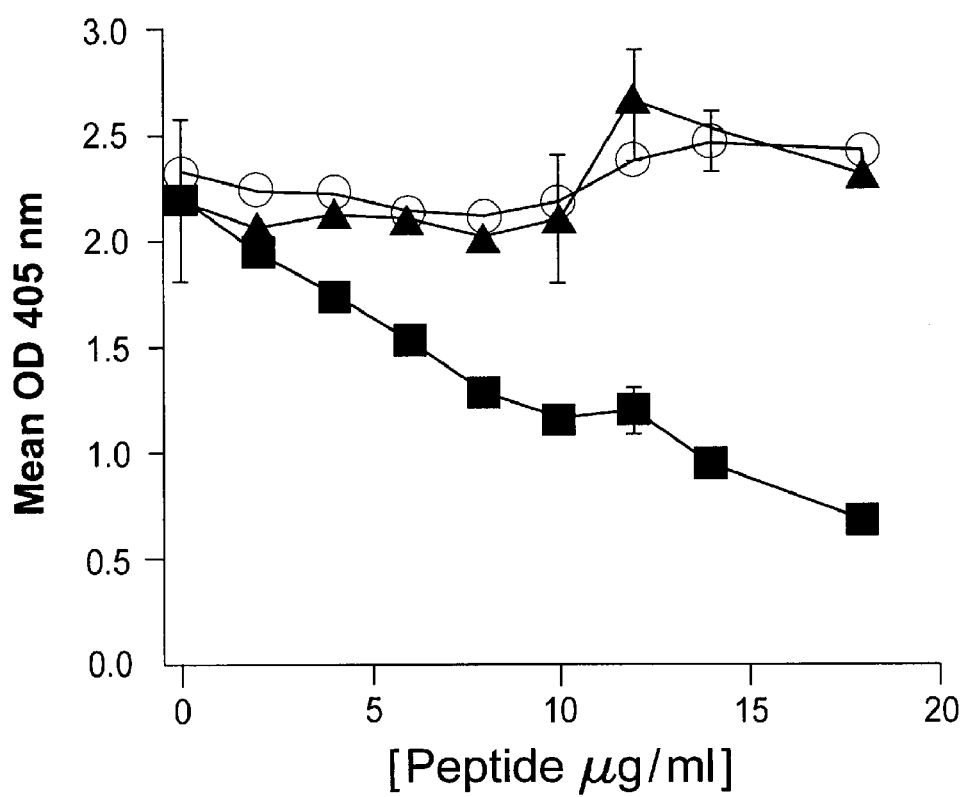
FIG. 40 is a graph illustrating a peptide competition analysis of HMAb H-111 epitope.

In the absence of peptide HMAb H-111 was strongly reactive with GNA captured E1-321 (FIG. 40). The addition of an irrelevant peptide from HTLV-1 gp46 had no affect on binding of HMAb H-111 to E1-321. Nor did the 7 amino acid peptide affect binding of HMAb H-111. In contrast, addition of the 14 amino acid peptide resulted in a dose dependent inhibition of binding of HMAb H-111 to E1-321. Thus, the HMAb H-111 epitope does not require glycosylation to be recognized.

Epitope mapping of HMAb H-111 with alanine scanning. To obtain a fine map of the HMAb H-111 epitope on the 14-mer peptide spanning amino acids 192-204 of E1 glycoprotein, we introduced conservative (Alanine) amino acid substitution over 11 positions in this 14-mer competing peptide (position 192-Tyr, 193-Glu, 194-Val, 195-Arg, 196-Asn, 197-Val, 198-Ser, 199-Gly, 200-Val, 201-Tyr, and 202-His) (Table 14).

TABLE 14

Epitope mapping.
YEVRNVSGVYHVTN

| | | IFA & comments | | |
|---|---|---|---|---|
| Constructs | Mutations | HA | H-111 | R04 |
| 107 | E1-352 WT | + | + | -- |
| 783 | E1-192 Y/A | + | + | -- |
| 784 | E1-192 Y/A | + | + | -- |
| 787 | E1-193 E/A | + | + | -- |
| 789 | E1-193 E/A | + | + | -- |
| 792 | E1-194 V/A | + | Weak+ | -- |
| 793 | E1-194 V/A | + | Weak+ | -- |
| 796 | E1-195 R/A | + | +-- | -- |
| 797 | E1-195 R/A | + | +-- | -- |
| 798 | E1-195 R/A | + | +-- | -- |
| 799 | E1-195 R/A | + | +-- | -- |
| 800 | E1-196 N/A | + | -- | -- |
| 801 | E1-196 N/A | + | -- | -- |
| 802 | E1-196 N/A | + | -- | -- |
| 803 | E1-196 N/A | + | -- | -- |
| 804 | E1-197 V/A | + | + | -- |
| 805 | E1-197 V/A | + | + | -- |
| 808 | E1-198 S/A | + | Weak <5% | -- |
| 810 | E1-198 S/A | + | Weak <5% | -- |
| 811 | E1-198 S/A | + | Weak <5% | -- |
| 812 | E1-198 S/A | + | Weak <5% | -- |
| 813 | E1-199 G/A | + | Weak <5% | -- |
| 814 | E1-199 G/A | + | Weak <5% | -- |
| 815 | E1-199 G/A | + | Weak <5% | -- |
| 816 | E1-199 G/A | + | Weak <5% | -- |
| 886 | E1-200 V/A | + | + | -- |
| 887 | E1-200 V/A | + | + | -- |
| 890 | E1-201 Y/A | + | -- | -- |
| 891 | E1-201 Y/A | + | -- | -- |
| 894 | E1-202 H/A | + | + | -- |
| 895 | E1-202 H/A | + | + | -- |

Figure 41:
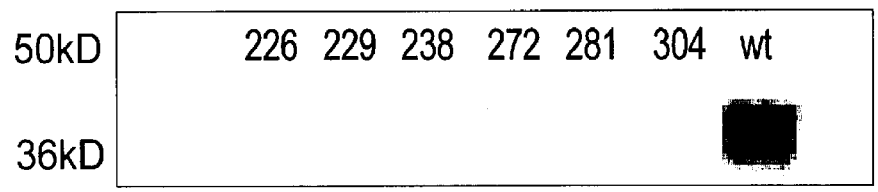
FIG. 41 is a photograph of a Western blot of mutated E1 recognized by H-114.

The amino acid sequence of H-111 epitope on E1 glycoprotein is indicated on top of Table 14 in single letter-code. R at position four, N at position five, and Y at position ten are essential amino acids and VSG at positions three, seven and eight are crucial amino acids for HMAb H-111 binding to E1 glycoprotein. Numbers at the mutation site indicate amino acid expressed by each construct and are relative to the entire HCV polyprotein. The reactivity to each protein with the HA mMAb (positive control), HMAb R04 (negative control) or the H-111 HMAb by IFA is indicated as positive (+) or negative (−). The mutated E1 was expressed in CHO cells and analyzed by both IFA (Table 14) and Western Blotting (FIG. 41) using HMAb H-111, mMAb HA as positive control and R04, which is anti-CMV human monoclonal antibody as negative control. All of the mutants were expressed in CHO cells in approximately equal amounts and at approximate molecular weight of the wild type E1-352 glycoprotein. Amino acid substitution occurring at 195-Arg, 196 Asn, and 201-Tyr profoundly affected binding activity of HMAb H-111 to E1 glycoprotein and at 194-Val, 198-Ser, and 199-

Gly remarkably weakened binding activity of HMAb H-111 to E1 glycoprotein, but did not completely diminish the binding, indicating that the central region on the 14-mer competing peptide is important for the interaction between antibody and HCV E1 envelope protein. Substitution corresponding to amino acids 192-Tyr, 193-Glu, 197-Val, 200-Val, and 202-His did not affect the binding activity of HMAb H-111 to E1 glycoprotein. These results suggest that epitope for HMAb H-111 consists at least five amino acid residues Val (194), Arg (195), Asn (196), Ser (198), Gly (199), and 201-Tyr, and is within amino acid 194 to 204.

Peptide competition analysis of HMAb H-114 epitope. The two discontinuous HMAb H-114 epitopes, CSIYPGHV at C-terminus and DCSNSS at N-terminus, were defined by deletion mapping presented above, consist of one glycosylation sequence (209-NSS) and two Cysteine residues (Cys-306 and Cys-207) located approximate 100 amino acid apart. This raised the possibility that the glycosyl moieties of the E1 amino terminal might be involved in the epitope recognized by HMAb H-114 and/or intramolecular disulfide bond formation is required for HMAb H-114 epitope recognition. To address these possibilities two synthetic peptides comprising the amino terminal 6 or 12 amino acids of HCV E1 were synthesized (Table 13). Since the synthetic peptides would not be glycosylated, successful competition for HMAb binding would indicate that glycosylation was not required for antibody binding.

Figure 42:
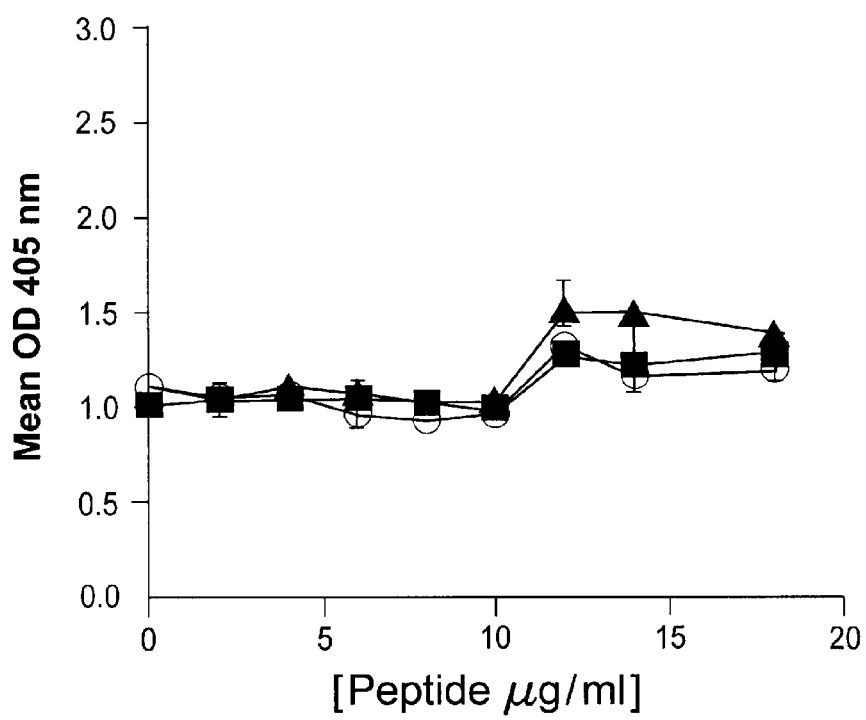
FIG. 42 is a graph illustrating a peptide competition analysis of BMAb H-114.

Truncated E1-352 and E1 glycoproteins glycoproteins produced from transfected HEK-293 cells was captured onto microtiter plates using 500 ng GNA lectin. Binding of HMAb H-114 was assessed in the presence of increasing amounts of the two synthetic peptides. Specifically, wells were washed and, blocked, and bound protein was incubated with 10 ug/ml of HMAb H-114 in the presence of increasing amounts (x axis) of control synthetic peptides. (Peptide H-114-12-C corresponding to the C terminus region from amino acids 304 to 315 on the E1 glycoprotein and peptide H-114-14-N corresponding to the N terminus region from amino acids 206 to 211 on the E1 glycoprotein). The addition of these two synthetic peptides had no apparent effect on the binding activity of HMAb H-114 to truncated E1-352 protein (FIG. 42), nor did control peptide, which correspond to immunodominant region on HTLV-1 gp46. These data indicate that (i) the two discontinuous HMAb H-114 epitopes may require glycosylation to be recognized; (ii) the two discontinuous HMAb H-114 epitopes may not be the antibody binding sites but instead the epitope is between the two epitopes where amino acids spanning from 216 to 303; and (iii) the 108 amino acid sequence defined by the deletion constructs may contain structural features, such as a compact domain or disulfide bonds that are required for presentation of the epitope recognized by HMAb H-114.

Serine or alanine scan of amino and carboxyl terminal regions of HMAb H-114 epitope. To discriminate between these possibilities a series of serine or alanine substitutions were introduced into amino acids 206-211 and 306-313. The modified E1s were then transfected into HEK-293 cells and the E1 proteins were captured onto microtiter plates with GNA lectin. The reactivity of HMAb H-114 with the bound E1 proteins was then determined by mutational analysis of amino terminal amino acids 206 to 211 or carboxy terminal amino acids 306-313 (FIG. 43). HEK-293 cells were transfected with E1 proteins with the substitutions indicated in FIG. 43 and E1 glycoproteins were captured onto microtiter plates coated with 500 ng of GNA lectin. Wells were washed and blocked and bound protein was incubated with 5 ug/ml of the HA mMAb (solid bars) or 10 ug/ml of HMAb H-114. Bound antibody was detected with the appropriate alkaline phosphatase conjugated secondary antibody and PNPP substrate. The x axis indicates the signal obtained with each mutant expressed as a percentage of the signal obtained with wild type E1 sequence. The error bars indicate one standard deviation from the mean. To adjust for variation in protein expression that might result from the point mutations, the reactivity of the constructs with the HA MAb was also determined. The signal obtained was compared to that of the unmodified protein E1-321.

As shown in FIG. 43, substitution of the cysteine residue in the amino terminal sequence DCSNSS specifically abrogated binding of HMAb H-114 but not the HA antibody. In contrast, mutation of the asparagine or serine residues of the glycosylation site NSS resulted in equivalent reductions in signal in both the HA and H-114 antibodies. Thus, the amino-terminal glycosylation site is probably not implicated as contributing to the HMAb H-114 epitope. Similarly, for the sequence CSIYPGHV, mutation of the cysteine residue also abrogated binding of HMAb H-114 without affecting binding of HA. The reason for the stimulation of HA binding by the sequence CSISPGHV is not known. However the binding of HMAb H-114 was unaffected, suggesting that Y-309 is not part of the H-114 epitope.

Figure 44:
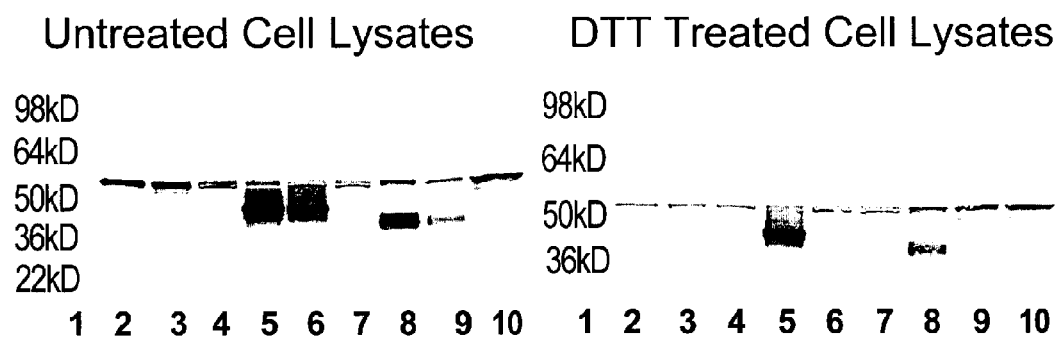
FIG. 44 shows photographs of immunoprecipitation analyses on binding of HMAb H-114 to E1 in the presence and absence of DTT.

Binding of HMAb H-114 to E1 is disulfide dependent. The requirement for two cysteines to maintain the HMAb H-114 epitope, suggests that disulfide bond formation is required for presentation. Under these conditions disulfide bonds should also abrogate HMAb H-114 binding. This was confirmed by pre-treating cell lysates of E1-321 with DTT prior to immunoprecipitation with HMAb H-114 (FIG. 44). HEK-293 cells were transfected with E1-321 and 24 hours after transfection cytoplasmic extracts were prepared. Aliquots of the extract were either left untreated or incubated with 5 mM dithiothreitol for 15 minutes at 56° C. Extracts were diluted 1:5 in ice-cold BLOTTO and subjected to immunoprecipitation with various antibodies (indicated above lanes). Bound protein was then eluted with SDS sample buffer and subjected to SDS-PAGE and Western blot.

No precipitation of E1-321 was observed with a control HMAb. In the absence of DTT pre-treatment, both HMAbs H-111 and H-114 precipitate a 46 kdal protein that reacts with a monoclonal antibody to E1. After pre-treatment with 5 mM DTT at a temperature of 56 C, binding of HMAb H-111 to E1 is unaffected. In contrast, binding of HMAb H-114 is completely abrogated. Thus the epitope recognized by HMAb H-114 depends on the formation of disulfide bonds that involve C-207 and C-306.

Alanine scanning on internal E1 cysteine residues. E1 glycoprotein contains 8 cysteine residues at positions 207, 226, 229, 238, 272, 281, 304 and 306 that could form intramolecular disulfide bonds. Expression of 6 of E1 mutants substituted C to A was analyzed (FIG. 45) to determine whether the cysteine residues internal of 207-cys and 306-cys are involved in structure formation of the epitope recognized by HMAb H-114. First, E1 mutants were expressed in CHO cells following transient transfection with the corresponding plasmids and analyzed by IFA. As shown in FIG. 45, all mutated proteins were expressed and recognized by a mouse MAb HA targeting the tag epitope as positive control. All mutated proteins were recognized by HMAb H-111 targeting an epitope located between amino acid 192-211 as described above. Among the E1 C/A mutants, 207C, 229C 238C and 304C eliminated essentially all of binding activity of HMAb H-114, while 272C and 281C showed no effect on the binding activity of HMAb H-114 to E1 mutated protein.

Immunoprecipitation analysis of alanine mutations of the HMAb H-114 binding site on HCV E1 was performed. HEK-293 cells were transfected with the mutations and 24 hours after transfection cytoplasmic extracts were prepared. Extracts were subjected to immunoprecipitation with HMAb H-114. Bound protein was eluted with SDS sample buffer and subjected to SDS-PAGE and Western blot. Blotted E1 protein was detected with 2 μg/ml of the ECM E1 murine antibody.

Figure 46:
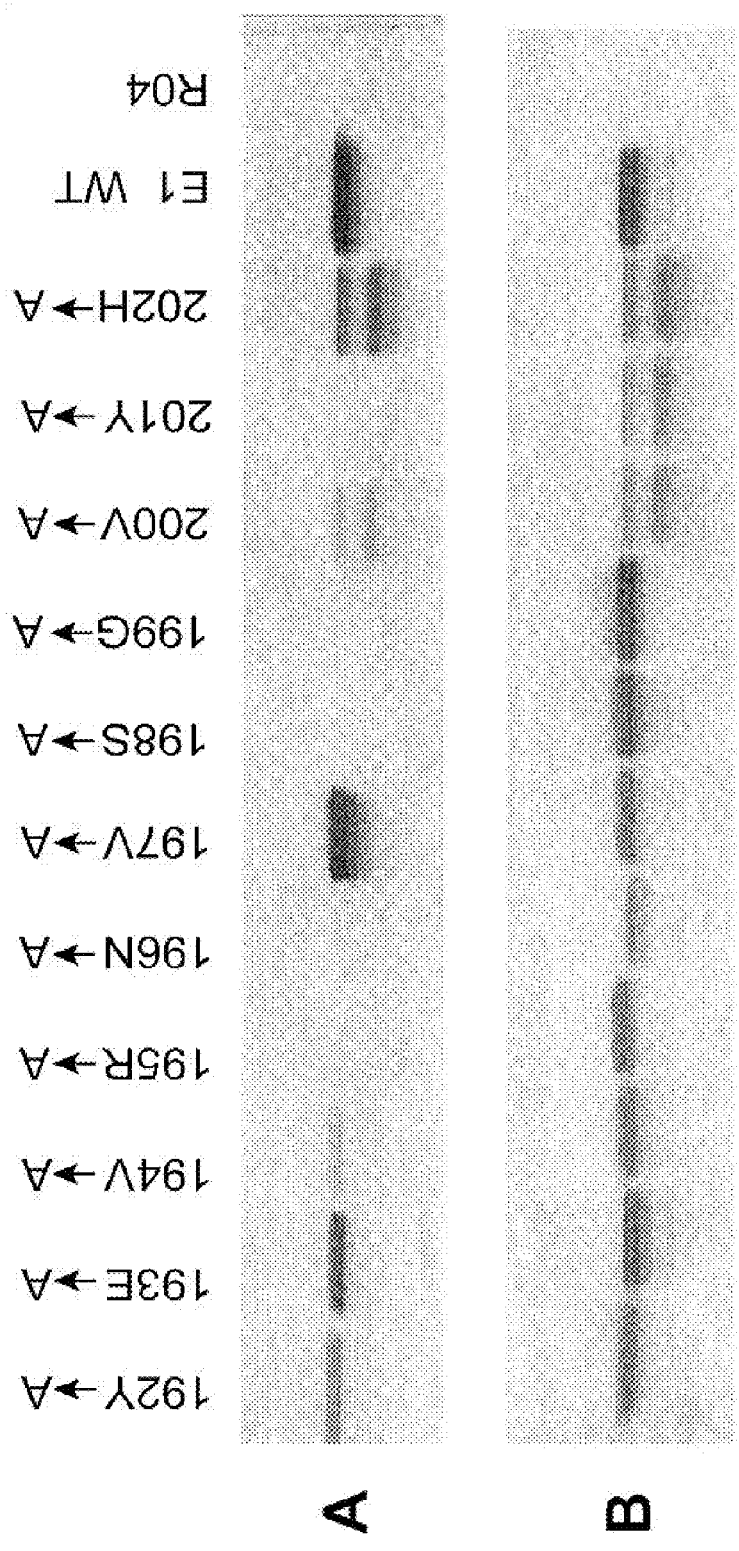
FIG. 46 is a Western blot of different E1 mutants.

As shown in FIG. 46, the number on the top of each lane indicates the location of cysteine residues on the E1 glycoprotein that were substituted with Alanine. Migration of molecular weight standards are as indicated at the left. Protein expression was evaluated with HA-tagged expression by Western Blot. These immunoprecipitation studies confirmed that mutants 207C, 229C 238C and 304C were not able to be detected by H-114, while 272C and 281C showed no effect on the binding activity of HMAb H-114 to E1 mutated protein (FIG. 46).

Example 11

Antibody Production

The following Example provides a variety of methods by which to produce HCV HMAbs.

Expression and purification of antibody from a plasmid vector. The gene encoding the entire antibody molecule can be amplified from its parent hybridoma by RT-PCT and cloned into a heterologous expression cassette capable of driving expression of the antibody in a constitutive or inducible manner in a eukaryotic cell line. For example, the antibody genes can be expressed in an expression plasmid such as pcDNA3.1 Zeo, pIND(SP1), or pREP8, (all from Invitrogen, Carlsbad, Calif.) and equivalents. Alternatively, the antibody genes can be expressed via viral or retroviral vectors such as MLV based vectors, vaccinia virus-based vectors or Adenovirus-based vectors. Similarly, the antibody genes can be expressed in insect virus vectors such as baculovirus vectors. Other vectors, such as the pCOMB series of vectors allow for expression of an antibody heavy and light chain pair or a single chain antibody on the surface of M13 phage or bacteria.

Once expressed, the antibody can be purified using, e.g., protein-A or protein-G sepharose, and the purified antibody can be chemically or enzymatically modified in any of the following ways: biotinylation using, e.g., biotin-C11-hydroxysuccinimide ester; coupling to beads of various formats, e.g., sepharose, agarose, magnetic, polystyrene, through the use of cyanogen bromide; or bridging the antibody to a useful chemical moiety, e.g., by modifying a lysine or other basic residues or through the use of reagents specific for free sulfhydryl groups.

Example 12

Neutralization of HCV Infectivity In Vitro by Human Monoclonal Antibodies to HCV E2

The capacity of the panel of HMAbs to neutralize infectivity of HCV in vitro was examined using an HCV pseudoparticle system. The HCV pseudoparticles comprise HCV E1 and E2 glycoproteins displayed on retroviral and lentiviral core proteins along with Luciferase (Luc) as a marker. These recombinant pseudoparticles are capable of infecting primary hepatocytes as well as hepato-carcinoma cells in vitro. The construction of the pseudoparticles and the in vitro infection assays were performed according to Bartosch et al., *J. exp. Med.* (2003) 197:633-642. In brief, Huh-7 human hepatocellular carcinoma cells (Nakabayashi et al. 1982, Cancer res. 42: 3858-3863) were incubated with supernatants containing the pseudoparticles in the presence or absence of anti-HCV E2 antibodies. Percent reduction with specific antibody was calculated using no antibody Luc value as 100%. As shown in FIGS. 47A and 47B, three antibodies (CBH-2, CBH-5 and CBH-7) significantly reduced the infectivity of the HCV pseudoparticles. The observation that CBH-2, CBH-5 and CBH-7 have neutralizing activity in this system provides an indication of their capability to interfere with HCV infection of susceptible cells.

The recent establishment of a B-cell line (SB) from an HCV-infected non-Hodgkin's B-cell lymphoma that continuously produces infectious HCV virions in culture has permitted a robust means to measure virus neutralization. Virions from SB can infect primary human hepatocytes, PBMCs, and a B-cell line (Raji cells) in vitro. We tested the ability of our anti HCV antibodies to neutralize infection of Raji cells by HCV virions. Production of HCV virions, determination of viral titer and HCV infection assays have been described previously (Sung VM-H et al., 2003 J. Virol. 77:2134-2146). Various anti-HCV antibodies (CBH-2, CBH-4B, CBH-4D, CBH-4G, CBH-5, CBH-7, CBH-8C, CBH-11 and CBH-17) were incubated with concentrated SB culture supernatant for 2 hours and than added to Raji cells. An unrelated HMAb (RO4) was used as an isotype-matched negative control and interferon alpha (IFN) was used as a positive control. Five days post infection, cells were washed 3× with PBS and RT-PCR analysis was performed at day 8 or 10. When HCV (SB) virions were pre-incubated with CBH-2, CBH-5, CBH-7 and CBH-11, viral RNA titer in Raji cells was reduced when compared to R04 isotype-matched non-relevant antibody or to no-antibody added control. These results suggested that CBH-2, CBH-5, CBH-7 and CBH-11 mediate virus neutralization. Results of this experiment are presented in Table 15.

TABLE 15

Infectivity neutralizing activity of HCV E2 monoclonal antibodies

| No Ab | Ro4 | CBH-2 | CBH-4B | CBH-4D | CBH-4G | CBH-5 | CBH-7 | CBH-8C | CBH-11 | CBH-17 | No virus | IFN |
|---|---|---|---|---|---|---|---|---|---|---|---|---|
| + | + | --- | + | + | + | --- | --- | + | --- | + | --- | --- |

Example 13

Specific Binding of HCV E2 Monoclonal Antibodies to HCV

Materials and Methods

Immunohistostaining of HCV-infected liver. Immunohistostaining of human liver tissue with CBH-5 was performed on liver fragments from HCV-infected patients. Human liver fragments from HBV-infected patients were used as negative control. The immunohistostaining was performed as follows: liver tissue fragments from HCV or HBV infected patients were fixed in 4% neutral buffered formaldehyde for 24 hours and then embedded in paraffin using routine procedures. Slices of 4-μm thickness were cut from paraffin blocks and mounted on polylysine-coated slides. After deparaffinization, the DAKO Envision™ system +HRP Kit (AEC) was used for peroxidase quenching and blocking. Staining was performed using CBH5 followed by HRP conjugated goat anti-human IgG (H+ L) and the kit's HRP substrate.

Immunoprecipitation of HCV from human infected sera. To determine the ability of CBH-5 to bind HCV particles, an immuno-magnetic separation (IMS) assay was developed. In this assay HCV particles, obtained from infected patients' sera with titers of $1-5\times10^6$ copies/ml, are captured on magnetic beads coated with a specific antibody. Following magnetic separation of bound and non-bound fractions, HCV-RNA is detected by RT-PCR. CBH-5 (4 µg) was coated on protein-A magnetic beads (Dynal A.S.) according to manufacturer instructions. HBV-AB17, a monoclonal antibody raised against HBV, served as a negative control. Antibody coated beads were washed three times in 0.1 M Na—P buffer (pH=8.1), blocked for 30 minutes in 1% BSA, and washed again in PBS before re-suspension in PBS-0.1% BSA. In parallel, tested serum from an infected individual was pre-treated with protein-A sepharose (Pharmacia) to eliminate serum antibodies. This was achieved by incubating 10 µL serum with 10 µL protein-A sepharose for 30 minutes with shaking, followed by a centrifugation step. The antibody-depleted serum was then incubated with shaking for 2 hours in the presence of the antibody-coated magnetic beads. PBS containing 0.1% BSA was used to complete the final volume to 200 µL. The bound fraction, magnetically separated from the non-bound fraction, was washed five times with 1 ml PBS before final re-suspension in 200 µl PBS.

Evaluation of viral amounts in the bound fraction was performed by RT-PCR analysis. Viral RNA was extracted using Tri-Reagent BD (Sigma) according to manufacturer instructions. RT reaction (20 µL final volume) contained 4 µl RT buffer, 1 mM dNTPs, 10 mM DTT, 100 U mMLV-RT (Promega), 2.7 U AMV-RT (Promega), and 2.5 pM HCV anti-sense primer ATGRTGCTCGGTCTA (SEQ ID NO: 36). Reaction conditions were set to ramping from 37° C. to 42° C., with a 1° C. increment every 20 minutes. Reaction was completed by a 10-minute incubation step at 94° C. Five (5) µL of RT reaction was used as a template for a PCR reaction (50 µL final volume). PCR reactions contained 5 µL PCR buffer, 2.5 mM $MgCl_2$, 0.2 mM dNTPs, 0.25 U Taq polymerase (Promega), 0.25 pM sense primer CACTCCACC-ATRGATCACTCCC (SEQ ID NO: 37), and anti-sense primer ACTCGCAAGCACCCTATCAGG (SEQ ID NO: 38). Thirty-three (33) amplification cycles of 1 minute at 94° C., 1 minute at 58° C., and 1.5 minutes at 72° C. were performed, with a final 5-minute elongation step at 72° C. PCR products were separated on a 2% agarose gel, visualized, and quantified following EtBr staining on an EagleEye II device.

Results

Figure 47A:
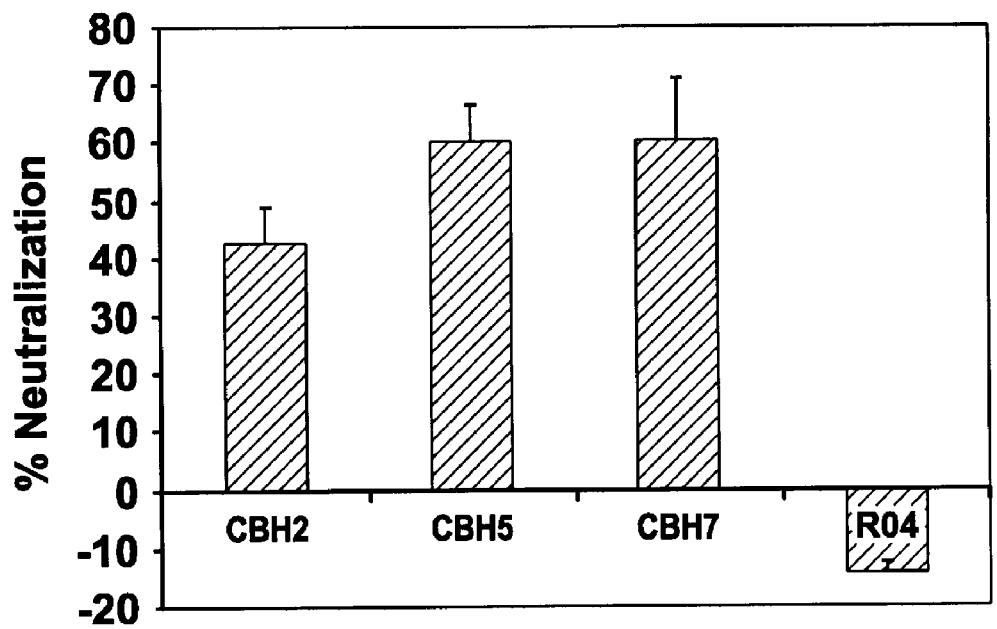
FIGS. 47A and 47B are graphs showing neutralization of HCV pseudoparticles by human monoclonal antibodies (HMAbs).
Figure 47B:
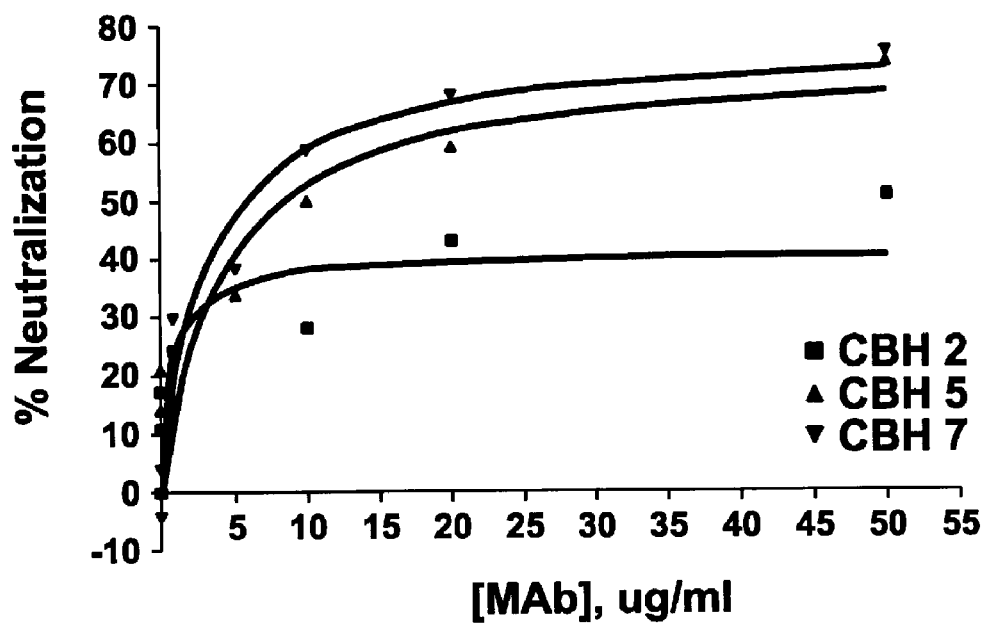
Figure 48:
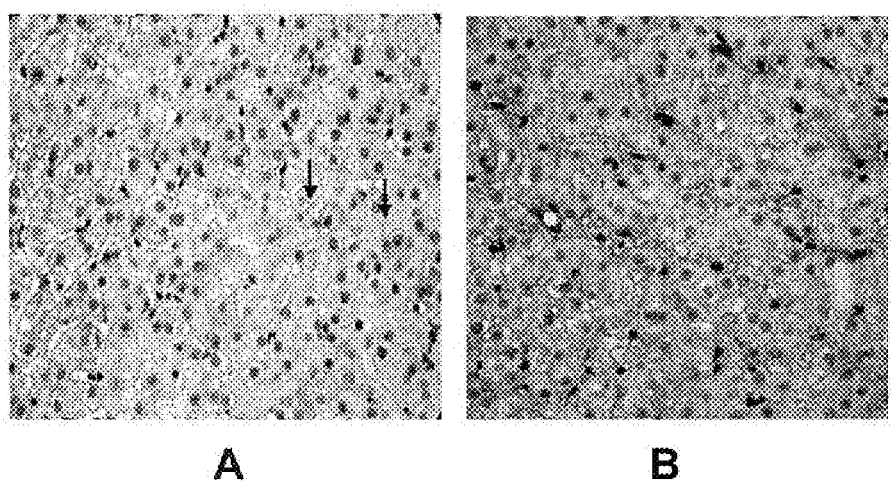
FIGS. 48A and 48B show photographs of liver fragments obtained from hepatitis virus infencted patients and stained with CBH-5.

As shown in FIGS. 47A and 47B, CBH-5 binds specifically to hepatocytes from HCV-infected liver tissue (FIG. 47A) and not to the HBV-infected liver (FIG. 47B), recognizing viral antigen presented on the surface of cells infected with HCV but not viral antigen on cells infected with HBV.

Figure 49:
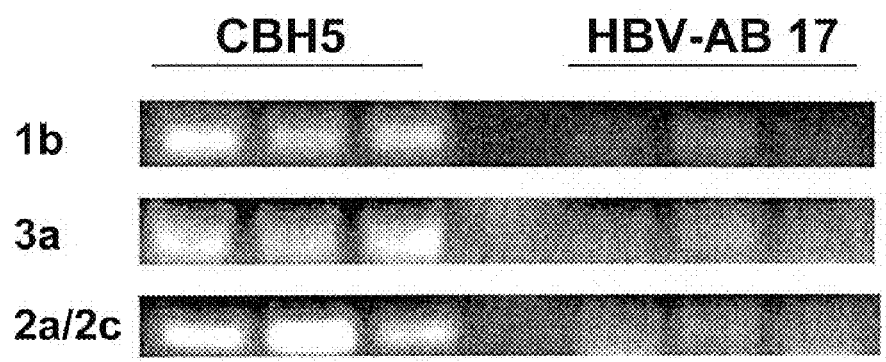
FIG. 49 is a photograph of an agarose gel on which PCR products representing HCV RNA were separated, and visualized by EtBr staining. 1b, 3a and 2a/2c represent different HCV genotypes. In the left panel the capturing beads were coated with CBH5. In the right panel the capturing beads were coated with the control antibody HBV-AB17.

CBH-5 was able to precipitate viral particles from infected patients' sera (three different patients with three different HCV genotypes) in contrast to a non-relevant antibody used as a negative control (human monoclonal antibody to HBV) (FIG. 49).

Example 14

Efficacy of Monoclonal Antibodies to HCV E2 in Preventing and Treating HCV in an Animal Model Materials and Methods HCV-Trimera mouse system. The biological activity of the human monoclonal antibodies was characterized using the following HCV-Trimera animal model (Ilan et al JID 2002, 185:153-161; U.S. Pat. No. 5,849,987): CB6F1 mice were treated so as to allow the stable engraftment of human liver fragments. The treatment included exposure to split-dose total body irradiation (4 Gy followed 1 day later by 11 Gy) from a gamma beam 150-A $^{60}$Co source (Atomic Energy of Canada). After irradiation, mice were injected intravenously with $5\times10^6$ SCID mouse bone marrow cells and then received an HCV-infected human liver fragment transplant either behind the ear pinna or under the kidney capsule. Viral infection of human liver fragments was performed ex vivo using HCV positive human serum. Measurement of HCV-RNA extracted from the sera of Trimera mice was achieved by reverse-transcription polymerase chain reaction (RT-PCR) as described in Example 13.

Statistical analysis. Statistical analysis was performed with the StatView II software program (Abacus Concepts). Differences in the percentage of HCV-positive animals were compared by the 2-tailed Fisher's exact test; differences in virus load were compared by the nonparametric Mann-Whitney U test. Regression analysis was used for the construction of standard curves for the quantitative evaluation of HCV RNA.

The biological effect of the antibodies was tested in two different settings: inhibition of infection and treatment.

Inhibition of infection. Samples of human sera (250 µl) containing $1.5\times10^6$ HCV-RNA copies/ml were pre-incubated with 100 µg of the anti HCV antibodies for 3 h at room temperature and subsequently used to infect normal human liver fragments ex vivo. Following infection, the liver fragments were transplanted in mice and HCV-RNA was determined in sera 15 days later.

Treatment/dose response. To test reduction of viral load in HCV-positive mice, two intraperitoneal injections of either CBH-2 or CBH-5 were administered to Trimera mice with established HCV viremia; the total dose of HMAb was 40 µg per mouse, given on two consecutive days (i.e., 20 µg/mouse/day at days 16 and 17 post infection). HCV-RNA was measured in mouse sera sampled 1 day after treatment completion.

Results

Figure 50:
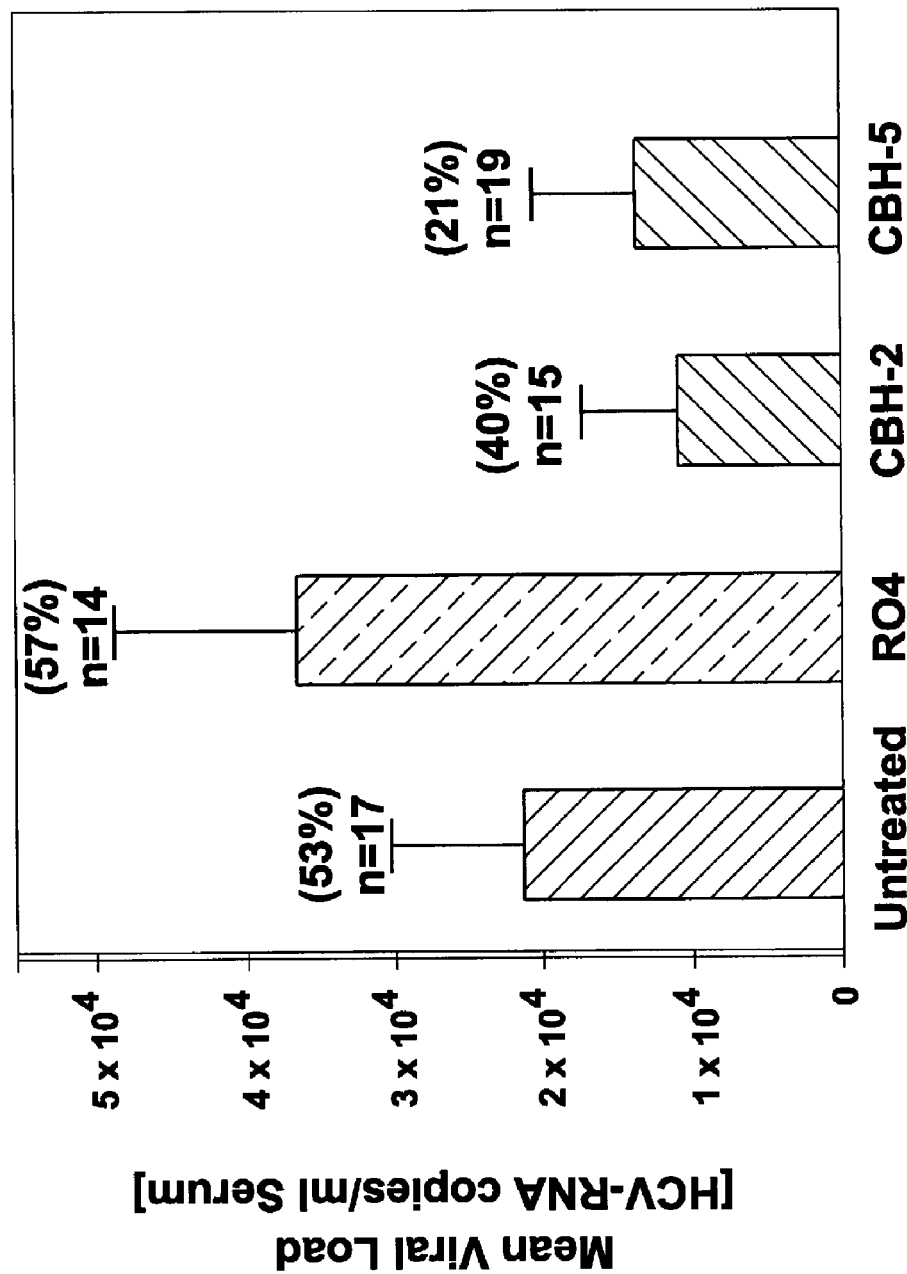
FIG. 50 is a graphic representation of the mean viral load and percentage of HCV-Trimera mice with positive HCV RT-PCR signal in their serum (numbers in parentheses) at day 15 after transplantation in the untreated group, CBH-2 treated group, CBH-5 treated group and in a control group treated with the non-relevant antibody RO4.

FIG. 50 shows the effect of CBH-2 and CBH-5 antibodies in inhibiting liver infection by HCV, as demonstrated by both the mean viral load and the percentage of HCV-RNA positive mice. CBH-2 and CBH-5 were effective in reducing both viral infection parameters. CBH-5, for example, reduced the percentage of HCV infected mice from 53% in the control non-treated group to 21%. It also reduced the mean viral load from $2.12\times10^4$ to $1.33\times10^4$ HCV-RNA copies/ml mouse sera. An equal amount (100 µg) of the non-relevant human monoclonal antibody, RO4, was not able to reduce neither the percentage of positive mice nor the viral load (FIG. 50).

In a different experiment, antibody CBH-7 was able to reduce the percentage of HCV positive mice from 80% to 19% and the mean viral load from $2.74\times10^4$ to $5.94\times10^3$ HCV-RNA copies/ml as measured in sera that were sampled 17 days post transplantation.

Figure 51:
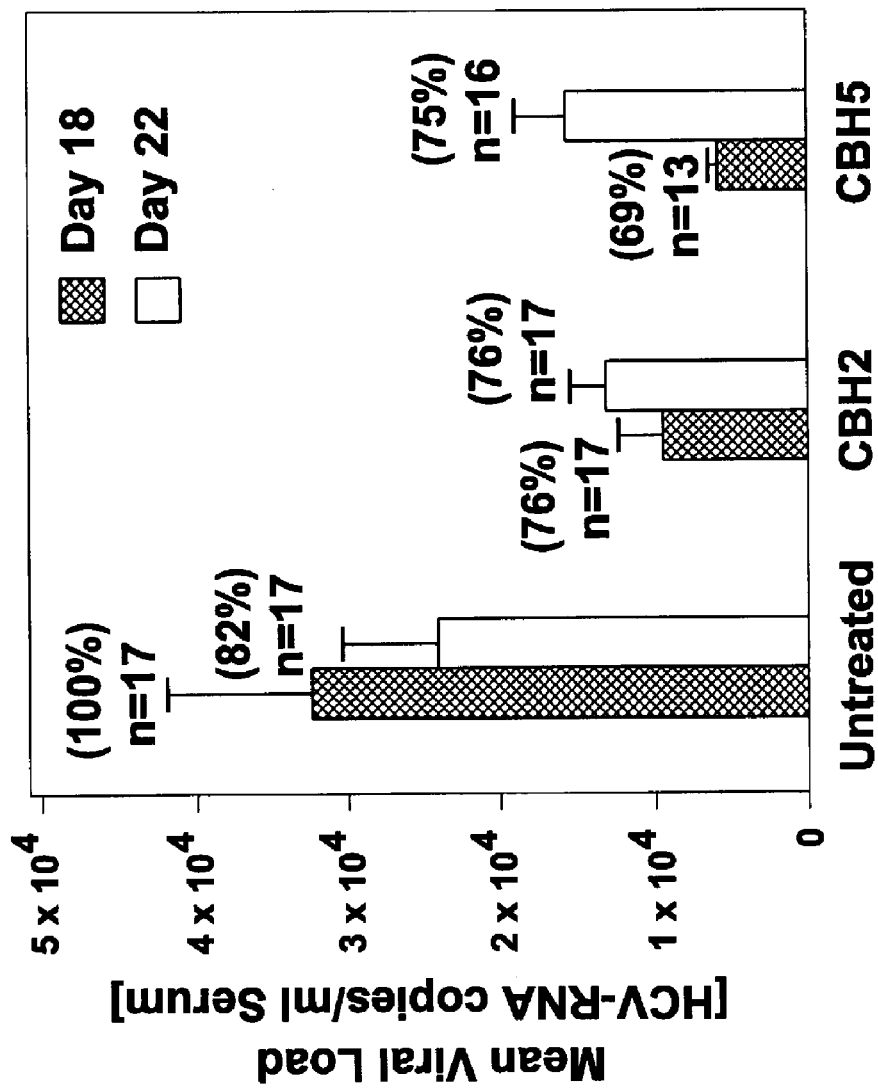
FIG. 51 is a graphic representation of the mean viral load and percentage of HCV-Trimera mice with positive HCV RT-PCR signal in their serum (numbers in parentheses) at days 18 and 22 after transplantation in the untreated group, CBH-2 treated group, and CBH-5 treated group.

FIG. 51 shows the effect of the CBH-2 and CBH-5 in inhibiting HCV infection, as demonstrated by both the mean viral load and the percentage of HCV-RNA positive mice.

CBH-2 and CBH-5 were effective in reducing both viral infection parameters. CBH-5 for example reduced the percentage of HCV infected mice from 100% in the control non-treated group to 69% (as measured on day 18). It also reduced the mean viral load from about $3\times10^4$ to less than $1\times10^4$ HCV-RNA copies/ml in mouse sera. At day 22 (5 days after the second antibody injection) the viral load increased as compared to day 18.

Figure 52:
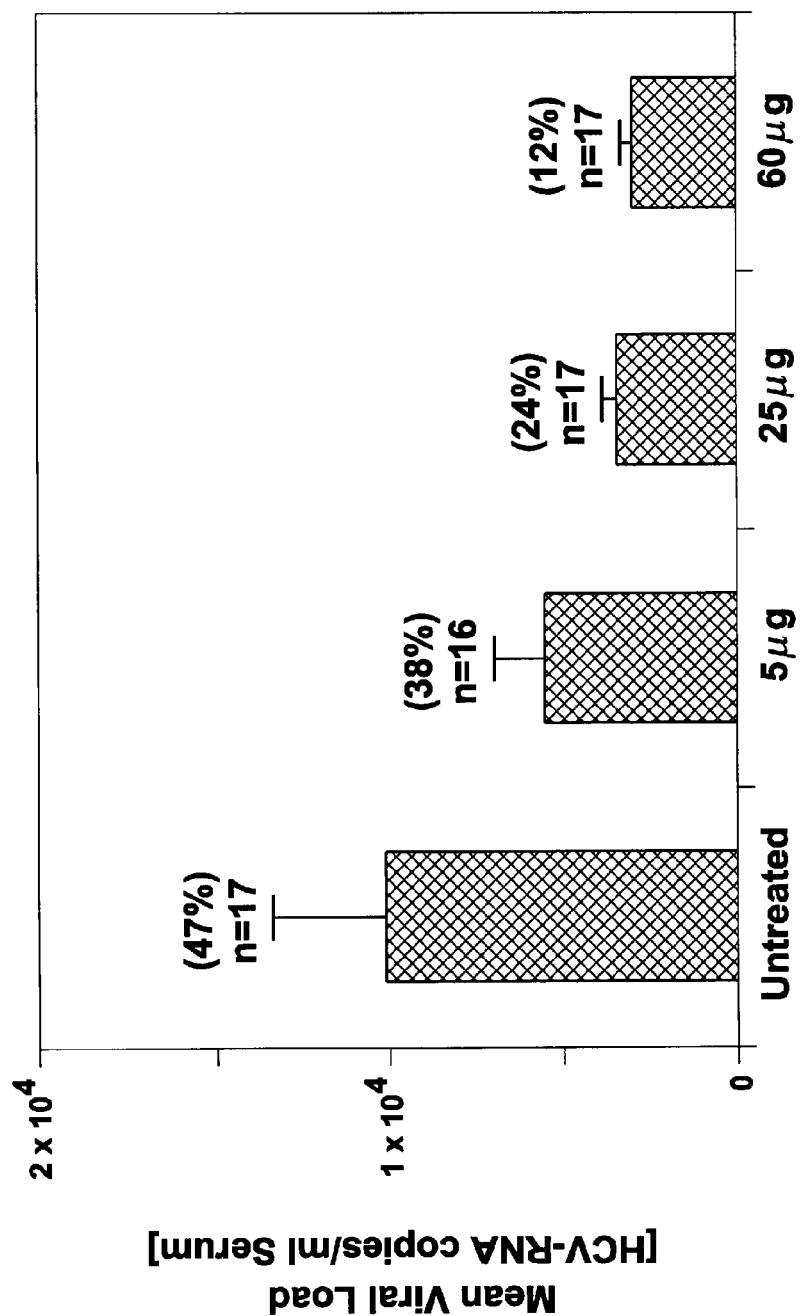
FIG. 52 is a graphic representation of the mean viral load and percentage of HCV-Trimera mice with positive HCV RT-PCR signal in their serum (numbers in parentheses) at day 18 after transplantation in the untreated group and in groups treated with various amounts of CBH-5 (5, 25 and 60 μg).

FIG. 52 shows the effect of CBH-5 in reducing viral load and that the percentage of HCV-positive mice is dose dependent. A total dose of 5 μg CBH-5 per mouse (given on day 18) reduced the viral load from $1\times10^4$ to $5.5\times10^3$ HCV-RNA copies/ml in the serum and reduced the percentage of HCV-RNA positive mice from 47% to 38%, as measured 1 day post-treatment. The highest dose of CBH-5, 60 μg/mouse, produced the strongest effect, reduced the viral load from $1\times10^4$ to $2.9\times10^3$ copies/ml and reduced the percentage of HCV-positive mice from 47% to 12%.

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. A pharmaceutical composition for treating HCV infection comprising: an antibody to HCV E2 protein selected from the group consisting of CBH-2, CBH-5 and CBH-7; and a pharmaceutically acceptable carrier.

2. A pharmaceutical composition according to claim 1 further combined with at least one other antiviral agent as an additional active ingredient.

3. The pharmaceutical composition of claim 2, wherein said agent is selected from the group consisting of interferons, anti HCV monoclonal antibodies, anti-HCV polyclonal antibodies, RNA polymerase inhibitors, ribavirin, protease inhibitors, IRES inhibitors, helicase inhibitors, antisense compounds, short interfering RNAs, short hairpin RNAs, and ribozymes.

4. The pharmaceutical composition according to claim 2, wherein the other antiviral agent is an anti-HCV monoclonal antibody.

5. A pharmaceutical composition for treating or reducing the recurrence of HCV infection comprising a fragment of a monoclonal antibody selected from the group consisting of CBH-2 which is secreted by the hybridoma cell line deposited in the ATCC under Accession no. PTA-4465, CBH-5 which is secreted by the hybridoma cell line deposited in the ATCC under Accession no. PTA-4469, and CBH-7 which is secreted by the hybridoma cell line deposited in the ATCC under Accession no. PTA-4470, wherein the fragment retains the antigen binding specificity of the whole antibody; and a pharmaceutically acceptable carrier.

6. A method for the treatment of HCV infection comprising administering to an individual in need of treatment for HCV infection a therapeutically effective amount of a pharmaceutical composition according to claim 1.

7. A method for reducing the recurrence of HCV infections in a subject by passive immunotherapy, comprising administering to the subject a pharmaceutical composition in accordance with claim 1.

8. A method for reducing the likelihood of a recurrent HCV infection in a liver transplantation patient, comprising administering to the patient an effective amount of a pharmaceutical composition, wherein the pharmaceutical composition comprises a pharmaceutically acceptable carrier and, as an active ingredient, a human monoclonal antibody to HCV E2 protein selected from the group consisting of:
   (a) the monoclonal antibody CBH-2 which is secreted by the hybridoma cell line deposited in the ATCC under Accession no. PTA-4465;
   (b) the monoclonal antibody CBH-5 which is secreted by the hybridoma cell line deposited in the ATCC under Accession no. PTA-4469;
   (c) the monoclonal antibody CBH-7 which is secreted by the hybridoma cell line deposited in the ATCC under Accession no. PTA-4470; and
   (d) fragments of the antibodies of (a)-(c) which retain the antigen binding characteristics of the whole antibody.

9. The method according to claim 6, wherein the pharmaceutical composition further comprises at least one other active ingredient which is an antiviral agent.

10. The method according to claim 9, wherein the antiviral agent is selected from the group consisting of interferons, anti HCV monoclonal antibodies, anti HCV polyclonal antibodies, RNA polymerase inhibitors, ribavirin, protease inhibitors, IRES inhibitors, helicase inhibitors, antisense compounds, short interfering RNAs, short hairpin RNAs, and ribozymes.

11. A method for reducing the recurrence of HCV infections in a subject comprising administering to the subject a pharmaceutical composition in accordance with claim 1.

12. The method of claim 11, wherein the subject is a baby born to an HCV infected mother.

* * * * *

UNITED STATES PATENT AND TRADEMARK OFFICE
CERTIFICATE OF CORRECTION

| | | |
|---|---|---|
| PATENT NO. | : 8,114,586 B2 | |
| APPLICATION NO. | : 12/332832 | |
| DATED | : February 14, 2012 | |
| INVENTOR(S) | : Foung et al. | |

It is certified that error appears in the above-identified patent and that said Letters Patent is hereby corrected as shown below:

In Column 1, line 28, directly beneath the subtitle "FEDERALLY-SPONSORED RESEARCH OR DEVELOPMENT" of the specification, please delete:

"This invention was made with Government support under contracts AI047355, DA0026596, and AI047355 awarded by the National Institutes of Health. The Government has certain rights in this invention."

and insert:

--This invention was made with Government support under contracts HL033811, DA0026596, and AI047355 awarded by the National Institutes of Health. The Government has certain rights in this invention.--

Signed and Sealed this
Eighth Day of May, 2012

David J. Kappos
*Director of the United States Patent and Trademark Office*

SEQUENCE LISTING

```
<160> NUMBER OF SEQ ID NOS: 30

<210> SEQ ID NO 1
<211> LENGTH: 160
<212> TYPE: DNA
<213> ORGANISM: Artificial
<220> FEATURE:
<223> OTHER INFORMATION: Is a comparison of sequences of HCV: using the
      most parsimonious tree found.

<400> SEQUENCE: 1
ctcaactgga ttcaccaaag tgtgcggagc gcctccttgt gtcatcggag gggcgggcaa      60
caacaccctg cactgcccca ctgattgctt ccgcaagcat ccggacgcca catactctcg    120
gtgcggctcc ggtccctgga tcacacccag gtgcctggtc                          160

<210> SEQ ID NO 2
<211> LENGTH: 9
<212> TYPE: DNA
<213> ORGANISM: Artificial
<220> FEATURE:
<223> OTHER INFORMATION: Is a comparison of sequences of HCV: using the
      most parsimonious tree found.

<400> SEQUENCE: 2 cctgtagtg                                                              9

<210> SEQ ID NO 3
<211> LENGTH: 45
<212> TYPE: DNA
<213> ORGANISM: Artificial
<220> FEATURE:
<223> OTHER INFORMATION: Is a comparison of sequences of HCV: using the
      most parsimonious tree found.

<400> SEQUENCE: 3
tagtgtgacg ccgaagtctc gtatgcgccg ttaaaaatgg tgtaa                      45

<210> SEQ ID NO 4
<211> LENGTH: 48
<212> TYPE: DNA
<213> ORGANISM: Artificial
<220> FEATURE:
<223> OTHER INFORMATION: Is a comparison of sequences of HCV: using the
      most parsimonious tree found.

<400> SEQUENCE: 4
tggcaggact gccaaagtct tactgctgcc gtacaaattg gtcgtaat                   48

<210> SEQ ID NO 5
```

```
<211> LENGTH: 59
<212> TYPE: DNA
<213> ORGANISM: Artificial
<220> FEATURE:
<223> OTHER INFORMATION: Is a comparison of sequences of HCV: using the
      most parsimonious tree found.

<400> SEQUENCE: 5
ccagactcaa cccgtactac tttgcgatgg actttggctt agttacatca aattgcgaa        59

<210> SEQ ID NO 6
<211> LENGTH: 57
<212> TYPE: DNA
<213> ORGANISM: Artificial
<220> FEATURE:
<223> OTHER INFORMATION: Is a comparison of sequences of HCV: using the
      most parsimonious tree found.

<400> SEQUENCE: 6
ctactcaacc cgactacttt tgcgacggac tggctagtat atcaaattgc tggaaaa          57

<210> SEQ ID NO 7
<211> LENGTH: 64
<212> TYPE: DNA
<213> ORGANISM: Artificial
<220> FEATURE:
<223> OTHER INFORMATION: Is a comparison of sequences of HCV: using the
      most parsimonious tree found.

<400> SEQUENCE: 7
ggggtgacat aaccgtagaa aactagtatc gattattgac ttagcattct ctaatagagt       60
tata                                                                   64

<210> SEQ ID NO 8
<211> LENGTH: 64
<212> TYPE: DNA
<213> ORGANISM: Artificial
<220> FEATURE:
<223> OTHER INFORMATION: Is a comparison of sequences of HCV: using the
      most parsimonious tree found.

<400> SEQUENCE: 8
tggggtgaca taaccgtaga actggactcg acattgacta acatatccta atagggttgc       60
aaaa                                                                   64

<210> SEQ ID NO 9
<211> LENGTH: 160
<212> TYPE: DNA
<213> ORGANISM: Artificial
<220> FEATURE:
<223> OTHER INFORMATION: Describes sequences amplified from the central
      region of the HCV E2 vaccinia virus clones.

<400> SEQUENCE: 9
ctcaactgga ttcaccaaag tgtgcggagc gccccctgt gtcatcggag gggcgggcaa        60
caacaccttg cgctgcccca ctgattgttt ccgcaagcat ccggaagcca cgtactctcg      120
gtgcggctcc ggtccctgga ttacgcccag gtgcctggtc                            160

<210> SEQ ID NO 10
<211> LENGTH: 160
<212> TYPE: DNA
<213> ORGANISM: Artificial
<220> FEATURE:
<223> OTHER INFORMATION: Describes sequences amplified from the central
      region of the HCV E2 vaccinia virus clones.
```

-continued

```
<400> SEQUENCE: 10
tggcacaggg ttcaccaaga cgtgtggggc cccccatgt aacatcgggg gggtcggcaa      60
taacaccttg acttgcccca cggactgttt ccggaagcac cccgaggcca cttacaccaa    120
atgtggttcg gggccttggc tgacacctag gtgcatagtt                          160

<210> SEQ ID NO 11
<211> LENGTH: 164
<212> TYPE: DNA
<213> ORGANISM: Artificial
<220> FEATURE:
<223> OTHER INFORMATION: Describes sequences amplified from the central
      region of the HCV E2 vaccinia virus clones.

<400> SEQUENCE: 11
ctccactgtt tcaccaaaac ttgcggcgca ccaccctgcc gcatcagagc tgactttaat     60
gccagcacgg acctgctgtg ccccacggac tgtttcagga agcatcctga agccacttac   120
atcaaatgtg gctctgggcc cctgtgacgc caaagtgcct gata                    164

<210> SEQ ID NO 12
<211> LENGTH: 166
<212> TYPE: DNA
<213> ORGANISM: Artificial
<220> FEATURE:
<223> OTHER INFORMATION: Describes sequences amplified from the central
      region of the HCV E2 vaccinia virus clones.

<400> SEQUENCE: 12
tgggactggg ttcactaaga catgcggtgc accaccttgc cgcattagga gggactgcaa     60
cggaaccctc gacctattgt gccccacaga ctgtttcaga aagcacccag atactaccta   120
ccttaagtgt ggagcggggc cttggttgac ccccaaatgc atggta                  166

<210> SEQ ID NO 13
<211> LENGTH: 8
<212> TYPE: PRT
<213> ORGANISM: Artificial
<220> FEATURE:
<223> OTHER INFORMATION: Sequences encoding high affinity epitopes.

<400> SEQUENCE: 13

Asp Tyr Lys Asp Asp Asp Asp Lys
1               5

<210> SEQ ID NO 14
<211> LENGTH: 10
<212> TYPE: PRT
<213> ORGANISM: Artificial
<220> FEATURE:
<223> OTHER INFORMATION: Sequences encoding high affinity epitopes.

<400> SEQUENCE: 14

Met Ala Ser Met Thr Gly Gly Gln Met Gly
1               5                   10

<210> SEQ ID NO 15
<211> LENGTH: 15
<212> TYPE: PRT
<213> ORGANISM: Artificial
<220> FEATURE:
<223> OTHER INFORMATION: Sequences encoding high affinity epitopes.

<400> SEQUENCE: 15

Lys Glu Thr Ala Ala Ala Lys Phe Glu Arg Gln His Met Asp Ser
1               5                   10                  15
```

-continued

```
<210> SEQ ID NO 16
<211> LENGTH: 20
<212> TYPE: DNA
<213> ORGANISM: Artificial
<220> FEATURE:
<223> OTHER INFORMATION: Reverse transcription reactions were performed
      using MMLV reverse transcriptase employing the reverse HCV
      specific primer HCV.

<400> SEQUENCE: 16
cgcgcacraa gtasggyact                                              20

<210> SEQ ID NO 17
<211> LENGTH: 20
<212> TYPE: DNA
<213> ORGANISM: Artificial
<220> FEATURE:
<223> OTHER INFORMATION: Forward primer.

<400> SEQUENCE: 17
cgcatggctg ggayatgatg                                              20

<210> SEQ ID NO 18
<211> LENGTH: 29
<212> TYPE: PRT
<213> ORGANISM: Artificial
<220> FEATURE:
<223> OTHER INFORMATION: Forward primer employed in cloning HCV E2
      protein.

<400> SEQUENCE: 18

Cys Gly Ala Gly Gly Cys Ile Thr Cys Ala Thr Ala Thr Gly Ala Thr
1               5                  10                  15

Cys Gly Cys Thr Gly Gly Thr Gly Cys Thr Thr Gly Gly
            20                  25

<210> SEQ ID NO 19
<211> LENGTH: 38
<212> TYPE: DNA
<213> ORGANISM: Artificial
<220> FEATURE:
<223> OTHER INFORMATION: Reverse primer employed in cloning HCV E2
      protein.

<400> SEQUENCE: 19
cggaatccct gcagctacaa actggcttga agaatcca                          38

<210> SEQ ID NO 20
<211> LENGTH: 34
<212> TYPE: DNA
<213> ORGANISM: Artificial
<220> FEATURE:
<223> OTHER INFORMATION: Forward primer employed in cloning HCV E2
      protein.

<400> SEQUENCE: 20
cgcatatgga gctcgcgggg gcccactggg gagt                              34

<210> SEQ ID NO 21
<211> LENGTH: 38
<212> TYPE: DNA
<213> ORGANISM: Artificial
<220> FEATURE:
<223> OTHER INFORMATION: Reverse primer employed in cloning HCV E2
      protein.

<400> SEQUENCE: 21
```

-continued gctctagact gcagctatat gccagcctgg agcaccat                    38

<210> SEQ ID NO 22
<211> LENGTH: 34
<212> TYPE: DNA
<213> ORGANISM: Artificial
<220> FEATURE:
<223> OTHER INFORMATION: Forward primer employed in cloning HCV E2
      protein.

<400> SEQUENCE: 22
cgctcgagcc atggttggcg gggctcattg gggc                        34

<210> SEQ ID NO 23
<211> LENGTH: 40
<212> TYPE: DNA
<213> ORGANISM: Artificial
<220> FEATURE:
<223> OTHER INFORMATION: Reverse primer employed in cloning HCV E2
      protein.

<400> SEQUENCE: 23
tcgaattcgg atcctacaaa gcacctttta ggagataagc                  40

<210> SEQ ID NO 24
<211> LENGTH: 34
<212> TYPE: DNA
<213> ORGANISM: Artificial
<220> FEATURE:
<223> OTHER INFORMATION: Forward primer employed in cloning HCV E2
      protein.

<400> SEQUENCE: 24
cgctcgagcc atggttttcg gcggccattg ggtg                        34

<210> SEQ ID NO 25
<211> LENGTH: 40
<212> TYPE: DNA
<213> ORGANISM: Artificial
<220> FEATURE:
<223> OTHER INFORMATION: Reverse primer employed in cloning HCV E2
      protein.

<400> SEQUENCE: 25
tcgaattcgg atcctacaga gacgctttaa ggaggtaggc                  40

<210> SEQ ID NO 26
<211> LENGTH: 23
<212> TYPE: PRT
<213> ORGANISM: Artificial
<220> FEATURE:
<223> OTHER INFORMATION: Forward primer employed in cloning HCV E2
      protein.

<400> SEQUENCE: 26

Thr Gly Gly Thr Thr Cys Gly Gly Asx Thr Gly Tyr Trp Cys Ile Thr
1               5                   10                  15

Gly Gly Ala Thr Gly Ala Ala
            20

<210> SEQ ID NO 27
<211> LENGTH: 26
<212> TYPE: PRT
<213> ORGANISM: Artificial
<220> FEATURE:
<223> OTHER INFORMATION: Reverse primer employed in cloning HCV E2
      protein.

```
<400> SEQUENCE: 27

Thr Ala Ala Thr Gly Cys Cys Ala Ile Ala Arg Cys Cys Lys Arg Thr
1               5                   10                  15

Ala Ile Gly Gly Gly Thr Ala Gly Thr Cys
            20                  25

<210> SEQ ID NO 28
<211> LENGTH: 15
<212> TYPE: DNA
<213> ORGANISM: Artificial
<220> FEATURE:
<223> OTHER INFORMATION: Anti-sense primer.

<400> SEQUENCE: 28
atgrtgctcg gtcta                                                        15

<210> SEQ ID NO 29
<211> LENGTH: 22
<212> TYPE: DNA
<213> ORGANISM: Artificial
<220> FEATURE:
<223> OTHER INFORMATION: Sense primer.

<400> SEQUENCE: 29
cactccacca trgatcactc cc                                                22

<210> SEQ ID NO 30
<211> LENGTH: 21
<212> TYPE: DNA
<213> ORGANISM: Artificial
<220> FEATURE:
<223> OTHER INFORMATION: Anti-sense primer.

<400> SEQUENCE: 30
actcgcaagc accctatcag g                                                 21
```